US008034375B2

(12) United States Patent
Desai et al.

(10) Patent No.: US 8,034,375 B2
(45) Date of Patent: Oct. 11, 2011

(54) COMBINATIONS AND MODES OF ADMINISTRATION OF THERAPEUTIC AGENTS AND COMBINATION THERAPY

(75) Inventors: Neil P. Desai, Santa Monica, CA (US); Patrick Soon-Shiong, Los Angeles, CA (US)

(73) Assignee: Abraxis Bioscience, LLC, Los Angeles, CA (US)

( * ) Notice: Subject to any disclaimer, the term of this patent is extended or adjusted under 35 U.S.C. 154(b) by 173 days.

(21) Appl. No.: 11/359,286

(22) Filed: Feb. 21, 2006

(65) Prior Publication Data

US 2006/0263434 A1 Nov. 23, 2006

Related U.S. Application Data

(60) Provisional application No. 60/654,245, filed on Feb. 18, 2005.

(51) Int. Cl.
*A61K 9/127* (2006.01)
*A61K 38/16* (2006.01)

(52) U.S. Cl. ............. 424/450; 514/34; 514/40; 514/50

(58) Field of Classification Search .............. 424/422, 424/428, 486, 489, 78.17, 400, 423, 436, 424/450; 514/8, 27, 34, 44, 50, 109, 283, 514/449, 358, 359; 435/6, 7.23
See application file for complete search history.

(56) References Cited

U.S. PATENT DOCUMENTS

| | | | |
|---|---|---|---|
| 5,362,478 A | 11/1994 | Desai et al. | |
| 5,439,686 A | 8/1995 | Desai et al. | |
| 5,470,571 A | 11/1995 | Herlyn et al. | |
| 5,498,421 A | 3/1996 | Grinstaff et al. | |
| 5,505,932 A | 4/1996 | Grinstaff et al. | |
| 5,508,021 A | 4/1996 | Grinstaff et al. | |
| 5,512,268 A | 4/1996 | Grinstaff et al. | |
| 5,558,864 A | 9/1996 | Bendig et al. | |
| 5,560,933 A | 10/1996 | Soon-Shiong et al. | |
| 5,635,207 A | 6/1997 | Grinstaff et al. | |
| 5,639,473 A | 6/1997 | Grinstaff et al. | |
| 5,650,156 A | 7/1997 | Grinstaff et al. | |
| 5,651,986 A | 7/1997 | Brem et al. | |
| 5,662,883 A | 9/1997 | Bagchi et al. | |
| 5,665,382 A | 9/1997 | Grinstaff et al. | |
| 5,665,383 A | 9/1997 | Grinstaff et al. | |
| 5,690,928 A | 11/1997 | Heimbrook et al. | |
| 5,733,925 A | 3/1998 | Kunz et al. | |
| 5,744,460 A | 4/1998 | Muller et al. | |
| 5,859,018 A | 1/1999 | Brown et al. | |
| 5,873,904 A | 2/1999 | Ragheb et al. | |
| 5,886,026 A | 3/1999 | Hunter et al. | |
| 5,916,596 A | 6/1999 | Desai et al. | |
| 5,977,163 A | 11/1999 | Li et al. | |
| 5,981,568 A | 11/1999 | Kunz et al. | |
| 5,994,341 A | 11/1999 | Hunter et al. | |
| 5,997,904 A | 12/1999 | Magdassi et al. | |
| 6,096,070 A | 8/2000 | Ragheb et al. | |
| 6,096,331 A * | 8/2000 | Desai et al. | 424/422 |
| 6,143,276 A | 11/2000 | Unger | |
| 6,239,124 B1 | 5/2001 | Zenke et al. | |
| 6,268,390 B1 | 7/2001 | Kunz | |
| 6,306,421 B1 | 10/2001 | Kunz et al. | |
| 6,506,405 B1 * | 1/2003 | Desai et al. | 424/450 |
| 6,515,009 B1 | 2/2003 | Kunz et al. | |
| 6,528,067 B1 | 3/2003 | Magdassi et al. | |
| 6,537,579 B1 | 3/2003 | Desai et al. | |
| 6,544,544 B2 | 4/2003 | Hunter et al. | |
| 6,548,531 B2 | 4/2003 | Breimer et al. | |
| 6,566,405 B2 | 5/2003 | Weidner et al. | |
| 6,569,441 B2 | 5/2003 | Kunz et al. | |
| 6,652,884 B2 * | 11/2003 | Falciani | 424/489 |
| 6,682,758 B1 | 1/2004 | Tabibi et al. | |
| 6,689,803 B2 | 2/2004 | Hunter et al. | |
| 6,727,256 B1 | 4/2004 | Carter et al. | |
| 6,730,699 B2 | 5/2004 | Li et al. | |
| 6,749,868 B1 | 6/2004 | Desai et al. | |
| 6,752,803 B2 | 6/2004 | Goldman et al. | |
| 6,753,006 B1 | 6/2004 | Desai et al. | |
| 6,872,715 B2 | 3/2005 | Santi et al. | |
| 6,884,817 B2 | 4/2005 | Li et al. | |
| 6,884,879 B1 | 4/2005 | Baca et al. | |
| 6,929,818 B2 | 8/2005 | Luthra et al. | |
| 7,038,071 B2 | 5/2006 | Lal | |

(Continued)

FOREIGN PATENT DOCUMENTS

EP      0 584 001 A1 *    2/1994

(Continued)

OTHER PUBLICATIONS

James R. Rigas, Taxane-Platinun combination in Advanced Non-Small Cell Lung Cancer: A Review, The Oncologist, vol. 9, Suppl 2, 16-23, Jun. 2, 2004.*
Adis Data Information BV. (Aug. 28, 2004). "Paclitaxel [Taxol] and Liposomal Doxorubicin [Caelyx] Cotherapy Appears to be an Effective First-line Treatment in Patients with Metastatic Breast Cancer," *Inpharma* (1452):8.
Ashkenas, J. (Mar./Apr. 2003). "The Metronome Ticks On," *Preclinica*, located at <ww.preclinica.com>, pp. 1-2.
Bertolini, F. et al. (Aug. 1, 2003). "Maximum Tolerable Dose and Low-Dose Metronomic Chemotherapy Have Opposite Effects on the Mobilization and Viability of Circulating Endothelial Progenitor Cells," *Cancer Res.* 63(15):4342-4346.

(Continued)

*Primary Examiner* — Michael G Hartley
*Assistant Examiner* — Jagadishwar Samala
(74) *Attorney, Agent, or Firm* — Morrison & Foerster LLP

(57) ABSTRACT

The present invention provides combination therapy methods of treating proliferative diseases (such as cancer) comprising a first therapy comprising administering to an individual an effective amount of a taxane in a nanoparticle composition, and a second therapy which may include, for example, radiation, surgery, administration of chemotherapeutic agents, or combinations thereof. Also provided are methods of administering to an individual a drug taxane in a nanoparticle composition based on a metronomic dosing regime.

34 Claims, 9 Drawing Sheets

U.S. PATENT DOCUMENTS

| | | | |
|---|---|---|---|
| 7,129,368 B2 | 10/2006 | Lal | |
| 7,141,576 B2 | 11/2006 | Lackey et al. | |
| 7,232,919 B2 | 6/2007 | Lal | |
| 7,332,568 B2 | 2/2008 | Trieu et al. | |
| 2002/0031505 A1* | 3/2002 | Bissery | 424/94.1 |
| 2002/0169140 A1 | 11/2002 | Prendergast | |
| 2003/0185894 A1 | 10/2003 | Zenoni et al. | |
| 2003/0187062 A1 | 10/2003 | Zenoni et al. | |
| 2003/0199425 A1 | 10/2003 | Desai et al. | |
| 2003/0203033 A1* | 10/2003 | Dang et al. | 424/486 |
| 2003/0220354 A1 | 11/2003 | McClure et al. | |
| 2004/0033271 A1 | 2/2004 | Lederman | |
| 2004/0047835 A1* | 3/2004 | Bianco | 424/78.17 |
| 2004/0053946 A1 | 3/2004 | Lackey et al. | |
| 2004/0126400 A1* | 7/2004 | Iversen et al. | 424/400 |
| 2004/0143004 A1 | 7/2004 | Fargnoli et al. | |
| 2004/0167079 A1 | 8/2004 | Tidmarsh | |
| 2004/0248781 A1 | 12/2004 | Kerbel | |
| 2005/0000900 A1 | 1/2005 | Huang et al. | |
| 2005/0004002 A1 | 1/2005 | Desai et al. | |
| 2005/0032699 A1 | 2/2005 | Holash et al. | |
| 2005/0058684 A1 | 3/2005 | Shanley et al. | |
| 2005/0095267 A1 | 5/2005 | Campbell et al. | |
| 2005/0186208 A1 | 8/2005 | Fyfe et al. | |
| 2006/0003931 A1 | 1/2006 | Eigenbrot et al. | |
| 2006/0013819 A1 | 1/2006 | Kelsey | |
| 2006/0062821 A1 | 3/2006 | Simhambhatla et al. | |
| 2006/0073175 A1 | 4/2006 | Soon-Shiong et al. | |
| 2006/0083782 A1 | 4/2006 | Desai et al. | |
| 2006/0121119 A1 | 6/2006 | Zenoni et al. | |
| 2006/0165744 A1 | 7/2006 | Jamil et al. | |
| 2006/0199248 A1 | 9/2006 | Trieu et al. | |
| 2006/0257326 A1 | 11/2006 | Desai et al. | |
| 2007/0020337 A1 | 1/2007 | Zenoni et al. | |
| 2007/0082838 A1 | 4/2007 | De et al. | |
| 2007/0087022 A1 | 4/2007 | Desai et al. | |
| 2007/0092563 A1 | 4/2007 | Desai et al. | |
| 2007/0093547 A1 | 4/2007 | Desai et al. | |
| 2007/0116774 A1 | 5/2007 | Desai et al. | |
| 2007/0117133 A1 | 5/2007 | Trieu et al. | |
| 2007/0117744 A1 | 5/2007 | Desai et al. | |
| 2007/0117862 A1 | 5/2007 | Desai et al. | |
| 2007/0117863 A1 | 5/2007 | Desai et al. | |
| 2007/0128290 A1 | 6/2007 | Desai et al. | |
| 2007/0129448 A1 | 6/2007 | Desai et al. | |
| 2007/0166388 A1 | 7/2007 | Desai et al. | |
| 2007/0196361 A1 | 8/2007 | Soon-Shiong et al. | |
| 2007/0207196 A1 | 9/2007 | Zhang | |
| 2008/0045559 A1 | 2/2008 | Zhang et al. | |
| 2008/0063699 A1 | 3/2008 | Teifel et al. | |
| 2008/0085902 A1 | 4/2008 | Bold et al. | |
| 2008/0146598 A1 | 6/2008 | Bianco | |
| 2009/0018078 A1 | 1/2009 | Labhasetwar | |
| 2009/0047337 A1 | 2/2009 | Mescheder et al. | |
| 2009/0304805 A1 | 12/2009 | Desai et al. | |
| 2010/0035800 A1 | 2/2010 | Desai et al. | |
| 2010/0048499 A1 | 2/2010 | Desai et al. | |
| 2010/0112077 A1 | 5/2010 | Desai et al. | |
| 2010/0166869 A1 | 7/2010 | Desai et al. | |
| 2010/0183728 A1 | 7/2010 | Desai et al. | |
| 2010/0196490 A1 | 8/2010 | Desai et al. | |
| 2010/0215751 A1 | 8/2010 | Desai et al. | |
| 2010/0226996 A1 | 9/2010 | Desai et al. | |
| 2011/0052708 A1 | 3/2011 | Soon-Shiong et al. | |

FOREIGN PATENT DOCUMENTS

| | | | |
|---|---|---|---|
| EP | 0 584 001 A1 | | 2/1994 |
| WO | WO 98/14174 | * | 4/1988 |
| WO | WO-91/15193 A1 | | 10/1991 |
| WO | WO-94/18954 A1 | | 9/1994 |
| WO | WO-95/03036 A1 | | 2/1995 |
| WO | WO-98/14174 A1 | | 4/1998 |
| WO | WO-99/00113 A1 | | 1/1999 |
| WO | WO00/06152 | * | 2/2000 |
| WO | WO-00/06152 A1 | | 2/2000 |
| WO | WO 00/06152 | * | 10/2000 |
| WO | WO-00/64437 A1 | | 11/2000 |
| WO | WO-00/71079 A2 | | 11/2000 |
| WO | WO-00/71163 A1 | | 11/2000 |
| WO | WO-01/34174 A2 | | 5/2001 |
| WO | WO-01/34174 A3 | | 5/2001 |
| WO | WO-01/76567 A1 | | 10/2001 |
| WO | WO-01/89522 A1 | | 11/2001 |
| WO | WO-02/24179 A2 | | 3/2002 |
| WO | WO-02/24179 A3 | | 3/2002 |
| WO | WO-02/056912 A2 | | 7/2002 |
| WO | WO-02/056912 A3 | | 7/2002 |
| WO | WO-02/076459 A1 | | 10/2002 |
| WO | WO-02/087545 A1 | | 11/2002 |
| WO | WO-03/008665 A1 | | 1/2003 |
| WO | WO-03-096944 A1 | | 11/2003 |
| WO | WO-2004/017964 A1 | | 3/2004 |
| WO | WO-2004/052401 A2 | | 6/2004 |
| WO | WO-2004/052401 A3 | | 6/2004 |
| WO | WO-2005/000266 A2 | | 1/2005 |
| WO | WO-2005/000266 A3 | | 1/2005 |
| WO | WO-2005/000900 A1 | | 1/2005 |
| WO | WO-2005/039533 A1 | | 5/2005 |
| WO | WO-2005/117952 A2 | | 12/2005 |
| WO | WO-2005/117952 A3 | | 12/2005 |
| WO | WO-2005/117978 A2 | | 12/2005 |
| WO | WO-2005/117978 A3 | | 12/2005 |
| WO | WO-2005/117986 A2 | | 12/2005 |
| WO | WO-2005/117986 A3 | | 12/2005 |
| WO | WO-2006/089290 A1 | | 8/2006 |
| WO | WO-2006/117220 A1 | | 11/2006 |
| WO | WO-2006/117220 A2 | | 11/2006 |
| WO | WO-2006/117220 A3 | | 11/2006 |
| WO | WO-2006/124684 A2 | | 11/2006 |
| WO | WO-2006/124684 A3 | | 11/2006 |
| WO | WO-2007/117220 A3 | | 11/2006 |
| WO | WO-2007/027819 A2 | | 3/2007 |
| WO | WO-2007/027819 A3 | | 3/2007 |
| WO | WO-2007/027941 A2 | | 3/2007 |
| WO | WO-2007/027941 A3 | | 3/2007 |
| WO | WO-2007/059116 A2 | | 5/2007 |
| WO | WO-2007/059116 A3 | | 5/2007 |
| WO | WO-2007/107305 A2 | | 9/2007 |
| WO | WO2007/107305 A3 | | 9/2007 |
| WO | WO-2008/057562 A1 | | 5/2008 |

OTHER PUBLICATIONS

Bocci, G. et al. (Dec. 1, 2002). "Protracted Low-Dose Effects on Human Endothelial Cell Proliferation and Survival in Vitro reveal a Selective Antiangiogenic Window for Various Chemotherapeutic Drugs," *Cancer Res.* 62:6938-6943.

Bocci, G. et al. (Oct. 15, 2003). "Thrombospondin 1, a Mediator of the Antianggiogenic Effects of Low-dose Metronomic Chemotherapy," *PNAS USA* 100(22):12917-12922.

Bourgeois, H et al. (Jun. 2006). "Phase I-II Study of Pegylated Liposomal Doxorubicin Combined With Weekly Paclitaxel as First-Line Treatment in Patients with Metastatic Breast Cancer," *American Journal of Clinical Oncology* 29(3):267-275.

Carmeliet, P. et al. (Sep. 14, 2000). "Angiogenesis in Cancer and Other Diseases," *Nature* 407(6801):249-257.

Damascelli, B. et al. (Nov. 15, 2001). "Intraarterial Chemotherapy with Polyoxyethylated Castor Oil Free Pacitaxil, Incorporated in Albumin Nanoparticles (ABI-007)," *Cancer* 92(10):2592-2602.

Desai, N. et al. (Jul. 2003). "Oral Bioavailability of Paclitaxel in a Novel, Cremophor EL-free, Protein-based Nanoparticle Preparation," *Proceedings of the Amer. Assn. for Cancer Research* 44 2 :732 (Abstract No. 3673).

Ellerby, H. M. et al. (Sep. 1999). "Anti-Cancer Activity of Targeted Pro-Apoptotic Peptides," *Nat. Med.* 5(9)1032-1038.

Fleming, G.F. et al. (Jun. 1, 2004). "Phase III Trial of Doxorubicin Plus Cisplatin with or without Paclitaxel plus Filgrastim in Advanced Endometrial Carcinoma: a Gynecologic Oncology Group Study," *J. Clin. Oncol.* 22(11):2159-2166.

Fujimoto-Ouchi, K. et al. (Apr. 2001). "Schedule of Dependency of Antitumor Activity in Combination Therapy with Capecitabine/ 5'Deoxy-5-fluorouridine and Docetaxel in Breast Cancer Models," *Clin. Cancer Res.* 7:1079-1086.

Fulfaro F. et al. (Jul. 15, 2004). "Weekly Paclitaxel (T) and Pegylated Liposomal Doxorubicin (PLD) as First Line Treatment in Metastatic Breast Cancer (MBC) Patients," *J. Clin. Oncol.* 22(14S):53S (Abstract No. 704).

Gelderblom, H. et al. (Apr. 2002). "Influence of Cremophor EL on the Bioavailability of Interperitoneal Paclitaxel," *Clin. Cancer Res.* 8:1237-1241.

Gradishar, W. J. et al. (Nov. 1, 2005). "Phase III Trial of Nanoparticle Albumin-Bound Paclitaxel Compared with Polyethylated Castor Oil-Based Paclitaxel in Women With Breast Cancer," *J. Clin. Oncol.* 23(31):7794-7803.

Harries, M. et al. (Nov. 1, 2005). "Nanoparticle Albumin-Bound Paclitaxel for Metastatic Breast Cancer," *J. Clin. Oncol.* 23(31):7768-7771.

Hudis, C. et al. (Jan. 1999). "Sequential Dose-dense Doxorubicin, Paclitaxel, and Cyclophosphamide for Resectable High-risk Breast Cancer: Feasibility and Efficacy," *J. Clin. Oncol.* 17(1):93-100.

Hudis, C. (Aug. 20, 2005). "Testing Chemotherapy for Breast Cancer: Timing is Everything," *J. Clin. Oncol.* 23(24):5434-5436.

Ibrahim, N. K. et al. (Sep. 1, 2005). "Multicenter Phase II Trial of ABI-007, an Albumin-Bound Paclitaxel, in Women With Metastatic Breast Cancer," *J. Clin. Oncol.* 23(25):6019-6026.

International Search Report mailed Jul. 7, 2006 for PCT Application No. PCT/US2006/006167 filed on Feb. 21, 2006, four pages.

Jimenez, J.J. et al. (Jan. 15, 1992). "Protection from 1-α-D-Arabinofuranosylcytosine-Induced Alopecia by Epidermal Growth Factor and Fibroblast Growth Factor in the Rat Model," *Cancer Research* 52:413-415.

Jones, V. et al. (2000). "Phase II Study of Weekly Paclitaxel (Taxol) and Liposomal Doxorubicin (Doxil) in Patients with Locally Advanced and Metastatic Breast Cancer," *Proc. Amer. Soc. Clin. Oncol.* 19:116a (Abstract No. 451).

Kosmidis, P. et al. (Sep. 1, 2002). "Paclitaxel Plus Carboplatin Versus Gemcitabine Plus Paclitaxel in Advanced Non-small-cell Lung Cancer: A Phase III Randomized Trial," *J. Clin. Oncol.* 20(17):3578-3585.

Mavroudis, D. et al. (2002). "Phase I Study of Paclitaxel (Taxol) and Pegylated Liposomal Doxorubicin (Caelyx) Administered Every 2 Weeks in Patients with Advanced Solid Tumors," *Oncology* 62:216-222.

Modiano, M. et al. (1999). "Phase I Study of DOXIL® (Pegylated Liposomal Doxorubicin) Plus Escalating Doses of TAXOL® in the Treatment of Patients with Advanced Breast or Gynecologic Malignancies," *Proc. Amer. Soc. Clin. Oncol.* 18:220a (Abstract No. 848).

Moreno-Aspitia, A. et al. (2005). "Nanoparticle Albumin-bound Paclitaxel (ABI-007): a Newer Taxane Alternative in Breast Cancer," *Future Oncol.* 1(6):755-762.

Moreno-Aspitia, A. et al. (Oct. 2005). "North Central Cancer Treatment Group N0531: Phase II Trail of Weekly Albumin-bound Paclitaxel (ABI-007, Abraxane®) in Combination with Gemcitabine in Patients with Metastatic Breast Cancer," *Clinical Breast Cancer* 6(4):361-364.

Ng, S.S.W. et al. (Feb. 1, 2004). "Taxane-mediated Antiangiogenesis in Vitro: Influence of Formulation Vehicles and Binding Proteins," *Cancer Res.* 64:821-824.

Nyman, D.W. et al. (Nov. 1, 2005). "Phase I and Pharmacokinetics Trial of ABI-007, a Novel Nanoparticle Formulation of Paclitaxel in Patients with Advanced Nonhematologic Malignancies," *J. Clin. Oncol.* 23(31):7785-7793.

O'Reilly, M.S. et al. (Oct. 21, 1994). "Angiostatin: A Novel Angiogenesis Inhibitor That Mediates the Suppression of Metastases by a Lewis Lung Carcinoma," *Cell* 79:315-328.

O'Reilly, M.S. et al. (Jan. 24, 1997). "Endostatin: An Endogenous Inhibitor of Angiogenesis and Tumor Growth," *Cell* 88:277-285.

Robert, N. et al. (Dec. 2005). "Pilot Study of Dose-dense Doxorubicin Plus Cyclophosphamide Followed by Abi-007 in Patients with Early-Stage Breast Cancer," San Antonio Breast Cancer Symposium, San Antonio, TX, Dec. 8-11, 2005, two pp.

Roche Laboratories, Inc. (Apr. 2006). "Xeloda® (Capecitabine) Tablets Product Insert," 43 pp.

Romond, E.H. et al. (2005). "Combined Analysis of Nsabp-B31/Ncctg-N9381: Disease-Free and Overall Survival Data," Breast Cancer Update 4(6):15-19.

Sawada, N. et al. (Apr. 1998). "Induction of Thymidine Phosphorylase Activity and Enhancement of Capecitabine Efficacy by Taxol/Taxotere in Human Cancer Xenografts," *Clinical Cancer Res.* 494):1013-1019.

Schwonzen, M. et al. (2000). "Liposomal Doxorubicin and Weekly Paclitaxel in the Treatment of Metastatic Breast Cancer," *Anti-Cancer Drugs* 11:681-685.

Seidman, A.D. et al. (1993). "Taxol Plus Recombinant Human Granulocyte-Colony Stimulating Factor as Initial and as Salvage Chemotherapy for Metastatic Breast Cancer: A Preliminary Report," *J. of the National Cancer Institute Monographs* (15):171-175.

Shaked, Y. et al. (Jan. 2005). "Genetic Heterogeneity of the Vasculogenic Phenotype Parallels Angiogenesis: Implications for Cellular Surrogate Marker Analysis of Antiangiogenesis," *Cancer Cell* 7:101-111.

Sledge, G.W. et al. (Feb. 15, 2003). "Phase III Trial of Doxorubicin, Paclitaxel, and the Combination of Doxorubicin and Paclitaxel as Front-line Chemotherapy for Metastatic Breast Cancer: an Intergroup Trial (E1193)," *J. Clin. Oncol.*21(4):588-592.

U.S. Appl. No. 09/446,783, filed May 16, 2006 for Desai et al.
U.S. Appl. No. 09/937,840, filed Jan. 28, 2002 for Desai et al.
U.S. Appl. No. 11/514,030, filed Aug. 30, 2006 for Desai et al.
U.S. Appl. No. 11/544,242, filed Oct. 6, 2006 for Desai et al.
U.S. Appl. No. 11/594,417, filed Nov. 6, 2006 for Desai et al.

Zalcberg, J. et al. (May 1998). "Phase II Study of Docetaxel and Cisplaten in Advanced Non-small-cell Lung Cancer," *J. of Clin. Onc.* 16(5):1948-1953.

U.S. Appl. No. 09/446,783, filed May 16, 2000, Desai et al.
U.S. Appl. No. 11/553,339, filed Oct. 26, 2006, Desai et al.

O'Shaughnessy, J. A. et al. (2004). "Weekly Nanoparticle Albumin Paclitaxel (Abraxane) Results in Long-Term Disease Control in Patients With Taxane-Refractory Metastatic Breast Cancer," *Breast Cancer Research and Treatment, 27th Annual Charles A. Coltman San Antonio Breast Cancer Symposium*, Texas, USA, Dec. 8-11, 2004, 88(1):S65, Abstract No. 1070.

Stinchcombe, T. E. et al. (2005). "Preliminary Results of Phase I Trial of Carboplatin (CP) in Combination with ABI-007 Administered Weekly or Every 3 Weeks in Patients (pts) With Solid Tumors," *Breast Cancer Research and Treatment, 28th Annual San Antonio Breast Cancer Symposium*, Texas, USA, Dec. 8-11, 2005, 94(1):571, Abstract No. 1092.

Allerton, J.P. at al. (Jun. 20, 2006). "A Phase II Evaluation of the Combination of Paclitaxel Protein-bound and Carboplatin in the First-line Treatment of Advanced Non-small Cell Lung Cancer (NSCLC)," Abstract, 2006 ASCO Annual Meeting Proceedings, Part 1, *J. Clin. Oncol.* 24(18 Suppl.): Abstract No. 7127, located at http://www.asco.org/portal/site/ASCO/template.RAW/menuitem...>, last visited on Oct. 1, 2008, two pages.

Du Bois, a. at al. (1997). "Phase I/II Study of the Combination of Carboplatin and Paclitaxel as First-line Chemotherapy in Patients with Advanced Epithelial Ovarian Cancer," *Ann. Oncol.* 8:355-361.

Hawkins, M.J. et al. (Jun. 20, 2006). "Dose Escalation Study of *Nab*-Paclitaxel Followed by Carboplatin as First Line Therapy in Advanced Non-small Cell Lung Cancer (NSCLC)," Abstract, 2006 ASCO Annual Meeting Proceedings, Part 1, *J. Clin. Oncol.* 24(18 Suppl.): Abstract No. 7132, located at http://www.asco.org/portal/site/ASCO/template.RAW/menuitem....>, last visited on Oct. 1, 2008, two pages.

Hawkins, M.J. et al. (Jun. 20, 2007). "Study of Three Weekly Nab-Paclitaxel Regimens in Combination with Carboplatin as First-line Therapy in Advanced Non-small Cell Lung Cancer (NSCLC)," Abstract, 2007 ASCO Annual Meeting Proceedings, Part 1, *J. Clin. Oncol.* 25(18 Suppl.): Abstract No. 7659, located at http://www.asco.org/portal/site/ASCO/template.RAW/menuitem....>, last visited on Oct. 1, 2008, two pages.

Hawkins, M.J. et al. (Sep. 2007). "High-dose 130-nanometer Albumin-bound Paclitaxel in Combination with Carboplatin as First-line Therapy in Advanced Non-small Cell Lung Cancer," Poster No. 6563, *Eur. J. Cancer Supplements* 5(4):376-377.

International Search Report mailed on Mar. 17, 2008, for PCT Application No. PCT/US2007/023446, filed on Nov. 6, 2007, five pages.

Johnson, J.H. et al. (1996). "Paclitaxel Plus Carboplatin in Advanced Non-small-cell Lung Cancer: A Phase II Trial," *J. Clin. Oncol.* 14:2054-2060.

Langer, C.J. et al. (Aug. 1995). "Paclitaxel by 24- or 1-Hour Infusion in Combination with Carboplatin in Advanced Non-Small Cell Lung Cancer: The Fox Chase Cancer Center Experience," *Semin. Oncol.* 22(4-Suppl. 9):18-29.

Langer, C.J. et al. (Dec. 1996). "Combination Paclitaxel (1-Hour) and Carboplatin (AUC 7.5) in Advanced Non-Small Cell Lung Cancer: A Phase II Study by the Fox Chase Cancer Center Network," *Semin. Oncol.* 23(6-Suppl. 16):35-41.

Paccagnella, A. et al. (Dec. 1996). "Paclitaxel and Carboplatin: A Phase I Study in Advanced Non-Small Cell Lung Cancer," *Semin. Oncol.* 23(6-Suppl. 16):76-79.

Reynolds, C. et al. (Jun. 20, 2007). "An Open-label, Phase II Trial of Nanoparticle Albumin Bound Paclitaxel (Nab-paclitaxel), Carboplatin, and Bevacizumab in First-line Patients with Advanced Non-squamous Non-small cell Lung Cancer (NSCLC)," Abstract, 2007 ASCO Annual Meeting Proceedings, Part 1, *J. Clin. Oncol.* 25(18 Suppl.): Abstract No. 7610, located at http://www.asco.org/portal/site/ASCO/template.RAW/menuitem....>, last visited on Oct. 1, 2008, two pages.

Rosell, R. et al. (2002). "Phase III Randomised Trial Compairng Paclitaxel/Carboplatin with Paclitaxel/Cisplatin in Patients with Advanced Non-small-cell Lung Cancer: A Cooperative Multinational Trial," *Ann. Oncol.* 13:1539-1549.

Written Opinion mailed on Mar. 17, 2008, for PCT Application No. PCT/US2007/023446, filed on Nov. 6, 2007, six pages.

U.S. Appl. No. 11/833,179, filed Aug. 2, 2007, for Desai et al.
U.S. Appl. No. 11/833,188, filed Aug. 2, 2007, for Desai et al.
U.S. Appl. No. 11/880,218, filed Jul. 19, 2007, for Desai et al.
U.S. Appl. No. 11/880,314, filed Jul. 20, 2007 for Desai et al.
U.S. Appl. No. 11/890,041, filed Aug. 3, 2007, for Desai et al.
U.S. Appl. No. 11/890,197, filed Aug. 3, 2007, for Desai et al.
U.S. Appl. No. 11/890,599, filed Aug. 6, 2007, for Desai et al.
U.S. Appl. No. 11/890,603, filed Aug. 6, 2007, for Desai et al.
U.S. Appl. No. 11/890,819, filed Aug. 7, 2007, for Desai et al.
U.S. Appl. No. 11/897,724, filed Aug. 31, 2007, for Desai et al.
U.S. Appl. No. 12/051,782, filed Mar. 19, 2008, for Desai et al.
U.S. Appl. No. 12/240,893, filed Sep. 29, 2008, for Desai et al.

Belani, C.P. et al. (Aug. 1, 2003). "Multicenter, Randomized Trial for Stage IIIB or IV Non-Small-Cell Lung Cancer Using Weekly Paclitaxel and Carboplatin Followed by Maintenance Weekly Paclitaxel or Observation," *J. Clin. Oncol.* 21(15):2933-2939.

Schiller, J.H. et al., (Jan. 10, 2002). "Comparison of Four Chemotherapy Regimens for Advanced Non-Small-Cell Lung Cancer," *New England J. Med.* 346(2):92-98.

Schilsky, R.L. et al. (Jan. 15, 2002). "Dose-Escalating Study of Capecitabine Plus Gemcitabine Combination Therapy in Patients with Advanced Cancer," *J. Clin. Oncol.* 20(2):582-587.

U.S. Appl. No. 12/271,748, filed Nov. 14, 2008, for Desai et al.
U.S. Appl. No. 12/331,924, filed Dec. 10, 2008, for Desai et al.
U.S. Appl. No. 12/334,115, filed Dec. 12, 2008, for Desai et al.
U.S. Appl. No. 12/402,358, filed Mar. 11, 2009, for Desai et al.
U.S. Appl. No. 12/422,011, filed Apr. 10, 2009, for Desai et al.
U.S. Appl. No. 12/422,192, filed Apr. 10, 2009, for Desai et al.
U.S. Appl. No. 12/474,218, filed May 28, 2009, for Desai et al.
U.S. Appl. No. 12/479,710, filed Jun. 5, 2009, for Desai et al.
U.S. Appl. No. 12/513,843, filed May 6, 2009, for Desai et al.
U.S. Appl. No. 12/519,126, filed Jun. 12, 2009 for Desai et al.

Leong, S.-S. et al. (Feb. 1, 2005, E-pub. Dec. 20, 2004). "Paclitaxel, Carboplatin, and Gemcitabine in Metastatic Nasopharyngeal Carcinona: A Phase II Trial Using a Triplet Combination," *Cancer* 103(3):569-575.

U.S. Appl. No. 13/038,287, filed Mar. 1, 2011, for Desai et al.
U.S. Appl. No. 13/073,824, filed Mar. 28, 2011, for Desai et al.
U.S. Appl. No. 13/073,861, filed Mar. 28, 2011, for Desai et al.
U.S. Appl. No. 12/713,092, filed Feb. 25, 2010 for Soon-Shiong et al.
U.S. Appl. No. 12/761,292, filed Apr. 15, 2010, for Desai et al.
U.S. Appl. No. 12/818,099, filed Jun. 17, 2010 for De et al.
U.S. Appl. No. 12/824,014, filed Jun. 25, 2010 for Desai et al.
U.S. Appl. No. 12/874,965, filed Sep. 2, 2010, for De et al.
U.S. Appl. No. 12/832,876, filed Jul. 8, 2010, for Desai et al.
U.S. Appl. No. 61/318,774, filed Mar. 29, 2010, for Desai et al.
U.S. Appl. No. 61/318,777, filed Mar. 29, 2010, for Desai et al.

Final Office Action issued Dec. 24, 2009, for U.S. Appl. No. 09/847,945, filed May 2, 2001, 34 pages.
Final Office Action issued Apr. 14, 2009, for U.S. Appl. No. 09/847,945, filed May 2, 2001, 31 pages.
Non Final Office Action issued Jul. 11, 2008, for U.S. Appl. No. 09/847,945, filed May 2, 2001, 25 pages.
Final Office Action issued Nov. 9, 2007, for U.S. Appl. No. 09/847,945, filed May 2, 2001, 20 pages.
Non Final Office Action issued Aug. 17, 2009, for U.S. Appl. No. 11/594,417, filed Nov. 6, 2006, 16 pages.
Written Opinion mailed on Jul. 7, 2006 for PCT Application No. PCT/US2006/006167 filed on Feb. 21, 2006, 7 pages.

Abraxis Bioscience, Inc. (Mar. 17, 2010). "ABRAXANE Meets Primary Endpoint in Phase 3 Trial for Advanced Non-Small Cell Lung Cancer," Press Release located at http://www.biospace.com/news_print.aspx?NewsEntityId=174173. last visited May 3, 2010, 3 pages total.

Albain, K. S. et al. (Sep. 1991). "Survival Determinants in Extensive-Stage Non-Small-Cell Lung Cancer: The Southwest Oncology Group Experience," *J. Clin. Oncol.* 9(9):1618-1626.

Alberola, V. et al. (Sep. 1, 2003). "Cisplatin Plus Gemcitabine versus a Cisplatin-Based Triplet Versus Nonplatinum Sequential Doublets in Advanced Non-Small-Cell Lung Cancer: A Spanish Lung Cancer Group Phase III Randomized Trial," *J. Clin. Oncol.* 21(17)3207-3213.

American Cancer Society, (2009). "Cancer Facts and Figures," located at http://www.cancer.org/downloads/STT/500809web.pdf, pp. 1-72.

Belani, C. P. et al. (Jan. 20, 2008). "Randomized, Phase III Study of Weekly Paclitaxel in Combination With Carboplatin Versus Standard Every-3-Weeks Administration of Carboplatin and Paclitaxel for Patients With Previously Untreated Advanced Non-Small-Cell Lung Cancer," *J. Clin. Oncol.* 26(3):468-473.

Bonomi, P. D. et al. (Nov. 1989). "Combination Chemotherapy Versus Single Agents Followed by Combination Chemotherapy in Stage IV Non-Small-Cell Lung Cancer: A Study of the Eastern Cooperative Oncology Group," *J. Clin Oncol.* 7(11):1602-1613.

Bristol-Myers Squibb Company (Rev Jul. 2007). "TAXOL® (Paclitaxel) Injection, (Patient Information Included)," located at http://packageinserts.bms.com/pi/pi_taxol.pdf, last visited May 6, 2010, 55 pages.

Bunn, P. A. Jr. (Aug. 1989). "The Expanding Role of Cisplatin in the Treatment of Non-Small-Cell Lung Cancer," *Semin. Oncol.* 16(4)(Suppl. 6):10-21.

Cerny, T. et al. (1994). "Docetaxel (Taxotere™) is Active in Non-Small-Cell Lung Cancer: A Phase II Trial of the EORTC Early Clinical Trials Group (ECTG)," *Br. J. Cancer* 70:384-387.

Crinò, L. et al. (Nov. 1999). "Gemcitabine and Cisplatin versus Mitomycin, Ifosfamide, and Cisplatin in Advanced Non-Small-Cell Lung Cancer: A Randomized Phase III Study of the Italian Lung Cancer Project," *J. Clin. Oncol.* 17(11):3522-3530.

Damascelli, B. et al. (Jul. 2003). "A Novel Intraarterial Chemotherapy Using Paclitaxel in Albumin Nanoparticles to Treat Advanced Squamous Cell Carcinoma of the Tongue: Preliminary Findings," *AJR* 181:253-260.

Desai, N. et al. (Feb. 15, 2006). "Increased Antitumor Activity, Intratumor Paclitaxel Concentrations, and Endothelial Cell Transport of Cremophor-Free, Albumin-Bound Paclitaxel, ABI-007, Compared with Cremophor-Based Paclitaxel,"*Clin. Cancer Res.* 12(4):1317-1324.

Depierre, A. et al. (Mar. 1988). "Phase II Study of Navelbine (NVB) in Non Small Cell Lung Cancer (NSCLC)," *Proc. Am. Soc. Clin. Oncol*, 24th Annual Meeting of the American Society of Clinical Oncology (ASCO), May 22-24, 1988, Proceedings, New Orleans, Louisiana, vol. 7, p. 201, Abstract No. 778.

Edge, S. B. (eds) et al. (2010). Lung: Carcinoid Tumors are Included. Sarcomas and Other Rare Tumors are not included), Chapter 25 in *AJCC Cancer Staging Manual*, Seventh Edition, American Joint Committee on Cancer, Springer, Chicago, IL, pp. 253-270.

Fossella, F. V. et al. (Mar. 1995). "Phase II Study of Docetaxel for Advanced or Metastatic Platinum-Refractory Non-Small-Cell Lung Cancer," *J. Clin. Oncol.* 13(3):645-651.

Fossella, F. et al. (Aug. 15, 2003). "Randomized, Multinational, Phase III Study of Docetaxel Plus Platinum Combinations Versus Vinorelbine Plus Cisplatin for Advanced Non-Small-Cell Lung Cancer: the TAX 326 Study Group," *J. Clin. Oncol.* 21(16):3016-3024.

Gatzemeier, U. et al. (1995). "Phase II Study with Paclitaxel for the Treatment of Advanced Inoperable Non-Small Cell Lung Cancer," *Lung Cancer* 12(Suppl 2):S101-5106.

Gatzemeier, U. et al. (Oct. 1, 2000). "Phase III Comparative Study of High-Dose Cisplatin versus a Combination of Paclitaxel and Cisplatin in Patients with Advanced Non-Small-Cell Lung Cancer," *J. Clin. Oncol.* 18(19):3390-3399.

Gelderblom, H. et al. (2001). "Cremophor EL: The Drawbacks and Advantages of Vehicle Selection for Drug Formulation," *Eur. J. Cancer* 37:1590-1598.

Green, M. R. et al. (Aug. 2006, e-pub. Jun. 1, 2006). "Abraxane® A Novel Cremophor-Free, Albumin-Bound Particle Form of Paclitaxel for the Treatment of Advanced Non-Small-Cell Lung Cancer," *Ann. Oncol.* 17(8):1263-1268.

Grilli, R. et al. (Oct. 1993). "Chemotherapy for Advanced Non-Small-Cell Lung Cancer: How Much Benefit is Enough?" *J. Clin. Oncol.* 11(10):1866-1872.

Hainsworth, J. D. et al. (Jul. 1995). "Paclitaxel by 1-Hour Infusion: An Active Drug in Metastatic Non-Small-Cell Lung Cancer," *J. Clin. Oncol.* 13(7):1609-1614.

Herbst, R. S. et al. (Mar. 1, 2004). "Gefitinib in Combination with Paclitaxel and Carboplatin in Advanced Non-Small-Cell Lung Cancer: A Phase III Trial—INTACT 2," *J. Clin. Oncol.* 22(5):785-794.

Ibrahim, N. K. et al. (May 2002). "Phase I and Pharmacokinetic Study of ABI-007, a Cremophor-Free, Protein-Stabilized, Nanoparticle Formulation of Paclitaxel," *Clinical Cancer Research* 8:1038-1044.

Jafar, N. et al. (Apr. 19, 2010). "Caveolin-1 Inhibits Survivin and Increases Sensitivity to Paclitaxel in Breast Cancer Cells," AACR 101$^{st}$ Annual Meeting 2010, Meeting held on Monday, Apr. 19, 2010, in Washington D.C., Poster Section 23, Poster Board No. 4, Abstract 2547, one page.

Jones, C. M. et al. (Oct. 18, 2007). "Targeted Therapies for NSCLC," US Pharmacist, article located at http://www.uspharmacist.com/content/t/oncology/c/10219/, last visited Nov. 11, 2010, 9 pages.

Kelly, K. et al. (Jul. 1, 2001). "Randomized Phase III Trial of Paclitaxel Plus Carboplatin Versus Vinorelbine Plus Cisplatin in the Treatment of Patients with Advanced Non-Small-Cell Lung Cancer: A Southwest Oncology Group Trial," *J. Clin. Oncol.* 19(13):3210-3218.

Kim, Y.-N. et al. (2002). "Caveolin-1 Phosphorylation in Human Squamous and Epidermoid Carcinoma Cells: Dependence on ErbB1 Expression and Src Activation," *Exp.Cell Res.* 280:134-147.

Kolodgie, F. D. et al. (Sep. 3, 2002). "Sustained Reduction of in-Stent Neointimal Growth with the Use of a Novel Systemic Nanoparticle Paclitaxel," *Circulation* 106(10):1195-1198.

Kondrateva, A. P. (2001). The Combination of Radiation and Drug Therapies for the Organ Safe Treating of Malignant Tumours, *Modern Oncology* 3(3), located at http://www.consilium-medicum.com/magazines/cm/pediatrics/article/8403, in Russian, with English translation (author translated as A. P. Kondratieff) (from translategoogle.com), 6 pages total.

Langer, C. J. et al. (Jun. 2008). "Phase III Trial Comparing Paclitaxel Poliglumex (CT-2103, PPX) in Combination with Carboplatin Versus Standard Paclitaxel and Carboplatin in the Treatment of PS 2 Patients with Chemotherapy-Naïve Advanced Non-Small Cell Lung Cancer," *J. Thorac. Oncol.* 3(6):623-630.

Le Chevalier, T. et al. (Feb. 1994). "Randomized Study of Vinorelbine and Cisplatin versus Vindesine and Cisplatin versus Vinorelbine Alone in Advanced Non-Small-Cell Lung Cancer: Results of a European Multicenter Trial Including 612 Patients," *J. Clin. Oncol.* 12(2):360-367.

Li, C. et al. (Jun. 1, 1998). "Complete Regression of Well-Established Tumors Using a Novel Water-Soluble Poly(L-Glutamic Acid)-Paclitaxel Conjugate," *Cancer Research* 58:2404-2409.

Li, C. et al. (May 22, 2008). "Polymer-Drug Conjugates: Recent Development in Clinical Oncology," *Adv. Drug Deliv. Rev.* 60(8):886-898, 24 pages.

Lilenbaum, R. C. et al. (2002). "Single-Agent (SA) Versus Combination Chemotherapy (CC) in Advanced Non-Small Cell Lung Cancer (NSCLC): A CALGB Randomized Trial of Efficacy, Quality of Life (QOL), and Cost-Effectiveness," *Proc. Am. Soc. Clin. Oncol.*, presented at 2002 Annual Meeting of the American Society of Clinical Oncology (ASCO), Jun. 2002, vol. 21, Abstract No. 2.

Lynch, T. J. et al. (2005). "Optimizing Chemotherapy and Targeted Agent Combinations in NSCLC," *Lung Cancer* 50 (Suppl. 2):S25-S32.

Lynch, T. J. et al. (Feb. 20, 2010). "Cetuximab and First-Line Taxane/Carboplatin Chemotherapy in Advanced Non-Small-Cell Lung Cancer: Results of the Randomized Multicenter Phase III Trial BMS099," *J. Clin. Oncol.* 28(6):911-917.

Micha, J. P. et al. (Feb. 2006, e-pub Oct. 14 2005). "Abraxane in the Treatment of Ovarian Cancer: the Absence of Hypersensitivity Reactions," *Gynecol Oncol* 100(2):437-438, 15 pages.

Novelos Therapeutics, Inc. (2010). "Nov-002, Cancer," located at http://www.novelos.com/html/our_products/BAM_002.htm, last visited May 6, 2010, 4 pages.

Onn, A. et al. (2004). "Treatment of Non-Small-Cell Lung Cancer: A Perspective on the Recent Advances and the Experience with Gefitinib," *Br. J. Cancer* 91(Suppl 2):S11-S17.

Pectasides, D. et al. (2005). "Comparison of Docetaxel and Docetaxel-Irinotecan Combination as Second-Line Chemotherapy in Advanced Non-Small-Cell Lung Cancer: A Randomized Phase II Trial," *Annals of Oncology* 16:294-299.

Pirker, R. et al. (May 2, 2009). "Cetuximab Plus Chemotherapy in Patients with Advanced Non-Small-Cell Lung Cancer (FLEX): An Open-Label Randomised Phase III Trial," *Lancet* 373:1525-1531.

Reynolds, C. et al. (Dec. 2009). "Phase II Trial of Nanoparticle Albumin-Bound Paclitaxel, Carboplatin, and Bevacizumab in First-Line Patients with Advanced Nonsquamous Non-Small Cell Lung Cancer," *J. Thorac. Oncol.* 4(12):1537-1543.

Rizvi, N. A. et al. (Feb. 1, 2008). "Phase I/II Trial of Weekly Intravenous 130-nm Albumin-Bound Paclitaxel as Initial Chemotherapy in Patients with Stage IV Non-Small-Cell Lung Cancer," *J. Clin. Oncol.* 26(4):639-643.

Roe, S. M. et al. (Jan. 28, 1999, e-pub. Jan. 1, 1999). "Structural Basis for Inhibition of the Hsp90 Molecular Chaperone by the Antitumor Antibiotics Radicicol and Geldanamycin," *J. Med. Chem.* 42(2)260-266.

Sandler, A. B. et al. (Jan. 2000). "Phase III Trial of Gemcitabine Plus Cisplatin Versus Cisplatin Alone in Patients with Locally Advanced or Metastatic Non-Small-Cell Lung Cancer," *J. Clin. Oncol.* 18(1):122-130.

Sandler, A. et al. (Dec. 14, 2006). "Paclitaxel-Carboplatin Alone or with Bevacizumab for Non-Small-Cell Lung Cancer," *New Eng. J. Med.* 355(24):2542-2550.

Scagliotti, G. V. et al. (Nov. 1, 2002). "Phase III Randomized Trial Comparing Three Platinum-Based Doublets in Advanced Non-Small-Cell Lung Cancer," *J. Clin. Oncol.* 20:4285-4291.

Scagliotti, G. V. et al. (Jul. 20, 2008). "Phase III Study Comparing Cisplatin Plus Gemcitabine with Cisplatin Plus Pemetrexed in Chemotherapy-Naïve Patients with Advanced-Stage Non-Small-Cell Lung Cancer," *J. Clin. Oncol.* 26(21):3543-3551.

Schiller, J. H. et al. (Jan. 10, 2002). "Comparison of Four Chemotherapy Regimens for Advanced Non-Small-Cell Lung Cancer," *N. Engl. J. Med.* 346(2):92-98.

Shepherd, F. A. (Dec. 1995). "Phase II Trials of Single-Agent Activity of Gemcitabine in Patients with Advanced Non-Small Cell Lung Cancer: An Overview," *Anti-Cancer Drugs* 6(Suppl 6):19-25.

Socinski, M. (Oct. 2006). "Update on Nanoparticle Albumin-Bound Paclitaxel," *Clinical Advances in Hematology & Oncology* 4(10):745-746.

Socinski, M. A. et al. (Aug. 1, 2009). "PD3.3.4—Retrospective Analysis of a Phase II Study of *nab*-Paclitaxel plus Carboplatin in Advanced NSCLC: Response Based on Histology," *NSCLC—Advanced Disease I, International Association for the Study of Lung Cancer*, WCLC 13th World Conference on Lung Cancer, 2 pages.

Socinski, M. A. et al. (2010). "Results of a Randomized, Phase III Trial of Nab-Paclitaxel (nab-P) and Carboplatin (C) Compared with Cremophor-Based Paclitaxel (P) and Carboplatin as First-Line Therapy in Advanced Non-Small Cell Lung Cancer (NSCLC)," Abstract for 2010 American Society of Clinical Oncology Annual Meeting, Abstract Control No. 52889, located at http://www.asco.org/ASCOv2/Meetings/Abstracts?vmview=abst_detail_view&confID=74&abstractID=52889, last visited Oct. 10, 2010, *J. Clin. Oncol.* 28:18s (suppl. Abstr. LBA7511), 3 pages.

Socinski, M. A. et al. (Jun. 2010). "A Dose Finding Study of Weekly and Every-3-Week nab-Paclitaxel Followed by Carboplatin as First-Line Therapy in Patients with Advanced Non-Small Cell Lung Cancer," *J. Thorac. Oncol.* 5(6):852-861.

Sorensen, J. B. et al. (Mar. 1987). "Vinca Alkaloids in the Treatment of Non-Small Cell Lung Cancer," *Cancer Treatment Reviews* 14(1):29-51.

Sørensen, J. B. (1995). "Gemcitabine in Non-Small Cell Lung Cancer," *Lung Cancer* 12 (Suppl. 1):5173-5175.

Sparreboom, A. et al. (Jun. 1, 2005). "Comparative Preclinical and Clinical Pharmacokinetics of a Cremophor-Free, Nanoparticle Albumin-Bound Paclitaxel (ABI-007) and Paclitaxel Formulated in Cremophor (Taxol)," *Clin. Cancer Res.* 11(11):4136-4143.

Stinchcombe, T. E. et al. (Oct. 2007). "Phase I and Pharmacokinetic Trial of Carboplatin and Albumin-Bound Paclitaxel, ABI-007 (Abraxane) on Three Treatment Schedules in Patients with Solid Tumors," *Cancer Chemotherap. Pharmacol.* 60(5):759-766, 15 pages.

Stroyakovsky, D. L. et al. (Aug. 1, 2009). "PD3.4.1—Weekly and Every-3-Week Nab-Paclitaxel Followed by Carboplatin as First-Line Therapy is Effective in Patients With Advanced Non-Small Cell Lung Cancer: Final Results of a Phase II Study," NSCLC—Advanced Disease I, Poster Discussion, 13th World Conference on Lung Cancer, located at www.2009worldlungcancer.org, http://abstracts/webges.com/itinerary.php?i=1&abstract=2157&keyword=paclitaxel, last visited on Nov. 11, 2010, 2 pages.

Ten Tije, A. J. et al. (2003). "Pharmacological Effects of Formulation Vehicles, Implications for Cancer Chemotherapy," *Clin. Pharmacokinet.* 42(7):665-685.

Wozniak, A. J. et al. (Jul. 1998). "Randomized Trial Comparing Cisplatin with Cisplatin plus Vinorelbine in the Treatment of Advanced Non-Small-Cell Lung Cancer: A Southwest Oncology Group Study," *J. Clin. Oncol.* 16(7):2459-2465.

Yoo, S.-H. et al. (2003). "Expression of Caveolin-1 is Associated with Poor Prognosis of Patients with Squamous Cell Carcinoma of the Lung," *Lung Cancer* 42:195-202.

Stroyakovsky, D. L. et al. (2009). "Weekly and Every-3-Week *nab*—Paclitaxel Followed by Carboplatin as First-Line Therapy is Effective in Patients With Advanced Non-Small Cell Lung Cancer: Final Results of a Phase II Study," *IASLC, 13th World Conference on Lung Cancer*, San Francisco, CA, Jul. 31-Aug. 4, 2009, Poster Discussion # PD3.4.1, one page.

Socinski, M. A. et al. (2009). "Retrospective Analysis of a Phase II Study of *nab*-Paclitaxel Plus Carboplatin in Advanced NSCLC, Response Based on Histology," *IASLC, 13hu th World Conference on Lung Cancer*, San Francisco, CA, Jul. 31-Aug. 4, 2009, Poster Discussion # PD3.3.4, one page.

\* cited by examiner

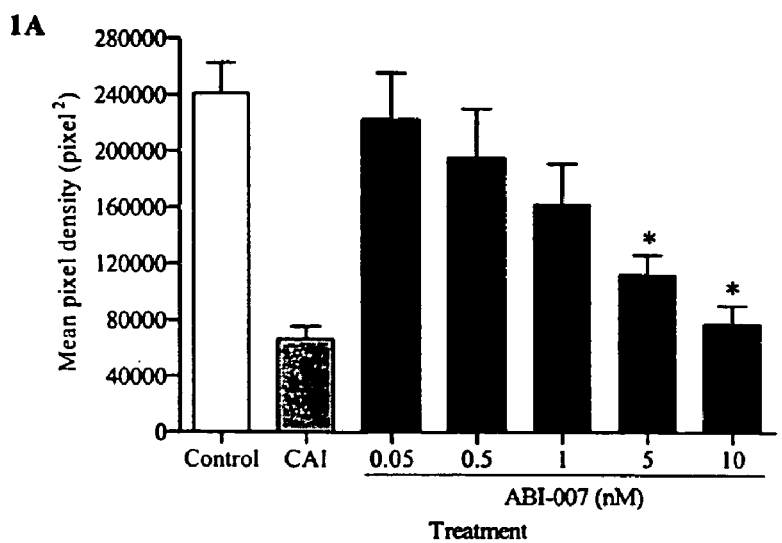
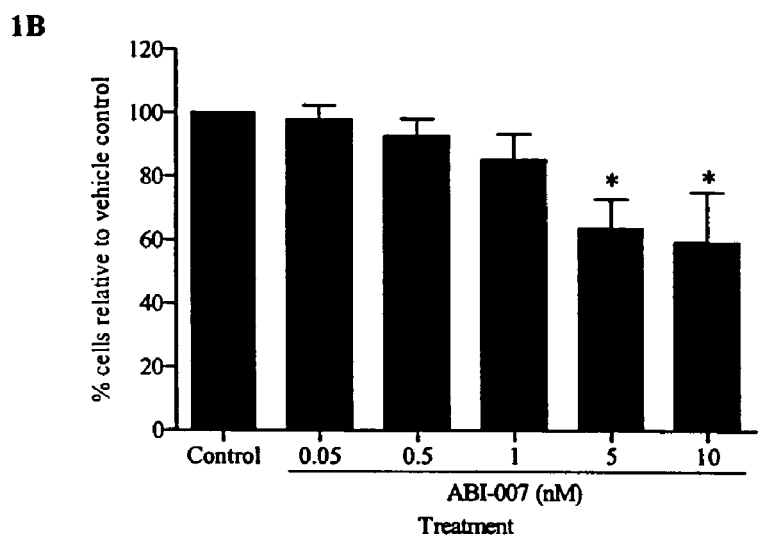
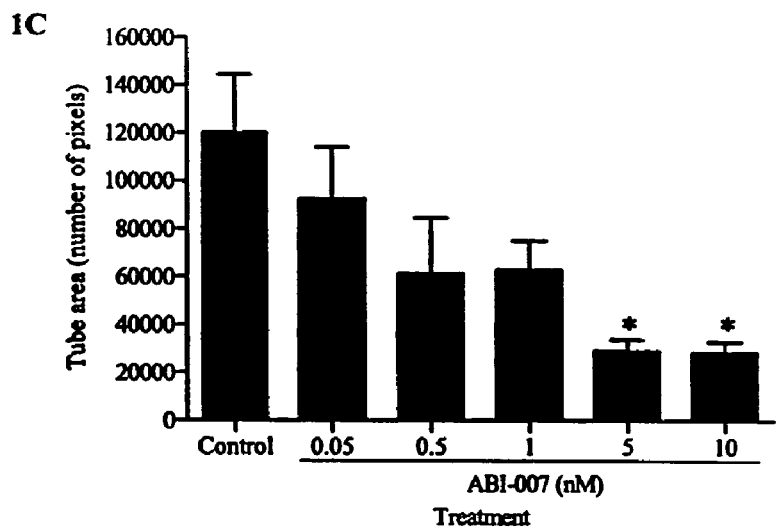
Fig. 1

FIG. 7
7A
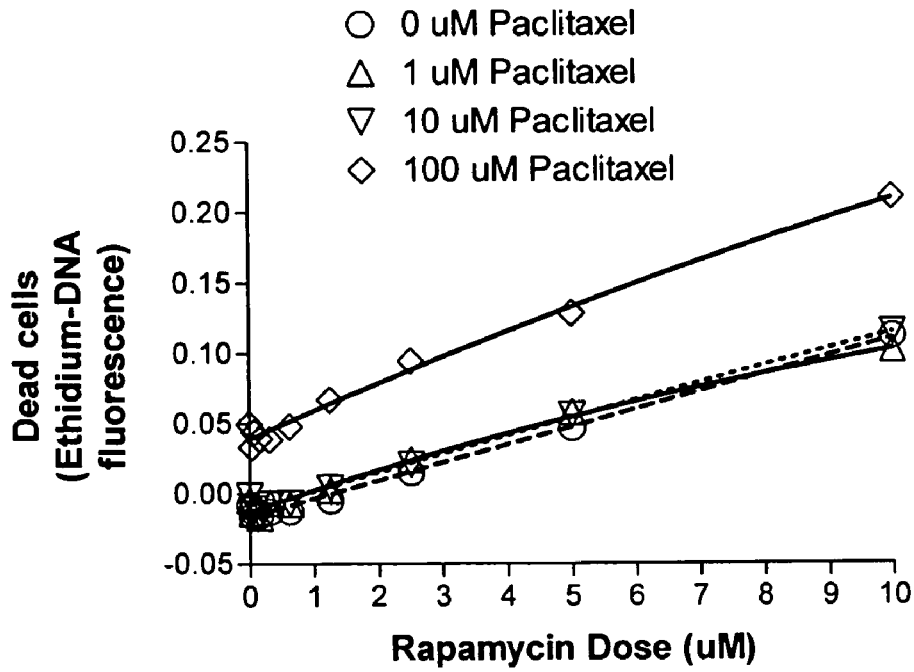
7B
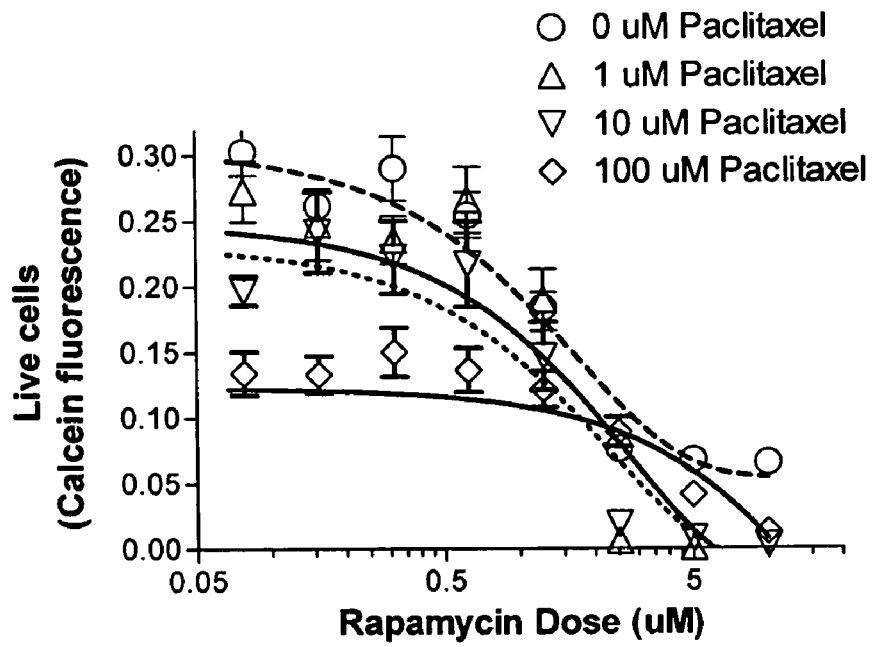

COMBINATIONS AND MODES OF ADMINISTRATION OF THERAPEUTIC AGENTS AND COMBINATION THERAPY

RELATED APPLICATIONS

This application claims priority benefit to provisional application 60/654,245, filed on Feb. 18, 2005, which is incorporated by reference herein in its entirety.

TECHNICAL FIELD

The present invention relates to methods and compositions for the treatment of proliferative diseases comprising the administration of a combination of a taxane and at least one other and other therapeutic agents, as well as other treatment modalities useful in the treatment of proliferative diseases. In particular, the invention relates to the use of nanoparticles comprising paclitaxel and albumin (such as Abraxane™) in combination with other chemotherapeutic agents or radiation, which may be used for the treatment of cancer.

BACKGROUND

The failure of a significant number of tumors to respond to drug and/or radiation therapy is a serious problem in the treatment of cancer. In fact, this is one of the main reasons why many of the most prevalent forms of human cancer still resist effective chemotherapeutic intervention, despite certain advances in the field of chemotherapy.

Cancer is now primarily treated with one or a combination of three types of therapies: surgery, radiation, and chemotherapy. Surgery is a traditional approach in which all or part of a tumor is removed from the body. Surgery generally is only effective for treating the earlier stages of cancer. While surgery is sometimes effective in removing tumors located at certain sites, for example, in the breast, colon, and skin, it cannot be used in the treatment of tumors located in other areas, inaccessible to surgeons, nor in the treatment of disseminated neoplastic conditions such as leukemia. For more than 50% of cancer individuals, by the time they are diagnosed they are no longer candidates for effective surgical treatment. Surgical procedures may increase tumor metastases through blood circulation during surgery. Most of cancer individuals do not die from the cancer at the time of diagnosis or surgery, but rather die from the metastasis and the recurrence of the cancer.

Other therapies are also often ineffective. Radiation therapy is only effective for individuals who present with clinically localized disease at early and middle stages of cancer, and is not effective for the late stages of cancer with metastasis. Radiation is generally applied to a defined area of the subject's body which contains abnormal proliferative tissue, in order to maximize the dose absorbed by the abnormal tissue and minimize the dose absorbed by the nearby normal tissue. However, it is difficult (if not impossible) to selectively administer therapeutic radiation to the abnormal tissue. Thus, normal tissue proximate to the abnormal tissue is also exposed to potentially damaging doses of radiation throughout the course of treatment. There are also some treatments that require exposure of the subject's entire body to the radiation, in a procedure called "total body irradiation", or "TBI." The efficacy of radiotherapeutic techniques in destroying abnormal proliferative cells is therefore balanced by associated cytotoxic effects on nearby normal cells. Because of this, radiotherapy techniques have an inherently narrow therapeutic index which results in the inadequate treatment of most tumors. Even the best radiotherapeutic techniques may result in incomplete tumor reduction, tumor recurrence, increasing tumor burden, and induction of radiation resistant tumors.

Chemotherapy involves the disruption of cell replication or cell metabolism. Chemotherapy can be effective, but there are severe side effects, e.g., vomiting, low white blood cells (WBC), loss of hair, loss of weight and other toxic effects. Because of the extremely toxic side effects, many cancer individuals cannot successfully finish a complete chemotherapy regime. Chemotherapy-induced side effects significantly impact the quality of life of the individual and may dramatically influence individual compliance with treatment. Additionally, adverse side effects associated with chemotherapeutic agents are generally the major dose-limiting toxicity (DLT) in the administration of these drugs. For example, mucositis is one of the major dose limiting toxicity for several anticancer agents, including the antimetabolite cytotoxic agents 5-FU, methotrexate, and antitumor antibiotics, such as doxorubicin. Many of these chemotherapy-induced side effects if severe may lead to hospitalization, or require treatment with analgesics for the treatment of pain. Some cancer individuals die from the chemotherapy due to poor tolerance to the chemotherapy. The extreme side effects of anticancer drugs are caused by the poor target specificity of such drugs. The drugs circulate through most normal organs of individuals as well as intended target tumors. The poor target specificity that causes side effects also decreases the efficacy of chemotherapy because only a fraction of the drugs is correctly targeted. The efficacy of chemotherapy is further decreased by poor retention of the anti-cancer drugs within the target tumors.

Due to the severity and breadth of neoplasm, tumor and cancer, there is a great need for effective treatments of such diseases or disorders that overcome the shortcomings of surgery, chemotherapy, and radiation treatment.

Problems of Chemotherapeutic Agents

The drug resistance problem is a reason for the added importance of combination chemotherapy, as the therapy both has to avoid the emergence of resistant cells and to kill pre-existing cells which are already drug resistant.

Drug resistance is the name given to the circumstance when a disease does not respond to a treatment drug or drugs. Drug resistance can be either intrinsic, which means the disease has never been responsive to the drug or drugs, or it can be acquired, which means the disease ceases responding to a drug or drugs that the disease had previously been responsive to. Multidrug resistance (MDR) is a specific type of drug resistance that is characterized by cross-resistance of a disease to more than one functionally and/or structurally unrelated drugs. Multidrug resistance in the field of cancer is discussed in greater detail in "Detoxification Mechanisms and Tumor Cell Resistance to Anticancer Drugs," by Kuzmich and Tew, particularly section VII "The Multidrug-Resistant Phenotype (MDR)," Medical Research Reviews, Vol. 11, No. 2, 185-217, (Section VII is at pp. 208-213) (1991); and in "Multidrug Resistance and Chemosensitization: Therapeutic Implications for Cancer Chemotherapy," by Georges, Sharom and Ling, Advances in Pharmacology, Vol. 21, 185-220 (1990).

One form of multi-drug resistance (MDR) is mediated by a membrane bound 170-180 kD energy-dependent efflux pump designated as P-glycoprotein (P-gp). P-glycoprotein has been shown to play a major role in the intrinsic and acquired resistance of a number of human tumors against hydrophobic, natural product drugs. Drugs that act as substrates for and are consequently detoxified by P-gp include the vinca alkaloids (vincristine and vinblastine), anthracyclines (Adriamycin), and epipodophyllotoxins (etoposide). While P-gp associated MDR is a major determinant in tumor cell resistance to chemotherapeutic agents, it is clear that the phenomenon of MDR is multifactorial and involves a number of different mechanisms.

A major complication of cancer chemotherapy and of antiviral chemotherapy is damage to bone marrow cells or suppression of their function. Specifically, chemotherapy damages or destroys hematopoietic precursor cells, primarily found in the bone marrow and spleen, impairing the production of new blood cells (granulocytes, lymphocytes, erythrocytes, monocytes, platelets, etc.). Treatment of cancer individuals with 5-fluorouracil, for example, reduces the number of leukocytes (lymphocytes and/or granulocytes), and can result in enhanced susceptibility of the individuals to infection. Many cancer individuals die of infection or other consequences of hematopoietic failure subsequent to chemotherapy. Chemotherapeutic agents can also result in subnormal formation of platelets which produces a propensity toward hemorrhage. Inhibition of erythrocyte production can result in anemia. For some cancer individuals, the risk of damage to the hematopoietic system or other important tissues frequently limits the opportunity for chemotherapy dose escalation of chemotherapy agents high enough to provide good antitumor or antiviral efficacy. Repeated or high dose cycles of chemotherapy may be responsible for severe stem cell depletion leading to serious long-term hematopoietic sequelea and marrow exhaustion.

Prevention of, or protection from, the side effects of chemotherapy would be a great benefit to cancer individuals. For life-threatening side effects, efforts have concentrated on altering the dose and schedules of the chemotherapeutic agent to reduce the side effects. Other options are becoming available, such as the use of granulocyte colony stimulating factor (G-CSF), granulocyte-macrophage-CSF (GM-CSF), epidermal growth factor (EGF), interleukin 11, erythropoietin, thrombopoietin, megakaryocyte development and growth factor, pixykines, stem cell factor, FLT-ligand, as well as interleukins 1, 3, 6, and 7, to increase the number of normal cells in various tissues before the start of chemotherapy (See Jimenez and Yunis, Cancer Research 52:413-415; 1992). The mechanisms of protection by these factors, while not fully understood, are most likely associated with an increase in the number of normal critical target cells before treatment with cytotoxic agents, and not with increased survival of cells following chemotherapy.

Chemotherapeutic Targeting for Tumor Treatment

Both the growth and metastasis of solid tumors are angiogenesis-dependent (Folkman, J. *Cancer Res.*, 46, 467-73 (1986); Folkman, J. *Nat. Cancer* Inst., 82, 4-6 (1989); Folkman et al., "Tumor Angiogenesis," Chapter 10, pp. 206-32, in The Molecular Basis of *Cancer*, Mendelsohn et al., eds. (W. B. Saunders, 1995)). It has been shown, for example, that tumors which enlarge to greater than 2 mm in diameter must obtain their own blood supply and do so by inducing the growth of new capillary blood vessels. After these new blood vessels become embedded in the tumor, they provide nutrients and growth factors essential for tumor growth as well as a means for tumor cells to enter the circulation and metastasize to distant sites, such as liver, lung or bone (Weidner, New Eng. J. Med., 324(1), 1-8 (1991)). When used as drugs in tumor-bearing animals, natural inhibitors of angiogenesis can prevent the growth of small tumors (O'Reilly et al., O'Reilly et al., Cell, 79, 315-28 (1994)). Indeed, in some protocols, the application of such inhibitors leads to tumor regression and dormancy even after cessation of treatment (O'Reilly et al., Cell, 88, 277-85 (1997)). Moreover, supplying inhibitors of angiogenesis to certain tumors can potentiate their response to other therapeutic regimes (e.g., chemotherapy) (see, e.g., Teischer et al., *Int. J. Cancer*, 57, 920-25 (1994)).

Protein tyrosine kinases catalyze the phosphorylation of specific tyrosyl residues in various proteins involved in the regulation of cell growth and differentiation (A. F. Wilks, Progress in Growth Factor Research, 1990, 2, 97-111; S. A. Courtneidge, Dev. Supp.1, 1993, 57-64; J. A. Cooper, Semin. Cell Biol., 1994, 5(6), 377-387; R. F. Paulson, Semin. Immunol., 1995, 7(4), 267-277; A. C. Chan, Curr. Opin. Immunol., 1996, 8(3), 394-401). Protein tyrosine kinases can be broadly classified as receptor (e.g. EGFr, c-erbB-2, c-met, tie-2, PDGFr, FGFr) or non-receptor (e.g. c-src, lck, Zap70) kinases. Inappropriate or uncontrolled activation of many of these kinases, i.e. aberrant protein tyrosine kinase activity, for example by over-expression or mutation, has been shown to result in uncontrolled cell growth. For example, elevated epidermal growth factor receptor (EGFR) activity has been implicated in non-small cell lung, bladder and head and neck cancers, and increased c-erbB-2 activity in breast, ovarian, gastric and pancreatic cancers. Thus, inhibition of protein tyrosine kinases should be useful as a treatment for tumors such as those outlined above.

Growth factors are substances that induce cell proliferation, typically by binding to specific receptors on cell surfaces. Epidermal growth factor (EGF) induces proliferation of a variety of cells in vivo, and is required for the growth of most cultured cells. The EGF receptor is a 170-180 kD membrane-spanning glycoprotein, which is detectable on a wide variety of cell types. The extracellular N-terminal domain of the receptor is highly glycosylated and binds EGF antibodies that selectively bind to EGFR. Agents that competitively bind to EGFR have been used to treat certain types of cancer, since many tumors of mesodermal and ectodermal origin overexpress the EGF receptor. For example, the EGF receptor has been shown to be overexpressed in many gliomas, squamous cell carcinomas, breast carcinomas, melanomas, invasive bladder carcinomas and esophageal cancers. Attempts to exploit the EGFR system for anti-tumor therapy have generally involved the use of monoclonal antibodies against the EGFR. In addition, studies with primary human mammary tumors have shown a correlation between high EGFR expression and the presence of metastases, higher rates of proliferation, and shorter individual survival.

Herlyn et al., in U.S. Pat. No. 5,470,571, disclose the use of radiolabeled Mab 425 for treating gliomas that express EGFR. Herlyn et al. report that anti-EGFR antibodies may either stimulate or inhibit cancer cell growth and proliferation. Other monoclonal antibodies having specificity for EGFR, either alone or conjugated to a cytotoxic compound, have been reported as being effective for treating certain types of cancer. Bendig et al, in U.S. Pat. No. 5,558,864, disclose therapeutic anti-EGFR Mab's for competitively binding to EGFR. Heimbrook et al., in U.S. Pat. No. 5,690,928, disclose the use of EGF fused to a *Pseudomonas* species-derived endotoxin for the treatment of bladder cancer. Brown et al., in U.S. Pat. No. 5,859,018, disclose a method for treating diseases characterized by cellular hyperproliferation mediated by, inter alia, EGF.

Chemotherapeutic Modes of Administration

People diagnosed as having cancer are frequently treated with single or multiple chemotherapeutic agents to kill cancer cells at the primary tumor site or at distant sites to where cancer has metastasized. Chemotherapy treatment is typically given either in a single or in several large doses or over variable times of weeks to months. However, repeated or high dose cycles of chemotherapy may be responsible for increased toxicities and severe side effects.

New studies suggest that metronomic chemotherapy, the low-dose and frequent administration of cytotoxic agents without prolonged drug-free breaks, targets activated endothelial cells in the tumor vasculature. A number of preclinical studies have demonstrated superior anti-tumor efficacy, potent antiangiogenic effects, and reduced toxicity and side effects (e.g., myelosuppression) of metronomic regimes compared to maximum tolerated dose (MTD) counterparts (Bocci, et al., Cancer Res, 62:6938-6943, (2002); Bocci; et al., PNAS, vol, 100(22):12917-12922, (2003); and Bertolini, et al., Cancer Res, 63(15):4342-4346, (2003)). It remains unclear whether all chemotherapeutic drugs exert similar effects or whether some are better suited for such regimes than others. Nevertheless, metronomic chemotherapy appears to be effective in overcoming some of the major shortcomings associated with chemotherapy.

Chemotherapeutic Agents

Paclitaxel has been shown to have significant antineoplastic and anticancer effects in drug-refractory ovarian cancer and has shown excellent antitumor activity in a wide variety of tumor models, and also inhibits angiogenesis when used at very low doses (Grant et al., Int. J. Cancer, 2003). The poor aqueous solubility of paclitaxel, however, presents a problem for human administration. Indeed, the delivery of drugs that are inherently insoluble or poorly soluble in an aqueous medium can be seriously impaired if oral delivery is not effective. Accordingly, currently used paclitaxel formulations (e.g., Taxol®) require a Cremophor® to solubilize the drug. The presence of Cremophor® in this formulation has been linked to severe hypersensitivity reactions in animals (Lorenz et al., Agents Actions 7:63-67 (1987)) and humans (Weiss et al., J. Clin. Oncol. 8:1263-68 (1990)) and consequently requires premedication of individuals with corticosteroids (dexamethasone) and antihistamines. It was also reported that clinically relevant concentrations of the formulation vehicle Cremophor® EL in Taxol® nullify the antiangiogenic activity of paclitaxel, suggesting that this agent or other anticancer drugs formulated in Cremophor® EL may need to be used at much higher doses than anticipated to achieve effective metronomic chemotherapy (Ng et al., Cancer Res., 64:821-824 (2004)). As such, the advantage of the lack of undesirable side effects associated with low-dose paclitaxel regimes vs. conventional MTD chemotherapy may be compromised. See also U.S. Patent Pub. No. 2004/0143004; WO00/64437.

Abraxane™ is a Cremophor® EL-Free Nanoparticle Albumin-Bound Paclitaxel

Preclinical models have shown significant improvement in the safety and efficacy of Abraxane™ compared with Taxol® (Desai et al., EORTC-NCI-AACR, 2004) and in individuals with metastatic breast cancer (O'Shaughnessy et al., San Antonio Breast Cancer Symposium, Abstract #1122, December 2003). This is possibly due to the absence of surfactants (e.g., Cremophor® or Tween® 80, used in Taxol® and Taxotere®, respectively) in Abraxane™, and/or preferential utilization of an albumin-based transport mechanism utilizing gp60/caveolae on microvascular endothelial cells (Desai et al., EORTC-NCI-AACR, 2004). In addition, both Cremophor® and Tween® 80 have been shown to strongly inhibit the binding of paclitaxel to albumin, possibly affecting albumin based transport (Desai et al., EORTC-NCI-AACR, 2004).

IDN5109 (Ortataxel) is a new taxane, currently in phase II, selected for its lack of cross-resistance in tumor cell lines expressing the multidrug resistant phenotype (MDR/Pgp) and inhibition of P-glycoprotein (Pgp) (Minderman; Cancer Chemother. Pharmacol. 2004; 53:363-9). Due to its hydrophobicity, IDN5109 is currently formulated in the surfactant Tween® 80 (same vehicle as Taxotere®). Removal of surfactants from taxane formulations e.g., in the case of nanoparticle albumin-bound paclitaxel (Abraxane™) showed improvements in safety and efficacy over their surfactant containing counterparts (O'Shaughnessy et al., San Antonio Breast Cancer Symposium, Abstract #1122, December 2003). Tween® 80 also strongly inhibited the binding of the taxane, paclitaxel, to albumin, possibly compromising albumin based drug transport via the gp60 receptor on microvessel endothelial cells (Desai et al., EORTC-NCI-AACR, 2004).

The antitumor activity of colchicine, which is the major alkaloid of the autumn crocus, Colchicum autumnale, and the African climbing lily, Gloriosa superba, was first reported at the beginning of the 20$^{th}$ century. The elucidation of its structure was finally completed from X-ray studies and a number of total syntheses (see Shiau et al., J. Pharm. Sci. 1978, 67(3) 394-397). Colchicine is thought to be a mitotic poison, particularly in tyhmic, intestinal, and hermatopoietic cells, which acts as a spindle poison and blocks the kinesis. Its effect on the mitotic spindle is thought to represent a special case of its effects on various organized, labile, fibrillar systems concerned with structure and movement.

Thiocolchicine dimer IDN5404 was selected for its activity in human ovarian subline resistant to cisplatin and topotecan A2780-CIS and A2780-TOP. This effect was related to dual mechanisms of action, i.e., microtubule activity as in Vinca alkaloids and a topoisomerase I inhibitory effect different from camptothecin. (Raspaglio, Biochemical Pharmacology 69:113-121 (2005)).

It has been found that nanoparticle compositions of a taxane (such as albumin bound paclitaxel (Abraxane™)) have significantly lower toxicities than other taxanes like Taxol® and Taxotere® with significantly improved outcomes in both safety and efficacy.

Combination chemotherapy, e.g., combining one or more chemotherapeutic agents or other modes of treatment, e.g., combining for example, chemotherapy with radiation or surgery and chemotherapy, have been found to be more successful than single agent chemotherapeutics or individual modes of treatment respectively.

Other references include U.S. Pub. No. 2006/0013819; U.S. Pub. No. 2006/0003931; WO05/117986; WO05/117978; and WO05/000900.

More effective treatments for proliferative diseases, especially cancer, are needed.

The disclosures of all publications, patents, patent applications and published patent applications referred to herein are hereby incorporated herein by reference in their entirety.

BRIEF SUMMARY OF THE INVENTION

The present invention provides methods for the treatment of proliferative diseases such as cancer. The invention provides combination therapy methods of treating proliferative diseases (such as cancer), comprising a) a first therapy comprising administering to an individual an effective amount of a composition comprising nanoparticles comprising a taxane (such as paclitaxel) and a carrier protein (such as albumin) and b) a second therapy, such as chemotherapy, radiation therapy, surgery, or combinations thereof. In another aspect, there are provided methods of administering to an individual a composition comprising nanoparticles comprising a taxane (such as paclitaxel) and a carrier protein (such as albumin) based on a metronomic dosing regime.

In some embodiments, the invention provides a method of treating a proliferative disease (such as cancer) in an individual comprising administering to the individual a) an effective amount of a composition comprising nanoparticles comprising a taxane and a carrier protein (such as albumin), and b) an effective amount of at least one other chemotherapeutic agent. In some embodiments, the invention provides a method of treating a proliferative disease (such as cancer) in an individual comprising administering to the individual a) an effective amount of a composition comprising nanoparticles comprising paclitaxel and an albumin (such as Abraxane™), and b) an effective amount of at least one other chemotherapeutic agent. In some embodiments, the chemotherapeutic agent is any of (and in some embodiments selected from the group consisting of) antimetabolites (including nucleoside analogs), platinum-based agents, alkylating agents, tyrosine kinase inhibitors, anthracycline antibiotics, vinca alkloids, proteasome inhibitors, macrolides, and topoisomerase inhibitors. In some embodiments, the chemotherapeutic agent is a platinum-based agent, such as carboplatin.

In some embodiments, the composition comprising nanoparticles (also referred to as "nanoparticle composition") and the chemotherapeutic agent are administered simultaneously, either in the same composition or in separate compositions. In some embodiments, the nanoparticle composition and the chemotherapeutic agent are administered sequentially, i.e., the nanoparticle composition is administered either prior to or after the administration of the chemotherapeutic agent. In some embodiments, the administration of the nanoparticle composition and the chemotherapeutic agent are concurrent, i.e., the administration period of the nanoparticle composition and that of the chemotherapeutic agent overlap with each other. In some embodiments, the administration of the nanoparticle composition and the chemotherapeutic agent are nonconcurrent. For example, in some embodiments, the administration of the nanoparticle composition is terminated before the chemotherapeutic agent is administered. In some embodiments, the administration of the chemotherapeutic agent is terminated before the nanoparticle composition is administered.

In some embodiments, the first therapy taxane is nanoparticle albumin bound paxlitaxel, described, for example, in U.S. Pat. No. 6,566,405, and commercially available under the tradename Abraxane™. In addition, the first therapy taxane is also considered to be nanoparticle albumin bound docetaxel described for example in U.S. Patent Application Publication 2005/0004002A1.

In another aspect, there is provided a method of treating a proliferative disease (such as cancer) in an individual comprising a) a first therapy comprising administering to the individual a composition comprising nanoparticles comprising a taxane and a carrier protein (such as albumin), and b) a second therapy comprising radiation therapy, surgery, or combinations thereof. In some embodiments, there is provided a method of treating a proliferative disease (such as cancer) in an individual comprising a) a first therapy comprising administering to the individual a composition comprising nanoparticles comprising paclitaxel and an albumin (such as Abraxane™), and b) a second therapy comprising radiation therapy, surgery, or combinations thereof. In some embodiments, the second therapy is radiation therapy. In some embodiments, the second therapy is surgery. In some embodiments, the first therapy is carried out prior to the second therapy. In some embodiments, the first therapy is carried out after the second therapy.

In another aspect, the method comprises administering to a mammal having a proliferative disease (such as cancer) a combination therapy comprising a first therapy comprising a taxane and a second therapy selected from the group consisting of chemotherapeutic agent and radiation or combinations thereof. The combination therapy may be administered in any of a variety of ways such as sequentially or simultaneously, and if sequential, the taxane may be administered before or after the second therapy although it is preferred that the first therapy comprising a taxane is administered first. It will also be understood that the second therapy can include more than one chemotherapeutic agent.

The present invention also provides metronomic therapy regimes. In some embodiments, there is provided a method of administering a composition comprising nanoparticles comprising a taxane and a carrier protein (such as albumin), wherein the nanoparticle composition is administered over a period of at least one month, wherein the interval between each administration is no more than about a week, and wherein the dose of taxane at each administration is about 0.25% to about 25% of its maximum tolerated dose following a traditional dosing regime. In some embodiments, there is provided a method of administering a composition comprising nanoparticles comprising paclitaxel and an albumin (such as Abraxane™), wherein the nanoparticle composition is administered over a period of at least one month, wherein the interval between each administration is no more than about a week, and wherein the dose of paclitaxel at each administration is about 0.25% to about 25% of its maximum tolerated dose following a traditional dosing regime. In some embodiments, the dose of the taxane (such as paclitaxel, for example Abraxane™) per administration is less than about any of 1%, 2%, 3%, 4%, 5%, 6%, 7%, 8%, 9%, 10%, 11%, 12%, 13%, 14%, 15%, 18%, 20%, 22%, 24%, or 25% of the maximum tolerated dose. In some embodiments, the nanoparticle composition is administered at least about any of 1x, 2x, 3x, 4x, 5x, 6x, 7x (i.e., daily) a week. In some embodiments, the intervals between each administration are less than about any of 7 days, 6 days, 5 days, 4 days, 3 days, 2 days, and 1 day. In some embodiments, the nanoparticle composition is administered over a period of at least about any of 2, 3, 4, 5, 6, 7, 8, 9, 10, 11, 12, 18, 24, 30 and 36 months.

In some embodiments, there is provided a method of administering a composition comprising nanoparticles comprising a taxane and a carrier protein (such as albumin), wherein the taxane is administered over a period of at least one month, wherein the interval between each administration is no more than about a week, and wherein the dose of the taxane at each administration is about 0.25 mg/m$^2$ to about 25 mg/m$^2$. In some embodiments, there is provided a method of administering a composition comprising nanoparticles comprising paclitaxel and an albumin (such as Abraxane™) and a carrier protein (such as albumin), wherein the paclitaxel is administered over a period of at least one month, wherein the interval between each administration is no more than about a week, and wherein the dose of the taxane at each administration is about 0.25 mg/m$^2$ to about 25 mg/m$^2$. In some embodiments, the dose of the taxane (such as paclitaxel, for example Abraxane™) per administration is less than about any of 2, 3, 4, 5, 6, 7, 8, 9, 10, 11, 12, 13, 14, 15, 18, 20, 22, and 25 mg/m$^2$. In some embodiments, the nanoparticle composition is administered at least about any of 1x, 2x, 3x, 4x, 5x, 6x, 7x (i.e., daily) a week. In some embodiments, the intervals between each administration are less than about any of 7 days, 6 days, 5 days, 4 days, 3 days, 2 days, and 1 day. In some embodiments, the nanoparticle composition is administered over a period of at least about any of 2, 3, 4, 5, 6, 7, 8, 9, 10, 11, 12, 18, 24, 30 and 36 months.

The methods of the invention generally comprise administration of a composition comprising nanoparticles comprising a taxane and a carrier protein. In some embodiments, the nanoparticle composition comprises nanoparticles comprising paclitaxel and an albumin. In some embodiments, the paclitaxel/albumin nanoparticles have an average diameter of no greater than about 200 nm. In some embodiments, the paclitaxel/albumin nanoparticle composition is substantially free (such as free) of surfactant (such as Cremophor). In some embodiments, the weight ratio of the albumin to paclitaxel in the composition is about 18:1 or less, such as about 9:1 or less. In some embodiments, the paclitaxel is coated with albumin. In some embodiments, the paclitaxel/albumin nanoparticles have an average diameter of no greater than about 200 nm and the paclitaxel/albumin composition is substantially free (such as free) of surfactant (such as Cremophor). In some embodiments, the paclitaxel/albumin nanoparticles have an average diameter of no greater than about 200 nm and the paclitaxel is coated with albumin. Other combinations of the above characteristics are also contemplated. In some embodiments, the nanoparticle composition is Abraxane™. Nanoparticle compositions comprising other taxanes (such as docetaxel and ortataxel) may also comprise one or more of the above characteristics.

These and other aspects and advantages of the present invention will become apparent from the subsequent detailed description and the appended claims. It is to be understood that one, some, or all of the properties of the various embodiments described herein may be combined to form other embodiments of the present invention.

BRIEF DESCRIPTION OF FIGURES

FIG. 1A shows the effect of ABI-007 on rat aortic ring angiogenesis. FIG. 1B shows the effect of ABI-007 on human endothelial cell proliferation. FIG. 1C shows the effect of ABI-007 on endothelial cell tube formation.

FIG. 7A and FIG. 7B show the cytotoxic activity of nab-rapamycin in combination with Abraxane™ on vascular smooth muscle cells. Cytotoxicity was evaluated by staining with ethidium homodimer-1 (FIG. 7A) or by staining with calcein (FIG. 7B).

DETAILED DESCRIPTION OF THE INVENTION

Figure 2:
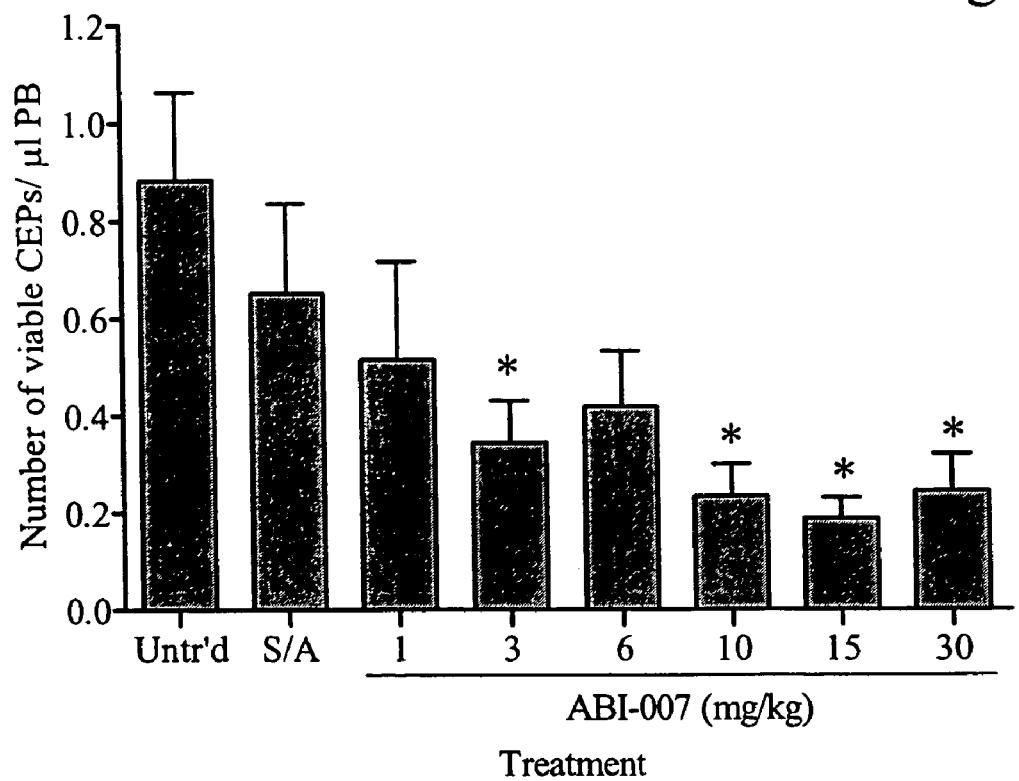
FIG. 2 shows the determination of an optimal biological dose of ABI-007 for metronomic dosing. Shown are the levels of viable circulating endothelial progenitors (CEPs) in peripheral blood of Balb/cJ mice in response to escalating doses of ABI-007. Untr'd, untreated control; S/A, saline/albumin vehicle control. Bars, mean±SE. * Significantly ($p<0.05$) different from the untreated control.

The present invention provides methods of combination therapy comprising a first therapy comprising administration of nanoparticles comprising a taxane and a carrier protein (such as albumin) in conjunction with a second therapy such as radiation, surgery, administration of at least one other chemotherapeutic agent, or combinations thereof. The invention also provides methods of metronomic therapy.

The present invention involves the discovery that Abraxane™, due to its superior anti-tumor activity and reduced toxicity and side effects, can be administered in combination with other therapeutic drugs and/or treatment modalities and can also be used in metronomic chemotherapy. Due to significantly improved safety profiles with compositions comprising drug/carrier protein nanoparticles (such as Abraxane™), we believe that combination chemotherapy with such nanoparticle compositions (such as Abraxane™) is more effective than combination chemotherapy with other drugs. In addition the use of nanoparticle composition (such as Abraxane™) in combination with radiation is also believed to be more effective than combination of other agents with radiation. Thus, the nanoparticle compositions (especially a paclitaxel/albumin nanoparticle composition, such as Abraxane™), when used in combination with other chemotherapeutic agents or when combined with other treatment modalities, should be very effective and overcome the deficiencies of surgery, radiation treatment, and chemotherapy in the treatment of proliferative disease (such as cancer).

The present invention in one its embodiments is the use of a first therapy comprising a taxane, such as Abraxane™, in combination with a second therapy such as another chemotherapeutic agent or agents, radiation, or the like for treating proliferative diseases such as cancer. The first therapy comprising a taxane and second therapy can be administered to a mammal having the proliferative sequentially, or they can be co-administered, and even administered simultaneously in the same pharmaceutical composition.

Further, a metronomic dosing regime using Abraxane™ has been found to be more effective than the traditional MTD dosing schedule of the same drug composition. Such metronomic dosing regime of Abraxane™ has also been found to be more effective than metronomic dosing of Taxol®.

The methods described herein are generally useful for treatment of diseases, particularly proliferative diseases. As used herein, "treatment" is an approach for obtaining beneficial or desired clinical results. For purposes of this invention, beneficial or desired clinical results include, but are not limited to, any one or more of: alleviation of one or more symptoms, diminishment of extent of disease, stabilized (i.e., not worsening) state of disease, preventing or delaying spread (e.g., metastasis) of disease, preventing or delaying occurrence or recurrence of disease, delay or slowing of disease progression, amelioration of the disease state, and remission (whether partial or total). Also encompassed by "treatment" is a reduction of pathological consequence of a proliferative disease. The methods of the invention contemplate any one or more of these aspects of treatment.

As used herein, a "proliferative disease" is defined as a tumor disease (including benign or cancerous) and/or any metastases, wherever the tumor or the metastasis are located, more especially a tumor selected from the group comprising one or more of (and in some embodiments selected from the group consisting of) breast cancer, genitourinary cancer, lung cancer, gastrointestinal cancer, epidermoid cancer, melanoma, ovarian cancer, pancreatic cancer, neuroblastoma, colorectal cancer, head and neck cancer. In a broader sense of the invention, a proliferative disease may furthermore be selected from hyperproliferative conditions such as hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty. In some embodiments, the proliferative disease is cancer. In some embodiments, the proliferative disease is a non-cancerous disease. In some embodiments, the proliferative disease is a benign or malignant tumor. Where hereinbefore and subsequently a tumor, a tumor disease, a carcinoma or a cancer are mentioned, also metastasis in the original organ or tissue and/or in any other location are implied alternatively or in addition, whatever the location of the tumor and/or metastasis is.

The term "effective amount" used herein refers to an amount of a compound or composition sufficient to treat a specified disorder, condition or disease such as ameliorate, palliate, lessen, and/or delay one or more of its symptoms. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more administrations. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

In some embodiments, there is provided a method of treating a primary tumor. In some embodiments, there is provided a method of treating metastatic cancer (that is, cancer that has metastasized from the primary tumor). In some embodiments, there is provided a method of treating cancer at advanced stage(s). In some embodiments, there is provided a method of treating breast cancer (which may be HER2 positive or HER2 negative), including, for example, advanced breast cancer, stage IV breast cancer, locally advanced breast cancer, and metastatic breast cancer. In some embodiments, there is provided a method of treating lung cancer, including, for example, non-small cell lung cancer (NSCLC, such as advanced NSCLC), small cell lung cancer (SCLC, such as advanced SCLC), and advanced solid tumor malignancy in the lung. In some embodiments, there is provided a method of treating any of ovarian cancer, head and neck cancer, gastric malignancies, melanoma (including metastatic melanoma), colorectal cancer, pancreatic cancer, and solid tumors (such as advanced solid tumors). In some embodiments, there is provided a method of reducing cell proliferation and/or cell migration. In some embodiments, there is provided a method of treating any of the following diseases: restenosis, stenosis, fibrosis, angiogenesis, psoriasis, atherosclerosis, and proliferation of smooth muscle cells. The present invention also provides methods of delaying development of any of the proliferative diseases described herein.

The term "individual" is a mammal, including humans. An individual includes, but is not limited to, human, bovine, horse, feline, canine, rodent, or primate. In some embodiments, the individual is human. The individual (such as human) may have advanced disease or lesser extent of disease, such as low tumor burden. In some embodiments, the individual is at an early stage of a proliferative disease (such as cancer). In some embodiments, the individual is at an advanced stage of a proliferative disease (such as an advanced cancer). In some embodiments, the individual is HER2 positive. In some embodiments, the individual is HER2 negative.

The methods may be practiced in an adjuvant setting. "Adjuvant setting" refers to a clinical setting in which an individual has had a history of a proliferative disease, particularly cancer, and generally (but not necessarily) been responsive to therapy, which includes, but is not limited to, surgery (such as surgical resection), radiotherapy, and chemotherapy. However, because of their history of the proliferative disease (such as cancer), these individuals are considered at risk of development of the disease. Treatment or administration in the "adjuvant setting" refers to a subsequent mode of treatment. The degree of risk (i.e., when an individual in the adjuvant setting is considered as "high risk" or "low risk") depends upon several factors, most usually the extent of disease when first treated. The methods provided herein may also be practiced in a neoadjuvant setting, i.e., the method may be carried out before the primary/definitive therapy. In some embodiments, the individual has previously been treated. In some embodiments, the individual has not previously been treated. In some embodiments, the treatment is a first line therapy.

It is understood that aspect and embodiments of the invention described herein include "consisting" and/or "consisting essentially of" aspects and embodiments.

Combination Therapy with Chemotherapeutic Agent

The present invention provides methods of treating a proliferative disease (such as cancer) in an individual, comprising administering to the individual: a) an effective amount of a composition comprising nanoparticles comprising a taxane and a carrier protein (such as albumin); and b) an effective amount of at least one other chemotherapeutic agent. In some embodiments, the taxane is any of (and in come embodiments consisting essentially of) paclitaxel, docetaxel, and ortataxel. In some embodiments, the nanoparticle composition comprises Abraxane™. In some embodiments, the chemotherapeutic agent is any of (and in some embodiments selected from the group consisting of) antimetabolite agents (including nucleoside analogs), platinum-based agents, alkylating agents, tyrosine kinase inhibitors, anthracycline antibiotics, vinca alkloids, proteasome inhibitors, macrolides, and topoisomerase inhibitors.

In some embodiments, the method comprises administering to the individual: a) an effective amount of a composition comprising nanoparticles comprising paclitaxel and an albumin; and b) an effective amount of at least one other chemotherapeutic agent. In some embodiments, the paclitaxel/albumin nanoparticles have an average diameter of no greater than about 200 nm. In some embodiments, the paclitaxel/albumin nanoparticle composition is substantially free (such as free) of surfactant (such as Cremophor). In some embodiments, the weight ratio of the albumin to paclitaxel in the composition is about 18:1 or less, such as about 9:1 or less. In some embodiments, the paclitaxel is coated with albumin. In some embodiments, the paclitaxel/albumin nanoparticles have an average diameter of no greater than about 200 nm and the paclitaxel/albumin composition is substantially free (such as free) of surfactant (such as Cremophor). In some embodiments, the paclitaxel/albumin nanoparticles have an average diameter of no greater than about 200 nm and the paclitaxel is coated with albumin. In some embodiments, the nanoparticle composition is Abraxane™.

In some embodiments, the invention provides a method of treating a proliferative disease (such as cancer) in an individual comprising administering to the individual a) an effective amount of Abraxane™, and b) an effective amount of at least one other chemotherapeutic agent. Preferred drug combinations for sequential or co-administration or simultaneous administration with Abraxane™ are those which show enhanced antiproliferative activity when compared with the single components alone, especially combinations that that lead to regression of proliferative tissues and/or cure from proliferative diseases.

The chemotherapeutic agents described herein can be the agents themselves, pharmaceutically acceptable salts thereof, and pharmaceutically acceptable esters thereof, as well as steroisomers, enantiomers, racemic mixtures, and the like. The chemotherapeutic agent or agents as described can be administered as well as a pharmaceutical composition containing the agent(s), wherein the pharmaceutical composition comprises a pharmaceutically acceptable carrier vehicle, or the like.

The chemotherapeutic agent may be present in a nanoparticle composition. For example, in some embodiments, there is provided a method of treating a proliferative disease (such as cancer) in an individual, comprising administering to the individual: a) an effective amount of a composition comprising nanoparticles comprising a taxane and a carrier protein (such as albumin); and b) an effective amount of a composition comprising nanoparticles comprising at least one other chemotherapeutic agent and a carrier protein (such as albumin). In some embodiments, the method comprises administering to the individual: a) an effective amount of a composition comprising nanoparticles comprising paclitaxel and an albumin (such as Abraxane™); and b) an effective amount of a composition comprising nanoparticles comprising at least one other chemotherapeutic agent and a carrier protein (such as albumin). In some embodiments, the chemotherapeutic agent is any of (and in some embodiments selected from the group consisting of) thiocolchicine or its derivatives (such as dimeric thiocolchicine, including for example nab-5404, nab-5800, and nab-5801), rapamycin or its derivatives, and geldanamycin or its derivatives (such as 17-allyl amino geldanamycin (17-AAG)). In some embodiments, the chemotherapeutic agent is rapamycin. In some embodiments, the chemotherapeutic agent is 17-AAG.

An exemplary and non-limiting list of chemotherapeutic agents contemplated is provided herein. Suitable chemotherapeutic agents include, for example, vinca alkaloids, agents that disrupt microtubule formation (such as colchicines and its derivatives), anti-angiogenic agents, therapeutic antibodies, EGFR targeting agents, tyrosine kinase targeting agent (such as tyrosine kinase inhibitors), transitional metal complexes, proteasome inhibitors, antimetabolites (such as nucleoside analogs), alkylating agents, platinum-based agents, anthracycline antibiotics, topoisomerase inhibitors, macrolides, therapeutic antibodies, retinoids (such as all-trans retinoic acids or a derivatives thereof); geldanamycin or a derivative thereof (such as 17-AAG), and other standard chemotherapeutic agents well recognized in the art.

In some embodiments, the chemotherapeutic agent is any of (and in some embodiments selected from the group consisting of) adriamycin, colchicine, cyclophosphamide, actinomycin, bleomycin, duanorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof (e.g., paclitaxel and derivatives thereof, taxotere and derivatives thereof, and the like), topetecan, vinblastine, vincristine, tamoxifen, pipo-sulfan, nab-5404, nab-5800, nab-5801, Irinotecan, HKP, Ortataxel, gemcitabine, Herceptin®, vinorelbine, Doxil®, capecitabine, Alimta®, Avastin®, Velcade®, Tarceva®, Neulasta®, Lapatinib, Sorafenib, derivatives thereof, chemotherapeutic agents known in the art, and the like. In some embodiments, the chemotherapeutic agent is a composition comprising nanoparticles comprising a thiocolchicine derivative and a carrier protein (such as albumin).

In some embodiments, the chemotherapeutic agent is a antineoplastic agent including, but is not limited to, carboplatin, Navelbine® (vinorelbine), anthracycline (Doxil®), lapatinib (GW57016), Herceptin®, gemcitabine (Gemzar®), capecitabine (Xeloda®), Alimta®, cisplatin, 5-fluorouracil, epirubicin, cyclophosphamide, Avastin®, Velcade®, etc.

In some embodiments, the chemotherapeutic agent is an antagonist of other factors that are involved in tumor growth, such as EGFR, ErbB2 (also known as Herb), ErbB3, ErbB4, or TNF. Sometimes, it may be beneficial to also administer one or more cytokines to the individual. In some embodiments, the therapeutic agent is a growth inhibitory agent. Suitable dosages for the growth inhibitory agent are those presently used and may be lowered due to the combined action (synergy) of the growth inhibitory agent and the taxane.

In some embodiments, the chemotherapeutic agent is a chemotherapeutic agent other than an anti-VEGF antibody, a HER2 antibody, interferon, and an HGF, antagonist.

Reference to a chemotherapeutic agent herein applies to the chemotherapeutic agent or its derivatives and accordingly the invention contemplates and includes either of these embodiments (agent; agent or derivative(s)). "Derivatives" or "analogs" of a chemotherapeutic agent or other chemical moiety include, but are not limited to, compounds that are structurally similar to the chemotherapeutic agent or moiety or are in the same general chemical class as the chemotherapeutic agent or moiety. In some embodiments, the derivative or analog of the chemotherapeutic agent or moiety retains similar chemical and/or physical property (including, for example, functionality) of the chemotherapeutic agent or moiety.

In some embodiments, the invention provides a method of treating a proliferative disease (such as cancer) in an individual, comprising administering to the individual a) an effective amount of a composition comprising nanoparticles comprising a taxane and a carrier protein (such as albumin), and b) an effective amount of a tyrosine kinase inhibitor. In some embodiments, the invention provides a method of treating a proliferative disease (such as cancer) in an individual, comprising administering to the individual a) an effective amount of a composition comprising nanoparticles comprising paclitaxel and an albumin (such as Abraxane™), and b) an effective amount of a tyrosine kinase inhibitor. Suitable tyrosine kinase inhibitors include, for example, imatinib (Gleevec®), gefitinib (Iressa®), Tarceva, Sutent® (sunitinib malate), and Lapatinib. In some embodiments, the tyrosine kinase inhibitor is lapatinib. In some embodiments, the tyrosine kinase inhibitor is Tarceva. Tarceva is a small molecule human epidermal growth factor type 1/epidermal growth factor receptor (HER1/EGFR) inhibitor which demonstrated, in a Phase III clinical trial, an increased survival in advanced non-small cell lung cancer (NSCLC) individuals. In some embodiments, the method is for treatment of breast cancer, including treatment of metastatic breast cancer and treatment of breast cancer in a neoadjuvant setting. In some embodiments, the method is for treatment of advanced solid tumor. In some embodiments, there is provided a method to inhibit the proliferation of EGFR expressing tumors in a mammal comprising administering to a mammal infected with such tumors Abraxane™ and gefitinib, wherein the gefitinib is administered by pulse-dosing.

In some embodiments, the invention provides a method of treating a proliferative disease (such as cancer) in an individual, comprising administering to the individual a) an effective amount of a composition comprising nanoparticles comprising a taxane and a carrier protein (such as albumin), and b) an effective amount of an antimetabolite agent (such as a nucleoside analog, including for example purine analogs and pyrimidine analogs). In some embodiments, the invention provides a method of treating a proliferative disease (such as cancer) in an individual, comprising administering to the individual a) an effective amount of a composition comprising nanoparticles comprising paclitaxel and an albumin (such as Abraxane™), and b) an effective amount of an antimetabolite agent. An "antimetabolic agent" is an agent which is structurally similar to a metabolite, but cannot be used by the body in a productive manner. Many antimetabolite agents interfere with production of nucleic acids, RNA and DNA. For example, the antimetabolite can be a nucleoside analog, which includes, but is not limited to, azacitidine, azathioprine, capecitabine (Xeloda®), cytarabine, cladribine, cytosine arabinoside (ara-C, cytosar), doxifluridine, fluorouracil (such as 5-fluorouracil), UFT, hydoxyurea, gemcitabine, mercaptopurine, methotrexate, thioguanine (such as 6-thioguanine). Other anti-metabolites include, for example, L-asparaginase (Elspa), decarbazine (DTIC), 2-deoxy-D-glucose, and procarbazine (matulane). In some embodiments, the nucleoside analog is any of (and in some embodiments selected from the group consisting of) gemcitabine, fluorouracil, and capecitabine. In some embodiments, the method is for treatment of metastatic breast cancer or locally advanced breast cancer. In some embodiments, the method is for first line treatment of metastatic breast cancer. In some embodiments, the method is for treatment of breast cancer in a neoadjuvant setting. In some embodiments, the method is for treatment of any of NSCLC, metastatic colorectal cancer, pancreatic cancer, or advanced solid tumor.

In some embodiments, the invention provides a method of treating a proliferative disease (such as cancer) in an individual, comprising administering to the individual a) an effective amount of a composition comprising nanoparticles comprising a taxane and a carrier protein (such as albumin), and b) an effective amount of an alkylating agent. In some embodiments, the invention provides a method of treating a proliferative disease (such as cancer) in an individual, comprising administering to the individual a) an effective amount of a composition comprising nanoparticles comprising paclitaxel and an albumin (such as Abraxane™), and b) an effective amount of an alkylating agent. Suitable alkylating agents include, but are not limited to, cyclophosphamide (Cytoxan), mechlorethamine, chlorambucil, melphalan, carmustine (BCNU), thiotepa, busulfan, alkyl sulphonates, ethylene imines, nitrogen mustard analogs, estramustine sodium phosphate, ifosfamide, nitrosoureas, lomustine, and streptozocin. In some embodiments, the alkylating agent is cyclophosphamide. In some embodiments, the cyclophosphamide is administered prior to the administration of the nanoparticle composition. In some embodiments, the method is for treatment of an early stage breast cancer. In some embodiments, the method is for treatment of a breast cancer in an adjuvant or a neoadjuvant setting.

In some embodiments, the invention provides a method of treating a proliferative disease (such as cancer) in an individual, comprising administering to the individual a) an effective amount of a composition comprising nanoparticles comprising a taxane and a carrier protein (such as albumin), and b) an effective amount of a platinum-based agent. In some embodiments, the invention provides a method of treating a proliferative disease (such as cancer) in an individual, comprising administering to the individual a) an effective amount of a composition comprising nanoparticles comprising paclitaxel and an albumin (such as Abraxane™), and b) an effective amount of a platinum-based agent. Suitable platinum-based agents include, but are not limited to, carboplatin, cisplatin, and oxaliplatin. In some embodiments, the platinum-based agent is carboplatin. In some embodiments, the method is for treatment of: breast cancer (HER2 positive or HER2 negative, including metastatic breast cancer and advanced breast cancer); lung cancer (including advanced NSCLC, first line NSCLC, SCLC, and advanced solid tumor malignancies in the lung); ovarian cancer; head and neck cancer; and melanoma (including metastatic melanoma).

In some embodiments, the invention provides a method of treating a proliferative disease (such as cancer) in an individual, comprising administering to the individual a) an effective amount of a composition comprising nanoparticles comprising a taxane and a carrier protein (such as albumin), and b) an effective amount of an anthracycline antibiotic. In some embodiments, the invention provides a method of treating a proliferative disease (such as cancer) in an individual, comprising administering to the individual a) an effective amount of a composition comprising nanoparticles comprising paclitaxel and an albumin (such as Abraxane™) and a carrier protein (such as albumin), and b) an effective amount of an anthracycline antibiotic. Suitable anthracycline antibiotic include, but are not limited to, Doxil®, actinomycin, dactinomycin, daunorubicin (daunomycin), doxorubicin (adriamycin), epirubicin, idarubicin, mitoxantrone, valrubicin. In some embodiments, the anthracycline is any of (and in some embodiments selected from the group consisting of) Doxil®, epirubicin, and doxorubicin. In some embodiments, the method is for treatment of an early stage breast cancer. In some embodiments, the method is for treatment of a breast cancer in an adjuvant or a neoadjuvant setting.

In some embodiments, the invention provides a method of treating a proliferative disease (such as cancer) in an individual, comprising administering to the individual a) an effective amount of a composition comprising nanoparticles comprising a taxane and a carrier protein (such as albumin), and b) an effective amount of a vinca alkloid. In some embodiments, the invention provides a method of treating a proliferative disease (such as cancer) in an individual, comprising administering to the individual a) an effective amount of a composition comprising nanoparticles comprising palitaxel and an albumin (such as Abraxane™) and a carrier protein (such as albumin), and b) an effective amount of a vinca alkloid. Suitable vinca alkaloids include, for example, vinblastine, vincristine, vindesine, vinorelbine (Navelbine®), and VP-16. In some embodiments, the vinca alkaloid is vinorelbine (Navelbine®). In some embodiments, the method is for treatment of stage IV breast cancer and lung cancer.

In some embodiments, the invention provides a method of treating a proliferative disease (such as cancer) in an individual, comprising administering to the individual a) an effective amount of a composition comprising nanoparticles comprising a taxane and a carrier protein (such as albumin), and b) an effective amount of a macrolide. In some embodiments, the invention provides a method of treating a proliferative disease (such as cancer) in an individual, comprising administering to the individual a) an effective amount of a composition comprising nanoparticles comprising paclitaxel and an albumin (such as Abraxane™) and a carrier protein (such as albumin), and b) an effective amount of a macrolide. Suitable macrolides include, for example, rapamycin, carbomycin, and erythromycin. In some embodiments, the macrolide is rapamycin or a derivative thereof. In some embodiments, the method is for treatment of a solid tumor.

In some embodiments, the invention provides a method of treating a proliferative disease (such as cancer) in an individual, comprising administering to the individual a) an effective amount of a composition comprising nanoparticles comprising a taxane and a carrier protein (such as albumin), and b) an effective amount of a topoisomerase inhibitor. In some embodiments, the invention provides a method of treating a proliferative disease (such as cancer) in an individual, comprising administering to the individual a) an effective amount of a composition comprising nanoparticles comprising paclitaxel and an albumin (such as Abraxane™) and a carrier protein (such as albumin), and b) an effective amount of a topoisomerase inhibitor. In some embodiments, the chemotherapeutic agent is a topoisomerase inhibitor, including, for example, inhibitor of topoisomerase I and topoisomerase II. Exemplary inhibitors of topoisomerase I include, but are not limited to, camptothecin, such as irinotecan and topotecan. Exemplary inhibitors of topoisomerase II include, but are not limited to, amsacrine, etoposide, etoposide phosphate, and teniposide.

In some embodiments, the invention provides a method of treating a proliferative disease (such as cancer) in an individual, comprising administering to the individual a) an effective amount of a composition comprising nanoparticles comprising a taxane and a carrier protein (such as albumin), and b) an effective amount of an antiangiogenic agent. In some embodiments, the invention provides a method of treating a proliferative disease (such as cancer) in an individual, comprising administering to the individual a) an effective amount of a composition comprising nanoparticles comprising paclitaxel and an albumin (such as Abraxane™) and a carrier protein (such as albumin), and b) an effective amount of an antiangiogenic agent. In some embodiments, the method is for treatment of metastatic breast cancer, breast cancer in an adjuvant setting or a neoadjuvant setting, lung cancer (such as first line advanced NSCLC and NSCLC), ovarian cancer, and melanoma (including metastatic melanoma).

Many anti-angiogenic agents have been identified and are known in the art, including those listed by Carmeliet and Jain (2000). The anti-angiogenic agent can be naturally occurring or non-naturally occurring. In some embodiments, the chemotherapeutic agent is a synthetic antiangiogenic peptide. For example, it has been previously reported that the antiangiogenic activity of small synthetic pro-apoptic peptides comprise two functional domains, one targeting the CD13 receptors (aminopeptidase N) on tumor microvessels and the other disrupting the mitochondrial membrane following internalization. Nat. Med. 1999, 5(9):1032-8. A second generation dimeric peptide, CNGRC-GG-d(KLAKLAK)2, named HKP (Hunter Killer Peptide) was found to have improved antitumor activity. Accordingly, in some embodiments, the antiangiogenic peptide is HKP. In some embodiments, the antiangiogenic agent is other than an anti-VEGF antibody (such as Avastin®).

In some embodiments, the invention provides a method of treating a proliferative disease (such as cancer) in an individual, comprising administering to the individual a) an effective amount of a composition comprising nanoparticles comprising a taxane and a carrier protein (such as albumin), and b) an effective amount of a proteasome inhibitor, such as bortezomib (Velcade). In some embodiments, the invention provides a method of treating a proliferative disease (such as cancer) in an individual, comprising administering to the individual a) an effective amount of a composition comprising nanoparticles comprising paclitaxel and an albumin (such as Abraxane™) and a carrier protein (such as albumin), and b) an effective amount of a proteasome inhibitor such as bortezomib (Velcade).

In some embodiments, the invention provides a method of treating a proliferative disease (such as cancer) in an individual, comprising administering to the individual a) an effective amount of a composition comprising nanoparticles comprising a taxane and a carrier protein (such as albumin), and b) an effective amount of a therapeutic antibody. In some embodiments, the invention provides a method of treating a proliferative disease (such as cancer) in an individual, comprising administering to the individual a) an effective amount of a composition comprising nanoparticles comprising paclitaxel and an albumin (such as Abraxane™) and a carrier protein (such as albumin), and b) an effective amount of a therapeutic antibody. Suitable therapeutic antibodies include, but are not limited to, anti-VEGF antibody (such as Avastin® (bevacizumab)), anti-HER2 antibody (such as Herceptin® (trastuzumab)), Erbitux® (cetuximab), Campath (alemtuzumab), Myelotarg (gemtuzumab), Zevalin (ibritumomab tiuextan, Rituxan (rituximab), and Bexxar (tositumomab). In some embodiments, the chemotherapeutic agent is Erbitux® (cetuximab). In some embodiments, the chemotherapeutic agent is a therapeutic antibody other than an antibody against VEGF or HER2. In some embodiments, the method is for treatment of HER2 positive breast cancer, including treatment of advanced breast cancer, treatment of metastatic cancer, treatment of breast cancer in an adjuvant setting, and treatment of cancer in a neoadjuvant setting. In some embodiments, the method is for treatment of any of metastatic breast cancer, breast cancer in an adjuvant setting or a neoadjuvant setting, lung cancer (such as first line advanced NSCLC and NSCLC), ovarian cancer, head and neck cancer, and melanoma (including metastatic melanoma). For example, in some embodiments, there is provided a method for treatment of HER2 positive metastatic breast cancer in an individual, comprising administering to the individual 125 mg/m² paclitaxel/albumin nanoparticle composition (such as Abraxane™) weekly for three weeks with the fourth week off, concurrent with the administration of Herceptin®.

In some embodiments, two or more chemotherapeutic agents are administered in addition to the taxane in the nanoparticle composition. These two or more chemotherapeutic agents may (but not necessarily) belong to different classes of chemotherapeutic agents. Examples of these combinations are provided herein. Other combinations are also contemplated.

In some embodiments, there is provided a method of treating a proliferative disease (such as cancer) in an individual, comprising administering to the individual a) an effective amount of a composition comprising nanoparticles comprising a taxane and a carrier protein (such as albumin), b) an effective amount of an antimetabolite (such as a nucleoside analog, for example, gemcitabine), and c) an anthracycline antibiotic (such as epirubicin). In some embodiments, there is provided a method of treating a proliferative disease (such as cancer) in an individual, comprising administering to the individual a) an effective amount of a composition comprising nanoparticles comprising paclitaxel and an albumin (such as Abraxane™), b) an effective amount of an antimetabolite (such as a nucleoside analog, for example, gemcitabine), and c) an effective amount of an anthracycline antibiotic (such as epirubicin). In some embodiments, the method is for treatment of breast cancer in a neoadjuvant setting. For example, in some embodiments, there is provided a method of treating locally advanced/inflammatory cancer in an individual comprising administering to the individual 220 mg/m² paclitaxel/albumin nanoparticle composition (such as Abraxane™) every two weeks; 2000 mg/m² gemcitabine, every two weeks; and 50 mg/m² epirubicin, every two weeks. In some embodiments, there is provided a method of treating breast cancer in an individual in an adjuvant setting, comprising administering to the individual 175 mg/m² paclitaxel/albumin nanoparticle composition (such as Abraxane™) every two weeks, 2000 mg/m² gemcitabine, every two weeks, and 50 mg/m² epirubicin, every two weeks.

In some embodiments, there is provided a method of treating a proliferative disease (such as cancer) in an individual, comprising administering to the individual a) an effective amount of a composition comprising nanoparticles comprising a taxane and a carrier protein (such as albumin), b) an effective amount of a platinum-based agent (such as carboplatin), and c) a therapeutic antibody (such as ant-HER2 antibody (such as Herceptin®) and anti-VEGF antibody (such as Avastin®)). In some embodiments, there is provided a method of treating a proliferative disease (such as cancer) in an individual, comprising administering to the individual a) an effective amount of a composition comprising nanoparticles comprising paclitaxel and an albumin (such as Abraxane™), b) an effective amount of a platinum-based agent (such as carboplatin), and c) a therapeutic antibody (such as ant-HER2 antibody (such as Herceptin®) and anti-VEGF antibody (such as Avastin®)). In some embodiments, the method is for treatment of any of advanced breast cancer, metastatic breast cancer, breast cancer in an adjuvant setting, and lung cancer (including NSCLC and advanced NSCLC). In some embodiments, there is provided a method of treating metastatic cancer in an individual, comprising administering to the individual 75 mg/m² paclitaxel/albumin nanoparticle composition (such as Abraxane™) and carboplatin, AUC=2, wherein the administration is carried out weekly for three weeks with the fourth week off. In some embodiments, the method further comprises weekly administering about 2-4 mg/kg of Herception®.

In some embodiments, there is provided a method of treating a proliferative disease (such as cancer) in an individual, comprising administering to the individual a) an effective amount of a composition comprising nanoparticles comprising a taxane and a carrier protein (such as albumin), b) an effective amount of a platinum-based agent (such as carboplatin), and c) a vinca alkaloid (such as Navelbine®). In some embodiments, there is provided a method of treating a proliferative disease (such as cancer) in an individual, comprising administering to the individual a) an effective amount of a composition comprising nanoparticles comprising paclitaxel and an albumin (such as Abraxane™), b) an effective amount of a platinum-based agent (such as carboplatin), and c) a vinca alkaloid (such as Navelbine®). In some embodiments, the method is for treatment of lung cancer.

In some embodiments, the invention provides a method of treating a proliferative disease (such as cancer) in an individual, comprising administering to the individual a) an effective amount of a composition comprising nanoparticles comprising a taxane and a carrier protein (such as albumin), b) an effective amount of an alkylating agent (such as cyclophosphamide) and c) an anthracycline antibiotic (such as adriamycin). In some embodiments, the invention provides a method of treating a proliferative disease (such as cancer) in an individual, comprising administering to the individual a) an effective amount of a composition comprising nanoparticles comprising paclitaxel and an albumin, b) an effective amount of an alkylating agent (such as cyclophosphamide) and c) an anthracycline antibiotic (such as adriamycin). In some embodiments, the method is for treatment of an early stage breast cancer. In some embodiments, the method is for treatment of a breast cancer in an adjuvant or a neoadjuvant setting. For example, in some embodiments, there is provided a method of treating an early stage breast cancer in an individual, comprising administering 260 mg/m² paclitaxel/albumin nanoparticle composition (such as Abraxane™), 60 mg/m² adriamycin, and 600 mg/m² cyclophosphamide, wherein the administration is carried out once every two weeks.

Other embodiments are provided in Table 1. For example, in some embodiments, there is provided a method of treating advanced breast cancer in an individual, comprising administering to the individual a) an effective amount of a composition comprising nanoparticles comprising a paclitaxel and an albumin (such as Abraxane™), b) an effective amount of carboplatin. In some embodiments, the method further comprises administering an effective amount of Herceptin® to the individual. In some embodiments, there is provided a method of treating metastatic breast cancer in an individual, comprising administering to the individual a) an effective amount of a composition comprising nanoparticles comprising paclitaxel and an albumin (such as Abraxane™), b) an effective amount of gemcitabine. In some embodiments, there is provided a method of treating advanced non-small cell lung cancer in an individual, comprising administering to the individual a) an effective amount of a composition comprising nanoparticles comprising paclitaxel and an albumin (such as Abraxane™), b) an effective amount of carboplatin.

In some embodiments, there is provided a composition comprising nanoparticles comprising a taxane (such as paclitaxel, docetaxel, or ortataxel) and a carrier protein (such as albumin) and at least one other chemotherapeutic agent. The compositions described herein may comprise effective amounts of the taxane and the chemotherapeutic agent for the treatment of a proliferative disease (such as cancer). In some embodiments, the chemotherapeutic agent and the taxane are present in the composition at a predetermined ratio, such as the weight ratios described herein. In some embodiments, the invention provides a synergistic composition of an effective amount of a composition comprising nanoparticles comprising a taxane (such as paclitaxel, docetaxel, or ortataxel) and an effective amount of at least one other chemotherapeutic agent.

In some embodiments, the invention provides pharmaceutical compositions comprising nanoparticles comprising a taxane and a carrier protein (such as albumin) for use in the treatment of a proliferative disease (such as cancer), wherein said use comprises simultaneous and/or sequential administration of at least one other chemotherapeutic agent. In some embodiments, the invention provides a pharmaceutical composition comprising a chemotherapeutic agent for use in the treatment of a proliferative disease (such as cancer), wherein said use comprises simultaneous and/or sequential administration of a composition comprising nanoparticles comprising a taxane and a carrier protein (such as albumin). In some embodiments, the invention provides taxane-containing nanoparticle compositions and compositions comprising one other chemotherapeutic agent for simultaneous, and/or sequential use for treatment of a proliferative disease (such as cancer).

Modes of Administration

The composition comprising nanoparticles comprising taxane (also referred to as "nanoparticle composition") and the chemotherapeutic agent can be administered simultaneously (i.e., simultaneous administration) and/or sequentially (i.e., sequential administration).

In some embodiments, the nanoparticle composition and the chemotherapeutic agent (including the specific chemotherapeutic agents described herein) are administered simultaneously. The term "simultaneous administration," as used herein, means that the nanoparticle composition and the chemotherapeutic agent are administered with a time separation of no more than about 15 minute(s), such as no more than about any of 10, 5, or 1 minutes. When the drugs are administered simultaneously, the drug in the nanoparticles and the chemotherapeutic agent may be contained in the same composition (e.g., a composition comprising both the nanoparticles and the chemotherapeutic agent) or in separate compositions (e.g., the nanoparticles are contained in one composition and the chemotherapeutic agent is contained in another composition). For example, the taxane and the chemotherapeutic agent may be present in a single composition containing at least two different nanoparticles, wherein some of the nanoparticles in the composition comprise the taxane and a carrier protein, and some of the other nanoparticles in the composition comprise the chemotherapeutic agent and a carrier protein. The invention contemplates and encompasses such compositions. In some embodiments, only the taxane is contained in nanoparticles. In some embodiments, simultaneous administration of the drug in the nanoparticle composition and the chemotherapeutic agent can be combined with supplemental doses of the taxane and/or the chemotherapeutic agent.

In some embodiments, the nanoparticle composition and the chemotherapeutic agent are administered sequentially. The term "sequential administration" as used herein means that the drug in the nanoparticle composition and the chemotherapeutic agent are administered with a time separation of more than about 15 minutes, such as more than about any of 20, 30, 40, 50, 60 or more minutes. Either the nanoparticle composition or the chemotherapeutic agent may be administered first. The nanoparticle composition and the chemotherapeutic agent are contained in separate compositions, which may be contained in the same or different packages.

In some embodiments, the administration of the nanoparticle composition and the chemotherapeutic agent are concurrent, i.e., the administration period of the nanoparticle composition and that of the chemotherapeutic agent overlap with each other. In some embodiments, the administration of the nanoparticle composition and the chemotherapeutic agent are non-concurrent. For example, in some embodiments, the administration of the nanoparticle composition is terminated before the chemotherapeutic agent is administered. In some embodiments, the administration of the chemotherapeutic agent is terminated before the nanoparticle composition is administered. The time period between these two non-concurrent administrations can range from about two to eight weeks, such as about four weeks.

The dosing frequency of the drug-containing nanoparticle composition and the chemotherapeutic agent may be adjusted over the course of the treatment, based on the judgment of the administering physician. When administered separately, the drug-containing nanoparticle composition and the chemotherapeutic agent can be administered at different dosing frequency or intervals. For example, the drug-containing nanoparticle composition can be administered weekly, while a chemotherapeutic agent can be administered more or less frequently. In some embodiments, sustained continuous release formulation of the drug-containing nanoparticle and/or chemotherapeutic agent may be used. Various formulations and devices for achieving sustained release are known in the art.

The nanoparticle composition and the chemotherapeutic agent can be administered using the same route of administration or different routes of administration. In some embodiments (for both simultaneous and sequential administrations), the taxane in the nanoparticle composition and the chemotherapeutic agent are administered at a predetermined ratio. For example, in some embodiments, the ratio by weight of the taxane in the nanoparticle composition and the chemotherapeutic agent is about 1 to 1. In some embodiments, the weight ratio may be between about 0.001 to about 1 and about 1000 to about 1, or between about 0.01 to about 1 and 100 to about 1. In some embodiments, the ratio by weight of the taxane in the nanoparticle composition and the chemotherapeutic agent is less than about any of 100:1, 50:1, 30:1, 10:1, 9:1, 8:1, 7:1, 6:1, 5:1, 4:1, 3:1, 2:1, and 1:1 In some embodiments, the ratio by weight of the taxane in the nanoparticle composition and the chemotherapeutic agent is more than about any of 1:1, 2:1, 3:1, 4:1, 5:1, 6:1, 7:1, 8:1, 9:1, 30:1, 50:1, 100:1. Other ratios are contemplated.

The doses required for the taxane and/or the chemotherapeutic agent may (but not necessarily) be lower than what is normally required when each agent is administered alone. Thus, in some embodiments, a subtherapeutic amount of the drug in the nanoparticle composition and/or the chemotherapeutic agent are administered. "Subtherapeutic amount" or "subtherapeutic level" refer to an amount that is less than the therapeutic amount, that is, less than the amount normally used when the drug in the nanoparticle composition and/or the chemotherapeutic agent are administered alone. The reduction may be reflected in terms of the amount administered at a given administration and/or the amount administered over a given period of time (reduced frequency).

In some embodiments, enough chemotherapeutic agent is administered so as to allow reduction of the normal dose of the drug in the nanoparticle composition required to effect the same degree of treatment by at least about any of 5%, 10%, 20%, 30%, 50%, 60%, 70%, 80%, 90%, or more. In some embodiments, enough drug in the nanoparticle composition is administered so as to allow reduction of the normal dose of the chemotherapeutic agent required to effect the same degree of treatment by at least about any of 5%, 10%, 20%, 30%, 50%, 60%, 70%, 80%, 90%, or more.

In some embodiments, the dose of both the taxane in the nanoparticle composition and the chemotherapeutic agent are reduced as compared to the corresponding normal dose of each when administered alone. In some embodiments, both the taxane in the nanoparticle composition and the chemotherapeutic agent are administered at a subtherapeutic, i.e., reduced, level. In some embodiments, the dose of the nanoparticle composition and/or the chemotherapeutic agent is substantially less than the established maximum toxic dose (MTD). For example, the dose of the nanoparticle composition and/or the chemotherapeutic agent is less than about 50%, 40%, 30%, 20%, or 10% of the MTD.

A combination of the administration configurations described herein can be used. The combination therapy methods described herein may be performed alone or in conjunction with another therapy, such as surgery, radiation, chemotherapy, immunotherapy, gene therapy, and the like. Additionally, a person having a greater risk of developing the proliferative disease may receive treatments to inhibit or and/or delay the development of the disease.

As will be understood by those of ordinary skill in the art, the appropriate doses of chemotherapeutic agents will be approximately those already employed in clinical therapies wherein the chemotherapeutic agent are administered alone or in combination with other chemotherapeutic agents. Variation in dosage will likely occur depending on the condition being treated. As described above, in some embodiments, the chemotherapeutic agents may be administered at a reduced level.

The nanoparticle compositions described herein can be administered to an individual (such as human) via various routes, such as parenterally, including intravenous, intra-arterial, intraperitoneal, intrapulmonary, oral, inhalation, intravesicular, intramuscular, intra-tracheal, subcutaneous, intraocular, intrathecal, or transdermal. For example, the nanoparticle composition can be administered by inhalation to treat conditions of the respiratory tract. The composition can be used to treat respiratory conditions such as pulmonary fibrosis, broncheolitis obliterans, lung cancer, bronchoalveolar carcinoma, and the like. In some embodiments, the nanoparticle composition is administrated intravenously. In some embodiments, the nanoparticle composition is administered orally.

The dosing frequency of the administration of the nanoparticle composition depends on the nature of the combination therapy and the particular disease being treated. An exemplary dosing frequency include, but is not limited to, weekly without break; weekly, three out of four weeks; once every three weeks; once every two weeks; weekly, two out of three weeks. See also Table 1.

The dose of the taxane in the nanoparticle composition will vary with the nature of the combination therapy and the particular disease being treated. The dose should be sufficient to effect a desirable response, such as a therapeutic or prophylactic response against a particular disease. An exemplary dose of the taxane (in some embodiments paclitaxel) in the nanoparticle composition include, but is not limited to, about any of 50 mg/m$^2$, 60 mg/m$^2$, 75 mg/m$^2$, 80 mg/m$^2$, 90 mg/m$^2$, 100 mg/m$^2$, 120 mg/m$^2$, 160 mg/m$^2$, 175 mg/m$^2$, 200 mg/m$^2$, 210 mg/m$^2$, 220 mg/m$^2$, 260 mg/m$^2$, and 300 mg/m$^2$. For example, the dosage of paclitaxel in a nanoparticle composition can be in the range of 100-400 mg/m$^2$ when given on a 3 week schedule, or 50-250 mg/m$^2$ when given on a weekly schedule. See also Table 1.

Other exemplary dosing schedules for the administration of the nanoparticle composition (such as paclitaxel/albumin nanoparticle composition, for example Abraxane™) include, but are not limited to, 100 mg/m$^2$, weekly, without break; 75 mg/m$^2$ weekly, 3 out of four weeks; 100 mg/m$^2$, weekly, 3 out of 4 weeks; 125 mg/m$^2$, weekly, 3 out of 4 weeks; 125 mg/m$^2$, weekly, 2 out of 3 weeks; 130 mg/m$^2$, weekly, without break; 175 mg/m$^2$, once every 2 weeks; 260 mg/m$^2$, once every 2 weeks; 260 mg/m$^2$, once every 3 weeks; 180-300 mg/m$^2$, every three weeks; 60-175 mg/m$^2$, weekly, without break. In addition, the taxane (alone or in combination therapy) can be administered by following a metronomic dosing regime described herein.

Exemplary dosing regimes for the combination therapy of nanoparticle composition (such as paclitaxel/albumin nanoparticle composition, for example Abraxane™) and other agents include, but are not limited to, 125 mg/m$^2$ weekly, two out of three weeks, plus 825 mg/m$^2$ Xeloda®, daily; 260 mg/m$^2$ once every two weeks, plus 60 mg/m$^2$ adriamycin and 600 mg/m$^2$ cyclophosphamide, once every two weeks; 220-340 mg/m$^2$ once every three weeks, plus carboplatin, AUC=6, once every three weeks; 100-150 mg/m$^2$ weekly, plus carboplatin, AUC=6, once every three weeks; 175 mg/m$^2$ once every two weeks, plus 2000 mg/m$^2$ gemcitabine and 50 mg/m$^2$ epirubicin, once every two weeks; and 75 mg/m$^2$ weekly, three out of four weeks, plus carboplatin, AUC=2, weekly, three out of four weeks.

In some embodiments, the nanoparticle composition of the taxane and the chemotherapeutic agent is administered according to any of the dosing regimes described in Table 1.

In some embodiments, there is provided a method of treating breast cancer in an individual comprising administering to the individual: a) an effective amount of a composition comprising nanoparticles comprising a taxane (such as paclitaxel) and an albumin, and b) an effective amount of at least one other chemotherapeutic agent as provided in Rows 1 to 35 in Table 1. In some embodiments, the administration of the nanoparticle composition and the chemotherapeutic agent may be any of the dosing regimes as indicated in Rows 1 to 35 in Table 1. In some embodiments, there is provided a method of treating metastatic breast cancer in an individual comprising administering to the individual: a) an effective amount of a composition comprising nanoparticles comprising a taxane (such as paclitaxel) and an albumin, and b) an effective amount of at least one other chemotherapeutic agent as provided in Rows 2, 4-8, and 10-15 in Table 1. In some embodiments, the administration of the nanoparticle composition and the chemotherapeutic agent may be any of the dosing regimes as indicated in Rows 2, 4-8, and 10-15 in Table 1.

In some embodiments, there is provided a method of treating advanced breast cancer in an individual comprising administering to the individual: a) an effective amount of a composition comprising nanoparticles comprising a taxane (such as paclitaxel) and an albumin, and b) an effective amount of at least one other chemotherapeutic agent as provided in Rows 1 and 16 in Table 1. In some embodiments, the administration of the nanoparticle composition and the chemotherapeutic agent may be any of the dosing regimes as indicated in Rows 1 and 16 in Table 1. In some embodiments, there is provided a method of treating stage IV breast cancer in an individual comprising administering to the individual: a) an effective amount of a composition comprising nanoparticles comprising a taxane (such as paclitaxel) and an albumin, and b) an effective amount of at least one other chemotherapeutic agent as provided in Row 3 in Table 1. In some embodiments, the administration of the nanoparticle composition and the chemotherapeutic agent may be the dosing regime as indicated in Row 3 in Table 1.

In some embodiments, there is provided a method of treating breast cancer in an individual in an adjuvant setting comprising administering to the individual: a) an effective amount of a composition comprising nanoparticles comprising a taxane (such as paclitaxel) and an albumin, and b) an effective amount of at least one other chemotherapeutic agent as provided in Rows 18 to 24 in Table 1. In some embodiments, the administration of the nanoparticle composition and the chemotherapeutic agent may be any of the dosing regimes as indicated in Rows 18 to 24 in Table 1.

In some embodiments, there is provided a method of treating breast cancer in an individual in a neoadjuvant setting comprising administering to the individual: a) an effective amount of a composition comprising nanoparticles comprising a taxane (such as paclitaxel) and an albumin, and b) an effective amount of at least one other chemotherapeutic agent as provided in Rows 25 to 35 in Table 1. In some embodiments, the administration of the nanoparticle composition and the chemotherapeutic agent may be any of the dosing regimes as indicated in Rows 25 to 35 in Table 1.

In some embodiments, there is provided a method of treating lung cancer in an individual comprising administering to the individual: a) an effective amount of a composition comprising nanoparticles comprising a taxane (such as paclitaxel) and an albumin, and b) an effective amount of at least one other chemotherapeutic agent as provided in Rows 36 to 48 in Table 1. In some embodiments, the administration of the nanoparticle composition and the chemotherapeutic agent may be any of the dosing regimes as indicated in Rows 36 to 48 in Table 1.

In some embodiments, there is provided a method of treating NSCLC (including advanced NSCLC and first line NSCLC) in an individual comprising administering to the individual: a) an effective amount of a composition comprising nanoparticles comprising a taxane (such as paclitaxel) and an albumin, and b) an effective amount of at least one other chemotherapeutic agent as provided in Rows 36-40 and 42-43 in Table 1. In some embodiments, the administration of the nanoparticle composition and the chemotherapeutic agent may be any of the dosing regimes as indicated in Rows 36-40 and 42-43 in Table 1. In some embodiments, there is provided a method of treating advanced solid tumor malignancy in the lung in an individual comprising administering to the individual: a) an effective amount of a composition comprising nanoparticles comprising a taxane (such as paclitaxel) and an albumin, and b) an effective amount of at least one other chemotherapeutic agent as provided in Row 41 in Table 1. In some embodiments, the administration of the nanoparticle composition and the chemotherapeutic agent may be the dosing regimes as indicated in Row 41 in Table 1. In some embodiments, there is provided a method of treating SCLC in an individual comprising administering to the individual: a) an effective amount of a composition comprising nanoparticles comprising a taxane (such as paclitaxel) and an albumin, and b) an effective amount of at least one other chemotherapeutic agent as provided in Row 48 in Table 1. In some embodiments, the administration of the nanoparticle composition and the chemotherapeutic agent may be the dosing regimes as indicated in Row 48 in Table 1.

In some embodiments, there is provided a method of treating ovarian cancer in an individual comprising administering to the individual: a) an effective amount of a composition comprising nanoparticles comprising a taxane (such as paclitaxel) and an albumin, and b) an effective amount of at least one other chemotherapeutic agent as provided in Rows 49 to 52 in Table 1. In some embodiments, the administration of the nanoparticle composition and the chemotherapeutic agent may be any of the dosing regimes as indicated in Rows 49 to 52 in Table 1.

In some embodiments, there is provided a method of treating head and neck cancer in an individual comprising administering to the individual: a) an effective amount of a composition comprising nanoparticles comprising a taxane (such as paclitaxel) and an albumin, and b) an effective amount of at least one other chemotherapeutic agent as provided in Rows 53 to 55 in Table 1. In some embodiments, the administration of the nanoparticle composition and the chemotherapeutic agent may be any of the dosing regimes as indicated in Rows 53 to 55 in Table 1.

In some embodiments, there is provided a method of treating solid tumor (including advanced solid tumor) in an individual comprising administering to the individual: a) an effective amount of a composition comprising nanoparticles comprising a taxane (such as paclitaxel) and an albumin, and b) an effective amount of at least one other chemotherapeutic agent as provided in Rows 56 to 59 in Table 1. In some embodiments, the administration of the nanoparticle composition and the chemotherapeutic agent may be any of the dosing regimes as indicated in Rows 56 to 59 in Table 1.

In some embodiments, there is provided a method of treating melanoma (including metastatic melanoma) in an individual comprising administering to the individual: a) an effective amount of a composition comprising nanoparticles comprising a taxane (such as paclitaxel) and an albumin, and b) an effective amount of at least one other chemotherapeutic agent as provided in Rows 60-63 in Table 1. In some embodiments, the administration of the nanoparticle composition and the chemotherapeutic agent may be any of the dosing regimes as indicated in Rows 60 to 63 in Table 1.

In some embodiments, there is provided a method of treating metastatic colorectal cancer in an individual comprising administering to the individual: a) an effective amount of a composition comprising nanoparticles comprising a taxane (such as paclitaxel) and an albumin, and b) an effective amount of at least one other chemotherapeutic agent as provided in Row 64 in Table 1. In some embodiments, the administration of the nanoparticle composition and the chemotherapeutic agent may be the dosing regime as indicated in Row 64 in Table 1.

In some embodiments, there is provided a method of treating pancreatic cancer in an individual comprising administering to the individual: a) an effective amount of a composition comprising nanoparticles comprising a taxane (such as paclitaxel) and an albumin, and b) an effective amount of at least one other chemotherapeutic agent as provided in Rows 65 to 66 in Table 1. In some embodiments, the administration of the nanoparticle composition and the chemotherapeutic agent may be any of the dosing regimes as indicated in Rows 65 to 66 in Table 1.

TABLE 1

| Row No. | Combination | Regime/Dosage | Study therapy type | Protocol title |
|---|---|---|---|---|
| 1. | ABX + Carboplatin + Herceptin ® | ABX: 100 mg/m$^2$ D1, 8, 15 q4wk × 6<br>Carbo: AUC = 2 D1, 8, 15 q4wk × 6<br>Herceptin ®: 4 mg/kg on wk 1, 2 mg/kg all subsequent weeks | Advanced HER2+ Breast Cancer | A phase II study of weekly dose-dense nanoparticle paclitaxel (ABI-007) carboplatin ™, with Herceptin ® as first or second-line therapy of advanced HER2+ breast cancer |
| 2. | ABX alone (+Herceptin ®) | ABX: 125 mg/m$^2$ qwk × 3/4 | Metastatic Breast Cancer | Phase II trial of weekly Abraxane ™ monotherapy for 1st-line MBC (plus Herceptin ® in HER2+ pts) |
| 3. | ABX + Navelbine ® (±G-CSF) | L1: ABX: 80 mg/m Nav: 15 mg/m$^2$<br>L2: ABX: 90 mg/m$^2$ Nav: 20 mg/m$^2$<br>L3: ABX: 100 mg/m$^2$ Nav: 22.5 mg/m$^2$<br>L4: ABX: 110 mg/m$^2$ Nav: 25 mg/m$^2$<br>L5: ABX: 125 mg/m$^2$ Nav: 25 mg/m$^2$<br>qwk all levels | Stage IV Breast Cancer | Phase I-II study weekly ABX + Navelbine ®, with or without G-CSF, in stage IV breast cancer |
| 4. | ABX + Xeloda ® | ABX: 125 mg/m$^2$ qwk × 2/3<br>Xeloda ®: 825 mg/m$^2$ D1-14 q3wk | Metastatic Breast Cancer | Phase II 1st-line ABX + Xeloda ® MBC trial |
| 5. | ABX + Anthracycline | | Metastatic Breast Cancer | Phase I/II trial ABX plus Doxil ® for MBC plus limited PK |
| 6. | ABX + Gemcitabine | ABX: 125 mg/m$^2$<br>Gem: 1000 mg/m2<br>qwk × 2/3 | Metastatic Breast Cancer | Randomized Phase II Trial of Weekly nab (nanoparticle albumin bound)-Paclitaxel (nab-paclitaxel) in Combination with Gemcitabine in Patients with HER2 Negative Metastatic Breast Cancer |
| 7. | ABX + Lapatinib | | Metastatic Breast Cancer | Phase I/II Abraxane ™ + GW572016 |
| 8. | ABX + Lapatinib | ABX: 100 mg/m$^2$ qwk × 3/4<br>Lapatinib: starting at 1000 mg/d × 2 days | Metastatic Breast Cancer | Phase I dose escalation study of a 2 day oral lapatinib chemosensitization pulse given prior to weekly intravenous Abraxane ™ in patients with advanced solid tumors |
| 9. | ABX + FEC (+Herceptin ®) | ABX: 220 mg/m$^2$ q2wk × 6 followed by<br>FEC: 4 cycles (+Herceptin ® for HER2 + pts) | Breast Cancer | Phase II preoperative trial of Abraxane ™ followed by FEC (+Herceptin ® as appropriate) in breast cancer |
| 10. | ABX + Carboplatin + Avastin ® | ABX: 100 mg/m$^2$ qwk D1, 8, 15<br>Carbo: AUC = 2 qwk D1, 8, 15<br>Avastin ®: 10 mg/m$^2$ q2wk | Metastatic Breast Cancer (HER2−, ER−, PR−) | Phase II safety and tolerability study of Abraxane ™, Avastin ® and carboplatin in triple negative metastatic breast cancer patients |
| 11. | ABX + Avastin ® | ABX: 130 mg/m$^2$ qwk + Avastin ® vs<br>ABX: 260 mg/m$^2$ q2wk + Avastin ® vs<br>ABX: 260 mg/m$^2$ q3wk + Avastin ® | Metastatic Breast Cancer | Three arm phase II trial in 1$^{st}$ line HER2− negative MBC patients |
| 12. | ABX + Avastin ® | ABX: 125 mg/m$^2$ qwk × 3/4 + Avastin ® | Metastatic Breast Cancer | Single arm study of Abraxane ™ and Avastin ® in 1$^{st}$ line MBS |
| 13. | ABX + Avastin ® | ABX + Avastin ® qwk vs<br>Taxol ® + Avastin ® qwk | Metastatic Breast Cancer | Randomized Phase III trial in 1$^{st}$ line and 2$^{nd}$ line MBC with |

TABLE 1-continued

| Row No. | Combination | Regime/Dosage | Study therapy type | Protocol title |
|---|---|---|---|---|
| 14. | ABX + Xeloda ® + Lapatinib | | Metastatic Breast Cancer | biological correlates analysis Phase II Abraxane ™ in combination with Xeloda ® and Lapatinib for metastatic breast cancer |
| 15. | ABX + Gemcitabine | ABX: 3000 mg/m² D1 q3wk<br>Gem: 1250 mg/m² D1, 8 q3wk | Metastatic Breast Cancer | Single arm Phase II study of Abraxane ™ and gemcitabine for 1st line MBC |
| 16. | ABX + RAD001 | | Advanced Breast Cancer | Phase I/II study of Abraxane ™ in combination with RAD001 in patients with advanced breast cancer |
| 17. | ABX + Sutent ® | | Breast Cancer | Phase I study of Abraxane ™ in combination with Sutent ® |
| 18. | ABX + AC + G-CSF (+Herceptin ®) | AC + G-CSF q2wk × 4 followed by ABX: 260 mg/m² q2wk × 4 (+Herceptin ® for HER2+ pts) | Breast Cancer-Adjuvant | Abraxane ™ in dose-dense adjuvant chemotherapy for early stage breast cancer |
| 19. | ABX + AC + G-CSF (+Herceptin ®) | Dose dense AC + G-CSF followed by ABX (+Herceptin ® for HER2 + pts) qwk | Breast Cancer-Adjuvant | Phase II pilot adjuvant trial of Abraxane ™ in breast cancer |
| 20. | ABX + AC | AC followed by ABX: 260 mg/m² vs AC followed by Taxol ® Rx length 16 wks | Breast Cancer-Adjuvant | Adjuvant Dose dense Registrational Trial |
| 21. | ABX + AC (+G-CSF) | AC q2wk followed by ABX: 260 mg/m² + G-CSF q2wk Rx length 16 wks | Breast Cancer-Adjuvant | Phase II dose dense pilot adjuvant study of Abraxane ™ in breast cancer |
| 22. | ABX + AC (+Avastin ®) | Dose dense AC followed by ABX (+Avastin ® in HER2+ pts) | Breast Cancer-Adjuvant | Pilot adjuvant breast cancer study |
| 23. | ABX + AC | AC followed by ABX q2wk or q3wk | Breast Cancer-Adjuvant | BIG study: Dose dense vs standard adjuvant chemotherapy |
| 24. | ABX (ABI-007) + AC + Neulasta ® | AC followed by ABX q2wk × 4 | Breast Cancer - Adjuvant | Phase II - Pilot Study Evaluating the Safety of a Dose-Dense Regime - AC × 4 => ABI-007 × 4 Q 2 WEEKS + Neulasta ® - Given as Adjuvant Chemotherapy of High-Risk Women with Early Breast Cancer |
| 25. | ABX + FEC (+Herceptin ®) | ABX: 100 mg/m² qwk × 12 followed by 5-FU: 500 mg/m² q3wk Epirubicin: 100 mg/m² (without Herceptin ®) or Epirubicin: 75 mg/m² (with Herceptin ® for HER2+ pts) Cyclophosphamide: 500 mg/m² q3wk | Locally Advanced Breast Cancer-Neoadjuvant | A Phase II Study of Neoadjuvant Chemotherapy with Sequential Weekly Nanoparticle Albumin Bound Paclitaxel (Abraxane ™) Followed by 5-Fluorouracil, Epirubicin, Cyclophosphamide (FEC) in Locally Advanced Breast Cancer |
| 26. | ABX + Gemcitabine + Epirubicin | Arm 1: Neoadjuvant: Gem: 2000 mg/m², ABX: 175 mg/m², Epi 50 mg/m² q2wk × 6 Arm 2: Adjuvant: Gem: 2000 mg/m², ABX: 220 mg/m² q2wk × 4 | Breast Cancer - Neoadjuvant | Phase II Trial of Dose Dense Neoadjuvant Gemcitabine, Epirubicin, ABI-007 (GEA) in Locally Advanced or Inflammatory Breast Cancer |
| 27. | ABX + Herceptin ® | ABX: 260 mg/m² q2wk + Herceptin ® followed by Navelbine ® + Herceptin ® | Breast Cancer - Neoadjuvant | Phase II Multi-center study neoadjuvant. |

TABLE 1-continued

| Row No. | Combination | Regime/Dosage | Study therapy type | Protocol title |
|---|---|---|---|---|
| 28. | ABX + Carboplatin (+Herceptin ®) + AC | TAC vs AC followed by ABX + carbo vs AC followed by ABX + carbo + Herceptin ® | Breast Cancer - Neoadjuvant | 3 arms Randomized dose dense phase II trial of neoadjuvant chemotherapy in patients with breast cancer |
| 29. | ABX + Capecitabine | ABX: 260 mg/m$^2$ q3wk × 4 Xeloda ® 850 mg/m$^2$ D1-14 q3wk × 4 | Breast Cancer - Neoadjuvant | Phase II neoadjuvant trial of Abraxane ™ and capecitabine in locally advanced breast cancer |
| 30. | ABX + Carboplatin (+Avastin ®) | ABX qwk carbo qwk + Avastin ® in HER2+ pts | Breast Cancer - Neoadjuvant | Phase I/II trial of neoadjuvant chemotherapy (NCT) with weekly nanoparticle paclitaxel (ABI-007, Abraxane ™) in combination with carboplatin and Avastin ® in clinical stage I-III. |
| 31. | ABX + Carboplatin + Herceptin ® + Avastin ® | ABX: 100 mg/m$^2$ qwk × 3/4 Carbo: AUC = 5 + Herceptin ® + Avastin ® 4 week cycle × 6 | Breast Cancer - Neoadjuvant | Phase II study of weekly bevacizumab administered with weekly trastuzumab, ABI-007, and carboplatin as preoperative therapy in HER2-neu gene amplified breast cancer tumors |
| 32. | ABX + Lapatinib | ABX: 260 mg/m$^2$ q3wk Lapatinib: 1000 mg/day | Breast Cancer - Neoadjuvant | Pilot neoadjuvant trial with combination of ABI-007 (Abraxane ™) and GW572016 (Lapatinib) |
| 33. | ABX + Capecitabine | ABX: 200 mg/m$^2$ q3wk × 4 Xeloda ®: 1000 mg/m$^2$ D1-14 q3wk × 4 | Breast Cancer - Neoadjuvant | Phase II neoadjuvant trail of Abraxane ™ and capecitabine in locally advanced breast cancer |
| 34. | ABX ± Avastin ® + AC (+G-CSF) | ABX qwk ± Avastin ® followed by A qwk + C daily vs Taxol ® qwk ± Avastin ® followed by A qwk + C daily | Breast Cancer - Neoadjuvant | Phase III trial of paclitaxel vs Abraxane ™ with or without Avastin ® in combination with doxorubicin and cyclophosphamide plus G-CSF |
| 35. | ABX + AC | ABX followed by AC | Breast Cancer - Neoadjuvant | Phase II neoadjuvant trial with gene expression analyses |
| 36. | ABX + Carboplatin + Avastin ® | ABX: 300 mg/m$^2$ q3wk Carbo: AUC = 6 q3wk Avastin ®: 15 mg/kg 4 cycles | 1$^{st}$ line Advanced NSCLC | An open label phase II trial of Abraxane ™, carboplatin and Avastin ® in patients with advanced non-squamous non-small cell lung cancer |
| 37. | ABX + Carboplatin | L1: ABX: 225 mg/m$^2$ L2: ABX: 260 mg/m$^2$ L3: ABX: 300 mg/m$^2$ Cohorts 1-4: ABX q3wk Cohorts 5-7: ABX weekly Cohort 8: 75 additional patients Carbo fixed at AUC = 6 q3wk | Advanced NSCLC | Phase II toxicity pilot study of Abraxane ™ and carboplatin in advanced non-small cell lung cancer. |
| 38. | ABX + Carboplatin | Carbo: AUC = 6 + ABX vs Carbo: AUC = 6 + Taxol ®: 225 mg/m$^2$ | 1$^{st}$ line NSCLC | Phase III Registration - NSCLC 1st line therapy |
| 39. | ABX + Carboplatin | ABX: 100 mg/m$^2$ d1, 8, 15 Carbo: AUC = 6 q4wk Amendment: ABX: 125 mg/m$^2$ D1, 8, 15 | 1$^{st}$ line NSCLC | Phase II Trial of weekly Abraxane ™ plus carboplatin in 1st-line NSCLC |
| 40. | ABX + Carboplatin + Avastin ® | Weekly | NSCLC | |
| 41. | ABX + Carboplatin | Arm 1: ABX: 100, 125, 150 mg/m$^2$ D1, 8, 15 q4wk Arm 2: ABX 220, 260, 300, 340 mg/m$^2$ q3wk Arm 3: ABX 100, 125, 150 mg/m$^2$ | Lung Cancer - Advanced Soild Tumor Malignancy | Phase I Trial of carboplatin and Abraxane ™ on a weekly and every three week schedule in |

TABLE 1-continued

| Row No. | Combination | Regime/Dosage | Study therapy type | Protocol title |
|---|---|---|---|---|
| | | D1, 8<br>Carbo: AUC = 6 in all arms | | patients with Advanced Soild Tumor Malignancies |
| 42. | ABX + Gemcitabine<br>or<br>ABX + Avastin ® | | NSCLC | Abraxane ™ in combination with gemcitabine or Avastin ® |
| 43. | ABX + Gemcitabine | | NSCLC | Phase I trial of Abraxane ™ in combination with gemcitabine |
| 44. | ABX + Carboplatin + Avastin ® | ABX: 225, 260, 300 mg/m$^2$<br>Carbo: AUC = 6<br>q3wk + Avastin ® | Lung Cancer | Phase I/II study of Abraxane ™ and carboplatin AUC 6, plus Avastin ® (Standard 3 + 3 Phase I design; PhII: 40 pts) |
| 45. | ABX + Alimta ® | ABX: 220, 260, 300 mg/m$^2$ q3wk<br>Pemtrexed: 500 mg q3wk | Lung Cancer | Phase I/II study of Abraxane ™ + Alimta ® for 2nd-line NSCLC |
| 46. | ABX + Cisplatin | | Lung Cancer | Phase I/II trial of Abraxane ™ plus cisplatin in advanced NSCLC |
| 47. | ABX + Navelbine ® + Cisplatin | | Lung Cancer | Phase I/II study of Abraxane ™, Navelbine ®, and Cisplatin for treatment of advanced NSCLC |
| 48. | ABX + Carboplatin | ABX: 300 mg/m$^2$ q3wk<br>Carbo: AUC = 6 q3wk | SCLC | Phase II trial of Abraxane ™ and carboplatin in extensive stage small cell lung cancer |
| 49. | ABX + Carboplatin | ABX: 100 mg/m$^2$ qwk × 3/4<br>Carbo: AUC = 6 | Ovarian Cancer | A phase II trial of Abraxane ™ + Carboplatin in recurrent ovarian cancer |
| 50. | ABX + Carboplatin | ABX: qwk<br>ABX: q3w<br>Carbo: AUC = 6 both arms | Ovarian Cancer | Phase I study of Abraxane ™ plus carbo for treatment of advanced ovarian cancer |
| 51. | ABX + Carboplatin | ABX: TBD by ABI-CA034<br>vs<br>Taxol ® 175 mg/m$^2$<br>Carbo: AUC = 6 in both arms | Ovarian Cancer | 1st line, optimally debulked, registration trial. Carbo AUC 6 + ABX vs Carbo + Taxol ® 175 mg/m$^2$. Endpoint: relapse free survival, survival |
| 52. | ABX + Avastin ® | ABX: 100 mg/m$^2$ qwk × 3/4<br>Avastin ®: 10 mg/m$^2$ q2wk | Ovarian Cancer | Phase II study of bevacizumab with Abraxane ™ in patients with recurrent, platinum resistant primary epithelial ovarian or primary peritoneal carcinoma |
| 53. | ABX + 5-FU + Cisplatin | ABX: D1<br>5-FU: 750 mg/m$^2$ CIV × 5<br>cisplatin: 75 mg/m$^2$ D1<br>followed by XRT/surgery | Head and Neck Cancer | Unresectable localized head and neck cancer Phase II Abraxane ™ in combination with 5-FU and cisplatin |
| 54. | ABX + 5-FU + Cisplatin | 5-FU: 750 mg/m$^2$ CIV × 5<br>cisplatin: 75 mg/m$^2$ D1 ± ABX D1<br>followed by XRT/surgery | Head and Neck Cancer | Unresectable localized head and neck cancer Phase III 5-FU and cisplatin with or without Abraxane ™ |
| 55. | ABX + Cetuximab | | Head and Neck Cancer | Phase II multicenter trial of Abraxane ™ in combination with cetuximab in 1$^{st}$ line treatment of locally advanced or metastatic head and neck cancer |
| 56. | ABX + Rapamycin | ABX: 100 mg/m$^2$ qwk<br>Rapamycin: 5-40 mg dose | Solid Tumors | Phase I Study of Rapamycin in |

TABLE 1-continued

| Row No. | Combination | Regime/Dosage | Study therapy type | Protocol title |
|---|---|---|---|---|
| | | escalation | | Combination with Abraxane ™ in Advanced Solid Tumors |
| 57. | ABX + Satraplatin | | Solid Tumors | Phase I trial of Abraxane ™ and Satraplatin |
| 58. | ABX + Gemcitabine | ABX: 180, 220, 260, 300, 340 mg/m$^2$ q3wk<br>Gemcitabine: 1000 mg/m$^2$ D1 and D8 | Advanced Solid Tumors | Phase I Trial of Abraxane ™ in combination with Gemcitabine |
| 59. | ABX + Gefitinib | ABX: 100 mg/m$^2$ qwk × 3/4<br>Gefitinib starting at 1000 mg/d × 2 | Advanced Solid Tumors | Phase I dose escalation study of gefitinib chemosensitization pulse given prior to weekly Abraxane ™ |
| 60. | ABX + Avastin ® | | Metastatic Melanoma | Phase II study of Abraxane ™ and Avastin ® in metastatic melanoma |
| 61. | ABX + Avastin ® | | Melanoma | Abraxane ™ and Avastin ® as therapy for patients with malignant melanoma |
| 62. | ABX + Carboplatin | | Metastatic Melanoma | Phase II study of Abraxane ™ and carboplatin in metastatic melanoma |
| 63. | ABX + Sorafenib + Carboplatin | ABX: qwk<br>Sorafenib: D2-19<br>Carbo: AUC = 6 D1 | Metastatic Melanoma | Phase II study of Abraxane ™ in combination with carboplatin and sorafenib in metastatic melanoma |
| 64. | ABX + Capecitabine | | Metastatic Colorectal Cancer (after failure of oxaliplatin-based therapy and irinotecan-based therapy) | Phase II trial of Abraxane ™ in combination with Xeloda ® for previously treated patient with advance or metastatic colorectal cancer |
| 65. | ABX + Gemcitabine | Weekly | Pancreatic Cancer | Phase I study of Abraxane ™ in combination with gemcitabine in pancreatic cancer |
| 66. | ABX + Gemcitabine | ABX + Gem vs Gem | Pancreatic Cancer | Phase III registration trial in pancreatic cancer |
| 67. | ABX + anti-angiogenic agents | | | Abraxane ™ combined with anti-angiogenic agents, e.g. Avastin ® |
| 68. | ABX + proteasome inhibitors | | | Abraxane ™ combined with proteasome inhibitors, e.g Velcade ® |
| 69. | ABX + EGFR inhibitors | | | Abraxane ™ combined with EGFR inhibitors, e.g. Tarceva ® |

As used in herein (for example in Table 1), ABX refers to Abraxane™; GW572016 refers to lapatinib; Xel refers to capecitabine or Xeloda®; bevacizumab is also known as Avastin®; trastuzumab is also known as Herceptin®; pemtrexed is also known as Alimta®; cetuximab is also known as Erbitux®; gefitinib is also known as Iressa®; FEC refers to a combination of 5-fluorouracil, Epirubicin and Cyclophosphamide; AC refers to a combination of Adriamycin plus Cyclophosphamide; TAC refers to a FDA approved adjuvant breast cancer regime; RAD001 refers to a derivative of rapamycin; NSCLC refers to non-small cell lung cancer; and SCLC refers to small cell lung cancer.

As used herein (for example in Table 1), AUC refers to area under curve; q4wk refers to a dose every 4 weeks; q3wk refers to a dose every 3 weeks; q2wk refers to a dose every 2 weeks; qwk refers to a weekly dose; qwk×3/4 refers to a weekly dose for 3 weeks with the 4$^{th}$ week off; qwk×2/3 refers to a weekly dose for 2 weeks with the 3$^{rd}$ week off.

Combination Therapy with Radiation Therapy and Surgery

In another aspect, the present invention provides a method of treating proliferative disease (such as cancer) comprising a first therapy comprising administering a taxane (particularly nanoparticles comprising a taxane) and a carrier protein and a second therapy comprising radiation and/or surgery.

In some embodiments, the method comprises: a) a first therapy comprising administering to the individual a composition comprising nanoparticles comprising an effective amount of a taxane and a carrier protein (such as albumin) and b) a second therapy comprising radiation therapy, surgery, or combinations thereof. In some embodiments, the taxane is coated with the carrier protein (such as albumin). In some embodiments, the second therapy is radiation therapy. In some embodiments, the second therapy is surgery.

In some embodiments, the method comprises a) a first therapy comprising administering to the individual a composition comprising nanoparticles comprising paclitaxel and an albumin; and b) a second therapy comprising radiation therapy, surgery, or combinations thereof. In some embodiments, the second therapy is radiation therapy. In some embodiments, the second therapy is surgery. In some embodiments, the paclitaxel/albumin nanoparticles have an average diameter of no greater than about 200 nm. In some embodiments, the paclitaxel/albumin nanoparticle composition is substantially free (such as free) of surfactant (such as Cremophor). In some embodiments, the weight ratio of the albumin to paclitaxel in the composition is about 18:1 or less, such as about 9:1 or less. In some embodiments, the paclitaxel is coated with albumin. In some embodiments, the paclitaxel/albumin nanoparticles have an average diameter of no greater than about 200 nm and the paclitaxel/albumin composition is substantially free (such as free) of surfactant (such as Cremophor). In some embodiments, the paclitaxel/albumin nanoparticles have an average diameter of no greater than about 200 nm and the paclitaxel is coated with albumin. In some embodiments, the nanoparticle composition is Abraxane™.

The administration of the nanoparticle composition may be prior to the radiation and/or surgery, after the radiation and/or surgery, or concurrent with the radiation and/or surgery. For example, the administration of the nanoparticle composition may precede or follow the radiation and/or surgery therapy by intervals ranging from minutes to weeks. In some embodiments, the time period between the first and the second therapy is such that the taxane and the radiation/surgery would still be able to exert an advantageously combined effect on the cell. For example, the taxane (such as paclitaxel) in the nanoparticle composition may be administered less than about any of 1, 3, 6, 9, 12, 18, 24, 48, 60, 72, 84, 96, 108, 120 hours prior to the radiation and/or surgery. In some embodiments, the nanoparticle composition is administered less than about 9 hours prior to the radiation and/surgery. In some embodiments, the nanoparticle composition is administered less than about any of 1, 2, 3, 4, 5, 6, 7, 8, 9, or 10 days prior to the radiation/surgery. In some embodiments, the taxane (such as paclitaxel) in the nanoparticle composition is administered less than about any of 1, 3, 6, 9, 12, 18, 24, 48, 60, 72, 84, 96, 108, or 120 hours after the radiation and/or surgery. In some embodiments, it may be desirable to extend the time period for treatment significantly, where several days to several weeks lapse between the two therapies.

Radiation contemplated herein includes, for example, γ-rays, X-rays (external beam), and the directed delivery of radioisotopes to tumor cells. Other forms of DNA damaging factors are also contemplated such as microwaves and UV irradiation are also contemplated. Radiation may be given in a single dose or in a series of small doses in a dose-fractionated schedule. The amount of radiation contemplated herein ranges from about 1 to about 100 Gy, including, for example, about 5 to about 80, about 10 to about 50 Gy, or about 10 Gy. The total dose may be applied in a fractioned regime. For example, the regime may comprise fractionated individual doses of 2 Gy. Dosage ranges for radioisotopes vary widely, and depends on the half-life of the isotope and the strength and type of radiation emitted.

When the radiation comprises use of radioactive isotopes, the isotope may be conjugated to a targeting agent, such as a therapeutic antibody, which carries the radionucleotide to the target tissue. Suitable radioactive isotopes include, but are not limited to, astatine$^{211}$, $^{14}$carbon, $^{51}$chromium, $^{36}$chlorine, $^{57}$iron, $^{58}$cobalt, copper$^{67}$, $^{152}$Eu, gallium$^{67}$, $^{3}$hydrogen, iodine$^{123}$, iodine$^{131}$, indium$^{111}$, $^{59}$ion, $^{32}$phosphorus, rhenium$^{186}$, $^{75}$selenium, $^{35}$sulphur, technicium$^{99m}$, and/or yttrium$^{90}$.

In some embodiments, enough radiation is applied to the individual so as to allow reduction of the normal dose of the taxane (such as paclitaxel) in the nanoparticle composition required to effect the same degree of treatment by at least about any of 5%, 10%, 20%, 30%, 50%, 60%, 70%, 80%, 90%, or more. In some embodiments, enough taxane in the nanoparticle composition is administered so as to allow reduction of the normal dose of the radiation required to effect the same degree of treatment by at least about any of 5%, 10%, 20%, 30%, 50%, 60%, 70%, 80%, 90%, or more. In some embodiments, the dose of both the taxane (such as paclitaxel) in the nanoparticle composition and the radiation are reduced as compared to the corresponding normal dose of each when used alone.

In some embodiments, the combination of administration of the nanoparticle composition and the radiation therapy produce supra-additive effect. In some embodiments, the taxane (such as paclitaxel) in the nanoparticle composition is administered once at the dose of 90 mg/kg, and the radiation is applied five times at 80 Gy daily.

Surgery described herein includes resection in which all or part of cancerous tissue is physically removed, exercised, and/or destroyed. Tumor resection refers to physical removal of at least part of a tumor. In addition to tumor resection, treatment by surgery includes laser surgery, cryosurgery, electrosurgery, and micropically controlled surgery (Mohs surgery). Removal of superficial surgery, precancers, or normal tissues are also contemplated.

The radiation therapy and/or surgery may be carried out in addition to the administration of chemotherapeutic agents. For example, the individual may first be administered with a taxane-containing nanoparticle composition and at least one other chemotherapeutic agent, and subsequently be subject to radiation therapy and/or surgery. Alternatively, the individual may first be treated with radiation therapy and/or surgery, which is then followed by the administration of a nanoparticle composition and at least one other chemotherapeutic agent. Other combinations are also contemplated.

Administration of nanoparticle compositions disclosed above in conjunction with administration of chemotherapeutic agent is equally applicable to those in conjunction with radiation therapy and/or surgery.

In some embodiments, the nanoparticle composition of the taxane and/or the chemotherapeutic agent is administered in conjunction with radiation according to any of the dosing regimes described in Table 2.

In some embodiments, there is provided a method of treating NSCLC in an individual comprises a) a first therapy comprising administering to the individual a composition comprising nanoparticles comprising taxane (such as paclitaxel) and an albumin; and b) a second therapy comprising radiation as provided in Rows 1 to 5 in Table 2. In some embodiments, the administration of the nanoparticle composition and the chemotherapeutic agent may be any of the dosing regimes as indicated in Rows 1 to 5 in Table 2.

In some embodiments, there is provided a method of treating headland neck cancer in an individual comprises a) a first therapy comprising administering to the individual a composition comprising nanoparticles comprising taxane (such as paclitaxel) and an albumin; and b) a second therapy comprising radiation as provided in Rows 6 to 9 in Table 2. In some embodiments, the administration of the nanoparticle composition and the chemotherapeutic agent may be any of the dosing regimes as indicated in Rows 6 to 9 in Table 2.

In some embodiments, there is provided a method of treating pancreatic cancer in an individual comprises a) a first therapy comprising administering to the individual a composition comprising nanoparticles comprising taxane (such as paclitaxel) and an albumin; and b) a second therapy comprising radiation as provided in Row 10 in Table 2. In some embodiments, the administration of the nanoparticle composition and the chemotherapeutic agent may be the dosing regimes as indicated in Row 10 in Table 2.

In some embodiments, there is provided a method of treating gastric malignancies in an individual comprises a) a first therapy comprising administering to the individual a composition comprising nanoparticles comprising taxane (such as paclitaxel) and an albumin; and b) a second therapy comprising radiation as provided in Row 11 in Table 2. In some embodiments, the administration of the nanoparticle composition and the chemotherapeutic agent may be the dosing regimes as indicated in Row 11 in Table 2.

TABLE 2

| Row No. | Combination | Regime/Dosage | Study therapy type | Protocol title |
|---|---|---|---|---|
| 1 | ABX + Radiation | | NSCLC | Phase I/II trial of Abraxane ™ combined with radiation |
| 2 | ABX + Carboplatin + Radiation | | NSCLC | Phase I/II trial of Abraxane ™ and carboplatin combined with radiation. |
| 3 | ABX + Carboplatin + Radiation | 1 cycle ABX/Carbo induction followed by 2 or 3 times weekly pulse ABX + radiation | NSCLC | Phase II chemoradiation in NSCLC |
| 4 | ABX + Carboplatin + Radiation | | NSCLC | Abraxane ™/carboplatin induction followed by Abraxane ™ + radiation in stage III A&B PS2 NSCLC patients |
| 5 | ABX + Carboplatin + Radiation | ABX qwk + carbo + radiation followed by ABX q3wk + carbo | NSCLC | Phase II study |
| 6 | ABX + Radiation | | Head and Neck Cancer | Abraxane ™ as a radiosensitizer in head and neck cancer |
| 7 | ABX + Cetuximab + Radiation | | Head and Neck Cancer | PhaseI/II Abraxane ™ in combination with cetuximab and radiation |
| 8 | ABX + Carboplatin + 5-FU + Hydroxyurea + Radiation | Induction: ABX 135 mg/m$^2$ qwk + carbo: AUC = 2 followed by Concurrent chemoradiation: ABX: 100 mg/m$^2$ 5-FU: 600 mg/m$^2$ hydroxyurea: 5000 mg BID | Head and Neck Cancer | Phase I/II study of induction chemotherapy with Abraxane ™ and carboplatin followed by concomitant fluorouracil, hydroxyurea, Abraxane ™ and IMRT for locally advanced head and neck cancers |
| 9 | ABX + Carboplatin + Erbitux ® + Radiation | ABX: 20-50 mg/m$^2$ qwk × 7 dose escalation Eribitux ®: 400 mg/m$^2$ day 7, 250 mg/m$^2$ qwk × 7 Carbo: AUC = 1.5 qwk × 7 IMRT | Locally Advanced Head and Neck Cancer | Phase I trial of Abraxane ™ in combination with carboplatin, cetuximab and IMRT in locally advanced squamous cell cancer of the head and neck |
| 10 | ABX + Gemcitabine + Radiation | qwk | Pancreatic Cancer | A randomized phase II trial of weekly gemcitabine, Abraxane ™, and external irradiation for locally advanced pancreatic cancer |
| 11 | ABX + Cisplatin + Radiation | | Gastric Malignancies | Phase I/II combination of Abraxane ™/cisplatin and radiation for patients with resected gastric/GEJ malignancies. |

In some embodiments, the invention provides pharmaceutical compositions comprising nanoparticles comprising a taxane (such as paclitaxel) and a carrier protein (such as albumin) for use in the treatment of a proliferative disease (such as cancer), wherein said use comprises a second therapy comprising radiation therapy, surgery, or combinations thereof.

Metronomic Therapy

The invention also provides metronomic therapy regime. There is provided a method of administering to an individual a composition comprising nanoparticles comprising a taxane (such as paclitaxel, docetaxel, or ortataxel) and a carrier protein (such as albumin) based on a metronomic dosing regime. The methods are applicable to methods of treatment, delaying development, and other clinical settings and configurations described herein. For example, in some embodiments, the methods are useful for treatment of proliferative diseases (such as cancer).

"Metronomic dosing regime" used herein refers to frequent administration of a taxane at without prolonged breaks at a dose below the established maximum tolerated dose via a traditional schedule with breaks (hereinafter also referred to as a "standard MTD schedule" or a "standard MTD regime"). In metronomic dosing, the same, lower, or higher cumulative dose over a certain time period as would be administered via a standard MTD schedule may ultimately be administered. In some cases, this is achieved by extending the time frame and/or frequency during which the dosing regime is conducted while decreasing the amount administered at each dose. Generally, the taxane administered via the metronomic dosing regime of the present invention is better tolerated by the individual. Metronomic dosing can also be referred to as maintenance dosing or chronic dosing.

In some embodiments, there is provided a method of administering a composition comprising nanoparticles comprising a taxane and a carrier protein (such as albumin), wherein the nanoparticle composition is administered over a period of at least one month, wherein the interval between each administration is no more than about a week, and wherein the dose of the taxane at each administration is about 0.25% to about 25% of its maximum tolerated dose following a traditional dosing regime. In some embodiments, there is provided a method of administering a composition comprising nanoparticles comprising paclitaxel and an albumin, wherein the nanoparticle composition is administered over a period of at least one month, wherein the interval between each administration is no more than about a week, and wherein the dose of the taxane at each administration is about 0.25% to about 25% of its maximum tolerated dose following a traditional dosing regime.

In some embodiments, the dosing of the taxane (such as paclitaxel) in the nanoparticle composition per administration is less than about any of 1%, 2%, 3&, 4%, 5%, 6%, 7%, 8%, 9%, 10%, 11%, 12%, 13%, 14%, 15%, 18%, 20%, 22%, 24%, or 25% of the MTD for the same taxane (such as paclitaxel) in the same formulation following a given traditional dosing schedule. Traditional dosing schedule refers to the dosing schedule that is generally established in a clinical setting. For example, the tradition dosing schedule for Abraxane™ is a three-weekly schedule, i.e., administering the composition every three weeks.

In some embodiments, the dosing of the taxane (such as paclitaxel) per administration is between about 0.25% to about 25% of the corresponding MTD value, including for example any of about 0.25% to about 20%, about 0.25% to about 15%, about 0.25% to about 10%, about 0.25% to about 20%, and about 0.25% to about 25%, of the corresponding MTD value. The MTD value for a taxane following a traditional dosing schedule is known or can be easily determined by a person skilled in the art. For example, the MTD value when Abraxane™ is administered following a traditional three-week dosing schedule is about 300 mg/m$^2$.

In some embodiments, there is provided a method of administering a composition comprising nanoparticles comprising a taxane and a carrier protein (such as albumin), wherein the nanoparticle composition is administered over a period of at least one month, wherein the interval between each administration is no more than about a week, and wherein the dose of the taxane at each administration is about 0.25 mg/m$^2$ to about 25 mg/m$^2$. In some embodiments, there is provided a method of administering a composition comprising nanoparticles comprising paclitaxel and an albumin, wherein the nanoparticle composition is administered over a period of at least one month, wherein the interval between each administration is no more than about a week, and wherein the dose of the taxane at each administration is about 0.25 mg/m$^2$ to about 25 mg/m$^2$.

In some embodiments, the dose of the taxane (such as paclitaxel) at each administration is less than about any of 2, 3, 4, 5, 6, 7, 8, 9, 10, 11, 12, 13, 14, 15, 18, 20, 22, 25, and 30 mg/m$^2$. For example, the dose of the taxane (such as paclitaxel) can range from about 0.25 mg/m$^2$ to about 30 mg/m$^2$, about 0.25 mg/m$^2$ to about 25 mg/m$^2$, about 0.25 mg/m$^2$ to about 15 mg/m$^2$, about 0.25 mg/m$^2$ to about 10 mg/m$^2$, and about 0.25 mg/m$^2$ to about 5 mg/m$^2$.

Dosing frequency for the taxane (such as paclitaxel) in the nanoparticle composition includes, but is not limited to, at least about any of once a week, twice a week, three times a week, four times a week, five times a week, six times a week, or daily. Typically, the interval between each administration is less than about a week, such as less than about any of 6, 5, 4, 3, 2, or 1 day. In some embodiments, the interval between each administration is constant. For example, the administration can be carried out daily, every two days, every three days, every four days, every five days, or weekly. In some embodiments, the administration can be carried out twice daily, three times daily, or more frequent.

The metronomic dosing regimes described herein can be extended over an extended period of time, such as from about a month up to about three years. For example, the dosing regime can be extended over a period of any of about 2, 3, 4, 5, 6, 7, 8, 9, 10, 11, 12, 18, 24, 30, and 36 months. Generally, there are no breaks in the dosing schedule.

The cumulative dose of the taxane (such as paclitaxel) administered by the metronomic regime may be higher than that of the taxane administered according to a standard MTD dosing schedule over the same time period. In some embodiments, the cumulative dose of the taxane administered by the metronomic regime equals to or is lower than that of the taxane administered according to a standard MTD dosing schedule over the same time period.

It is understood that the teaching provided herein is for examples only, and that metronomic dosing regime can be routinely designed in accordance with the teachings provided herein and based upon the individual standard MTD schedule, and that the metronomic dosing regime used in these experiments merely serves as one example of possible changes in dosing interval and duration which are made to a standard MTD schedule to arrive at an optimal metronomic dosing regime.

The metronomic dosing regime described herein may be used alone as a treatment of a proliferative disease, or carried out in a combination therapy context, such as the combination therapies described herein. In some embodiments, the metronomic therapy dosing regime may be used in combination or conjunction with other established therapies administered via standard MTD regimes. By "combination or in conjunction with" it is meant that the metronomic dosing regime of the present invention is conducted either at the same time as the standard MTD regime of established therapies, or between courses of induction therapy to sustain the benefit accrued to the individual by the induction therapy, the intent is to continue to inhibit tumor growth while not unduly compromising the individual's health or the individual's ability to withstand the next course of induction therapy. For example, a metronomic dosing regime may be adopted after an initial short course of MTD chemotherapy.

The nanoparticle compositions administered based on the metronomic dosing regime described herein can be administered to an individual (such as human) via various routes, such as parenterally, including intravenous, intra-arterial, intrapulmonary, oral, inhalation, intravesicular, intramuscular, intratracheal, subcutaneous, intraocular, intrathecal, or transdermal. For example, the nanoparticle composition can be administered by inhalation to treat conditions of the respiratory tract. The composition can be used to treat respiratory conditions such as pulmonary fibrosis, broncheolitis obliterans, lung cancer, bronchoalveolar carcinoma, and the like. In some embodiments, the nanoparticle composition is administered orally.

Some various exemplary embodiments are provided below.

In some embodiments, there is provided a method of administering a composition comprising nanoparticles comprising a taxane and a carrier protein (such as albumin), wherein the nanoparticle composition is administered over a period of at least one month, wherein the interval between each administration is no more than about a week, and wherein the dose of the taxane at each administration is about 0.25% to about 25% of its maximum tolerated dose following a traditional dosing regime. In some embodiments, the taxane is coated with the carrier protein (such as albumin). In some embodiments, the dose of the taxane per administration is less than about any of 1%, 2%, 3%, 4%, 5%, 6%, 7%, 8%, 9%, 10%, 11%, 12%, 13%, 14%, 15%, 18%, 20%, 22%, 24%, or 25% of the maximum tolerated dose. In some embodiments, the taxane is administered at least about any of 1×, 2×, 3×, 4×, 5×, 6×, 7× (i.e., daily) a week. In some embodiments, the intervals between each administration are less than about any of 7 days, 6 days, 5 days, 4 days, 3 days, 2 days, and 1 day. In some embodiments, the taxane is administered over a period of at least about any of 2, 3, 4, 5, 6, 7, 8, 9, 10, 11, 12, 18, 24, 30 and 36 months.

In some embodiments, there is provided a method of administering a composition comprising nanoparticles comprising paclitaxel and an albumin, wherein the nanoparticle composition is administered over a period of at least one month, wherein the interval between each administration is no more than about a week, and wherein the dose of the taxane at each administration is about 0.25% to about 25% of its maximum tolerated dose following a traditional dosing regime. In some embodiments, the paclitaxel/albumin nanoparticles have an average diameter of no greater than about 200 nm. In some embodiments, the paclitaxel/albumin nanoparticle composition is substantially free (such as free) of surfactant (such as Cremophor). In some embodiments, the weight ratio of the albumin to paclitaxel in the composition is about 18:1 or less, such as about 9:1 or less. In some embodiments, the paclitaxel is coated with albumin. In some embodiments, the paclitaxel/albumin nanoparticles have an average diameter of no greater than about 200 nm and the paclitaxel/ albumin composition is substantially free (such as free) of surfactant (such as Cremophor). In some embodiments, the paclitaxel/albumin nanoparticles have an average diameter of no greater than about 200 nm and the paclitaxel is coated with albumin. In some embodiments, the nanoparticle composition is Abraxane™.

In some embodiments, there is provided a method of administering a composition comprising nanoparticles comprising a taxane and a carrier protein (such as albumin), wherein the nanoparticle composition is administered over a period of at least one month, wherein the interval between each administration is no more than about a week, and wherein the dose of the taxane at each administration is about 0.25 mg/m$^2$ to about 25 mg/m$^2$. In some embodiments, the taxane is coated with the carrier protein (such as albumin). In some embodiments, the dose of the taxane per administration is less than about any of 2, 3, 4, 5, 6, 7, 8, 9, 10, 11, 12, 13, 14, 15, 18, 20, 22, and 25 mg/m$^2$. In some embodiments, the taxane is administered at least about any of 1×, 2×, 3×, 4×, 5×, 6×, 7× (i.e., daily) a week. In some embodiments, the intervals between each administration are less than about any of 7 days, 6 days, 5 days, 4 days, 3 days, 2 days, and 1 day. In some embodiments, the taxane is administered over a period of at least about any of 2, 3, 4, 5, 6, 7, 8, 9, 10, 11, 12, 18, 24, 30 and 36 months.

In some embodiments, there is provided a method of administering a composition comprising nanoparticles comprising paclitaxel and an albumin, wherein the nanoparticle composition is administered over a period of at least one month, wherein the interval between each administration is no more than about a week, and wherein the dose of the taxane at each administration is about 0.25 mg/m$^2$ to about 25 mg/m$^2$. In some embodiments, the paclitaxel/albumin nanoparticles have an average diameter of no greater than about 200 nm. In some embodiments, the paclitaxel/albumin nanoparticle composition is substantially free (such as free) of surfactant (such as Cremophor). In some embodiments, the weight ratio of the albumin to paclitaxel in the composition is about 18:1 or less, such as about 9:1 or less. In some embodiments, the paclitaxel is coated with albumin. In some embodiments, the paclitaxel/albumin nanoparticles have an average diameter of no greater than about 200 nm and the paclitaxel/ albumin composition is substantially free (such as free) of surfactant (such as Cremophor). In some embodiments, the paclitaxel/albumin nanoparticles have an average diameter of no greater than about 200 nm and the paclitaxel is coated with albumin. In some embodiments, the nanoparticle composition is Abraxane™.

In some embodiments, the Abraxane™ (or other paclitaxel/albumin nanoparticle compositions) is administered at the dose of about 3 mg/kg to about 10 mg/kg daily. In some embodiments, the Abraxane™ is administered at the dose of about 6 mg/kg to about 10 mg/kg daily. In some embodiments, the Abraxane™ is administered at the dose of about 6 mg/kg daily. In some embodiments, Abraxane™ is administered at the dose of about 3 mg/kg daily.

The invention also provides compositions for use in the metronomic regime(s) described herein. In some embodiments, there is provided a composition comprising nanoparticles comprising a taxane and a carrier protein (such as albumin), wherein said composition is administered to an individual via a metronomic dosing regime, such as the dosing regime described herein.

Other Aspects of the Invention

In another aspects, there are provided methods of treating proliferative diseases comprising administering a composition comprising nanoparticles comprising a taxane (including pacltiaxel, docetaxel, or ortataxel) and a carrier protein (such as albumin). In some embodiments, there is provided a method of treating cancer comprising administering a composition comprising nanoparticles comprising ortataxel and a carrier protein (such as albumin).

In some embodiments, there is provided methods of treating proliferative diseases comprising administering a composition comprising nanoparticles comprising a thiocolchicine or its derivative (such as dimeric thiocolchicine) and a carrier protein (such as albumin). In some embodiments, there is provided a method of treating cancer comprising administering a composition comprising nanoparticles comprising dimeric colchicines and a carrier protein (such as albumin). In some embodiments, the nanoparticle composition is any of (and in some embodiments selected from the group consisting of) Nab-5404, Nab-5800, and Nab-5801.

In some embodiments, there is provided a method of treating cancer comprising administering a composition comprising nanoparticles comprising paclitaxel, wherein the nanoparticle composition is administered according to any of the dosing regimes described in Table 3. In some embodiments, the cancer is a Taxane refractory metastatic breast cancer.

TABLE 3

| Row No. | Combination | Regimen/Dosage | Study therapy type | Protocol title |
|---|---|---|---|---|
| 1 | ABX alone | ABX: 125 mg/m$^2$ qwk × 3/4 | Metastatic Breast Cancer | Phase II study with weekly Abraxane ™ treatment in taxane-refractory MBC patients |
| 2. | ABX alone | Arm 1: ABX 130 mg/m$^2$ qwk<br>Arm 2: ABX 260 mg/m$^2$ q2wk<br>Arm 3: ABX 260 mg/m$^2$ q3wk | Metastatic Breast Cancer | 3-arm phase II trial in 1st-line Her-2-MBC patients. |
| 3. | ABX alone (Capxol) | ABX: 260 mg/m$^2$ q3wk<br>vs<br>Taxol: 175 mg/m$^2$ q3wk | Metastatic Breast Cancer | Phase II Controlled, Randomized, Open Label Study to Evaluate the Efficacy and Safety of Capxol (a Cremophor-Free Nanoparticle Paclitaxel) and cremophor-formulated paclitaxel injection in Patient with Metastatic Breast Cancer |
| 4. | ABX alone | Arm 1: ABX weekly<br>Arm 2: ABX q3wk<br>Arm 3: Taxol weekly | Metastatic Breast Cancer | 3-arm phase II trial in 1st-line and 2nd-line MBC, with biological correlates analysis |
| 5. | ABX alone | ABX: 300 mg/m$^2$ q3wk | Stage IIA, IIB, IIIA, IIIB and IV breast cancer | Phase II trial of neoadjuvant chemotherapy (NCT) with nanoparticle paclitaxel (ABI-007, Abraxane) in women with clinical stage IIA, IIB, IIIA, IIIB and IV (with intact primary) breast cancers |
| 6. | ABX alone | ABX: 125 mg/m$^2$ qwk × 3/4 | 1st-line advanced NSCLC | Phase I/II study of Abraxane monotherapy in 1st-line advanced NSCLC |
| 7. | ABX alone | ABX 260 mg/m$^2$ q3wk | 1st-line NSCLC | Phase II ABX mono in 1st-line NSCLC |
| 8. | ABX alone | Arm 1: ABX q3wk<br>Arm 2: ABX qwk<br>Doses TBD | 2$^{nd}$ line NSCLC | Phase II study of Abraxane monotherapy in 2$^{nd}$-line NSCLC |
| 9. | ABX alone | ABX: 100 mg/m$^2$ qwk<br>vs<br>ABX: 260 mg/m$^2$ q3wk | Prostate Cancer | Randomized phase II study Abraxane ™ weekly vs every three weeks in front line HRP |
| 10. | ABX alone | ABX qwk | Prostate Cancer | Phase II ABX in 1st-line prostate cancer |
| 11. | ABX alone | ABX: 150 mg/m$^2$ qwk × 3/4 for 2 cycles | Prostate Cancer | Phase II neoadjuvant study |
| 12. | ABX alone | ABX: 100 mg/m$^2$ qwk (no break) | Prostate Cancer | Phase II ABX 100 mg weekly no break |
| 13. | ABX alone | ABX: 100 mg/m$^2$ (previously treated)<br>ABX: 150 mg/m$^2$ (untreated) qwk × 3/4 | Malignant Melanoma | Phase II previously treated and untreated metastatic melanoma patients |
| 14. | ABX alone | ABX: 125 mg/m$^2$ qwk × 3/4 | Carcinoma of the cervix | Phase II study of ABX in treatment of persistent or recurrent carcinoma of the cervix |
| 15. | ABX alone | | Ovarian Cancer | Phase II study of Abraxane for treatment of advanced ovarian cancer (3$^{rd}$ line) |

TABLE 3-continued

| Row No. | Combination | Regimen/Dosage | Study therapy type | Protocol title |
|---|---|---|---|---|
| 16. | ABX alone (ABI-007) | | non-hematologic malignancies | Phase II single treatment use of ABI-007 for the treatment of non-hematologic malignancies. Compassionate use |

Nanoparticle Compositions

The nanoparticle compositions described herein comprise nanoparticles comprising (in various embodiments consisting essentially of) a taxane (such as paclitaxel) and a carrier protein (such as albumin). Nanoparticles of poorly water soluble drugs (such as taxane) have been disclosed in, for example, U.S. Pat. Nos. 5,916,596; 6,506,405; and 6,537,579 and also in U.S. Pat. Pub. No. 2005/0004002A1. Although the description provided below is specific to taxane, it is understood that the same applies to other drugs, such as rapamycin, 17-AAG, and dimeric thiocolchicine.

In some embodiments, the composition comprises nanoparticles with an average or mean diameter of no greater than about 1000 nanometers (nm), such as no greater than about any of 900, 800, 700, 600, 500, 400, 300, 200, and 100 nm. In some embodiments, the average or mean diameters of the nanoparticles is no greater than about 200 nm. In some embodiments, the average or mean diameters of the nanoparticles is no greater than about 150 nm. In some embodiments, the average or mean diameters of the nanoparticles is no greater than about 100 nm. In some embodiments, the average or mean diameter of the nanoparticles is about 20 to about 400 nm. In some embodiments, the average or mean diameter of the nanoparticles is about 40 to about 200 mm. In some embodiments, the nanoparticles are sterile-filterable.

The nanoparticles described herein may be present in a dry formulation (such as lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

The term "proteins" refers to polypeptides or polymers of amino acids of any length (including full length or fragments), which may be linear or branched, comprise modified amino acids, and/or be interrupted by non-amino acids. The term also encompasses an amino acid polymer that has been modified naturally or by intervention; for example, disulfide bond formation, glycosylation, lipidation, acetylation, phosphorylation, or any other manipulation or modification. Also included within this term are, for example, polypeptides containing one or more analogs of an amino acid (including, for example, unnatural amino acids, etc.), as well as other modifications known in the art. The proteins described herein may be naturally occurring, i.e., obtained or derived from a natural source (such as blood), or synthesized (such as chemically synthesized or by synthesized by recombinant DNA techniques).

Examples of suitable carrier proteins include proteins normally found in blood or plasma, which include, but are not limited to, albumin, immunoglobulin including IgA, lipoproteins, apolipoprotein B, alpha-acid glycoprotein, beta-2-macroglobulin, thyroglobulin, transferin, fibronectin, factor VII, factor VIII, factor IX, factor X, and the like. In some embodiments, the carrier protein is non-blood protein, such as casein, α-lactalbumin, and β-lactoglobulin. The carrier proteins may either be natural in origin or synthetically prepared. In some embodiments, the pharmaceutically acceptable carrier comprises albumin, such as human serum albumin. Human serum albumin (HSA) is a highly soluble globular protein of $M_r$ 65K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Intravenous use of HSA solution has been indicated for the prevention and treatment of hypovolumic shock (see, e.g., Tullis, *JAMA*, 237, 355-360, 460-463, (1977)) and Houser et al., *Surgery, Gynecology and Obstetrics*, 150, 811-816 (1980)) and in conjunction with exchange transfusion in the treatment of neonatal hyperbilirubinemia (see, e.g., Finlayson, *Seminars in Thrombosis and Hemostasis*, 6, 85-120, (1980)). Other albumins are contemplated, such as bovine serum albumin. Use of such non-human albumins could be appropriate, for example, in the context of use of these compositions in non-human mammals, such as the veterinary (including domestic pets and agricultural context).

Human serum albumin (HSA) has multiple hydrophobic binding sites (a total of eight for fatty acids, an endogenous ligand of HSA) and binds a diverse set of taxanes, especially neutral and negatively charged hydrophobic compounds (Goodman et al., *The Pharmacological Basis of Therapeutics*, $9^{th}$ ed, McGraw-Hill New York (1996)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., *Biochem. Pharmcol.*, 30, 687-92 (198a), Vorum, *Dan. Med. Bull*, 46, 379-99 (1999), Kragh-Hansen, *Dan. Med. Bull.*, 1441, 131-40 (1990), Curry et al., *Nat. Struct. Biol.*, 5, 827-35 (1998), Sugio et al., *Protein. Eng.*, 12, 439-46 (1999), He et al., *Nature*, 358, 209-15 (199b), and Carter et al., *Adv. Protein. Chem.*, 45, 153-203 (1994)). Paclitaxel and propofol have been shown to bind HSA (see, e.g., Paal et al., *Eur. J. Biochem.*, 268(7), 2187-91 (200a), Purcell et al., *Biochim. Biophys. Acta*, 1478(a), 61-8 (2000), Altmayer et al., *Arzneimittelforschung*, 45, 1053-6 (1995), and Garrido et al., *Rev. Esp. Anestestiol. Reanim.*, 41, 308-12 (1994)). In addition, docetaxel has been shown to bind to human plasma proteins (see, e.g., Urien et al., *Invest. New Drugs*, 14(b), 147-51 (1996)).

The carrier protein (such as albumin) in the composition generally serves as a carrier for the taxane, i.e., the carrier protein in the composition makes the taxane more readily suspendable in an aqueous medium or helps maintain the suspension as compared to compositions not comprising a carrier protein. This can avoid the use of toxic solvents (or surfactants) for solubilizing the taxane, and thereby can reduce one or more side effects of administration of the taxane into an individual (such as a human). Thus, in some embodiments, the composition described herein is substantially free (such as free) of surfactants, such as Cremophor (including Cremophor EL® (BASF)). In some embodiments, the nanoparticle composition is substantially free (such as free) of surfactants. A composition is "substantially free of Cremophor" or "substantially free of surfactant" if the amount of Cremophor or surfactant in the composition is not sufficient to cause one or more side effect(s) in an individual when the nanoparticle composition is administered to the individual.

The amount of carrier protein in the composition described herein will vary depending on other components in the composition. In some embodiments, the composition comprises a carrier protein in an amount that is sufficient to stabilize the taxane in an aqueous suspension, for example, in the form of a stable colloidal suspension (such as a stable suspension of nanoparticles). In some embodiments, the carrier protein is in an amount that reduces the sedimentation rate of the taxane in an aqueous medium. For particle-containing compositions, the amount of the carrier protein also depends on the size and density of nanoparticles of the taxane.

A taxane is "stabilized" in an aqueous suspension if it remains suspended in an aqueous medium (such as without visible precipitation or sedimentation) for an extended period of time, such as for at least about any of 0.1, 0.2, 0.25, 0.5, 1, 2, 3, 4, 5, 6, 7, 8, 9, 10, 11, 12, 24, 36, 48, 60, or 72 hours. The suspension is generally, but not necessarily, suitable for administration to an individual (such as human). Stability of the suspension is generally (but not necessarily) evaluated at a storage temperature (such as room temperature (such as 20-25° C.) or refrigerated conditions (such as 4° C.)). For example, a suspension is stable at a storage temperature if it exhibits no flocculation or particle agglomeration visible to the naked eye or when viewed under the optical microscope at 1000 times, at about fifteen minutes after preparation of the suspension. Stability can also be evaluated under accelerated testing conditions, such as at a temperature that is higher than about 40° C.

In some embodiments, the carrier protein is present in an amount that is sufficient to stabilize the taxane in an aqueous suspension at a certain concentration. For example, the concentration of the taxane in the composition is about 0.1 to about 100 mg/ml, including for example any of about 0.1 to about 50 mg/ml, about 0.1 to about 20 mg/ml, about 1 to about 10 mg/ml, about 2 mg/ml to about 8 mg/ml, about 4 to about 6 mg/ml, about 5 mg/ml. In some embodiments, the concentration of the taxane is at least about any of 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, and 50 mg/ml. In some embodiments, the carrier protein is present in an amount that avoids use of surfactants (such as Cremophor), so that the composition is free or substantially free of surfactant (such as Cremophor).

In some embodiments, the composition, in liquid form, comprises from about 0.1% to about 50% (w/v) (e.g. about 0.5% (w/v), about 5% (w/v), about 10% (w/v), about 15% (w/v), about 20% (w/v), about 30% (w/v), about 40% (w/v), or about 50% (w/v)) of carrier protein. In some embodiments, the composition, in liquid form, comprises about 0.5% to about 5% (w/v) of carrier protein.

In some embodiments, the weight ratio of carrier protein, e.g., albumin, to the taxane in the nanoparticle composition is such that a sufficient amount of taxane binds to, or is transported by, the cell. While the weight ratio of carrier protein to taxane will have to be optimized for different carrier protein and taxane combinations, generally the weight ratio of carrier protein, e.g., albumin, to taxane (w/w) is about 0.01:1 to about 100:1, about 0.02:1 to about 50:1, about 0.05:1 to about 20:1, about 0.1:1 to about 20:1, about 1:1 to about 18:1, about 2:1 to about 15:1, about 3:1 to about 12:1, about 4:1 to about 10:1, about 5:1 to about 9:1, or about 9:1. In some embodiments, the carrier protein to taxane weight ratio is about any of 18:1 or less, 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less.

In some embodiments, the carrier protein allows the composition to be administered to an individual (such as human) without significant side effects. In some embodiments, the carrier protein (such as albumin) is in an amount that is effective to reduce one or more side effects of administration of the taxane to a human. The term "reducing one or more side effects of administration of the taxane" refers to reduction, alleviation, elimination, or avoidance of one or more undesirable effects caused by the taxane, as well as side effects caused by delivery vehicles (such as solvents that render the taxanes suitable for injection) used to deliver the taxane. Such side effects include, for example, myelosuppression, neurotoxicity, hypersensitivity, inflammation, venous irritation, phlebitis, pain, skin irritation, peripheral neuropathy, neutropenic fever, anaphylactic reaction, venous thrombosis, extravasation, and combinations thereof. These side effects, however, are merely exemplary and other side effects, or combination of side effects, associated with taxanes can be reduced.

In some embodiments, the composition comprises Abraxane™. Abraxane™ is a formulation of paclitaxel stabilized by human albumin USP, which can be dispersed in directly injectable physiological solution. When dispersed in a suitable aqueous medium such as 0.9% sodium chloride injection or 5% dextrose injection, Abraxane™ forms a stable colloidal suspension of paclitaxel. The mean particle size of the nanoparticles in the colloidal suspension is about 130 nanometers. Since HSA is freely soluble in water, Abraxane™ can be reconstituted in a wide range of concentrations ranging from dilute (0.1 mg/ml paclitaxel) to concentrated (20 mg/ml paclitaxel), including for example about 2 mg/ml to about 8 mg/ml, about 5 mg/ml.

Methods of making nanoparticle compositions are known in the art. For example, nanoparticles containing taxanes (such as paclitaxel) and carrier protein (such as albumin) can be prepared under conditions of high shear forces (e.g., sonication, high pressure homogenization, or the like). These methods are disclosed in, for example, U.S. Pat. Nos. 5,916, 596; 6,506,405; and 6,537,579 and also in U.S. Pat. Pub. No. 2005/0004002A1.

Briefly, the taxane (such as docetaxel) is dissolved in an organic solvent, and the solution can be added to a human serum albumin solution. The mixture is subjected to high pressure homogenization. The organic solvent can then be removed by evaporation. The dispersion obtained can be further lyophilized. Suitable organic solvent include, for example, ketones, esters, ethers, chlorinated solvents, and other solvents known in the art. For example, the organic solvent can be methylene chloride and chloroform/ethanol (for example with a ratio of 1:9, 1:8, 1:7, 1:6, 1:5, 1:4, 1:3, 1:2, 1:1, 2:1, 3:1, 4:1, 5:1, 6:1, 7:1, 8:1, or 9:a).

Other Components in the Nanoparticle Compositions

The nanoparticles described herein can be present in a composition that include other agents, excipients, or stabilizers. For example, to increase stability by increasing the negative zeta potential of nanoparticles, certain negatively charged components may be added. Such negatively charged components include, but are not limited to bile salts of bile acids consisting of glycocholic acid, cholic acid, chenodeoxycholic acid, taurocholic acid, glycochenodeoxycholic acid, taurochenodeoxycholic acid, litocholic acid, ursodeoxycholic acid, dehydrocholic acid and others; phospholipids including lecithin (egg yolk) based phospholipids which include the following phosphatidylcholines: palmitoyloleoylphosphatidylcholine, palmitoyllinoleoylphosphatidylcholine, stearoyllinoleoylphosphatidylcholine stearoyloleoylphosphatidylcholine, stearoylarachidoylphosphatidylcholine, and dipalmitoylphosphatidylcholine. Other phospholipids including L-α-dimyristoylphosphatidylcholine (DMPC), dioleoylphosphatidylcholine (DOPC), distearyolphosphatidylcholine (DSPC), hydrogenated soy phosphatidylcholine (HSPC), and other related compounds. Negatively charged surfactants or emulsifiers are also suitable as additives, e.g., sodium cholesteryl sulfate and the like.

In some embodiments, the composition is suitable for administration to a human. In some embodiments, the composition is suitable for administration to a mammal such as, in the veterinary context, domestic pets and agricultural animals. There are a wide variety of suitable formulations of the nanoparticle composition (see, e.g., U.S. Pat. Nos. 5,916,596 and 6,096,331). The following formulations and methods are merely exemplary and are in no way limiting. Formulations suitable for oral administration can consist of (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Examples of suitable carriers, excipients, and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate, and mineral oil. The formulations can additionally include lubricating agents, wetting agents, emulsifying and suspending agents, preserving agents, sweetening agents or flavoring agents.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Injectable formulations are preferred.

In some embodiments, the composition is formulated to have a pH range of about 4.5 to about 9.0, including for example pH ranges of any of about 5.0 to about 8.0, about 6.5 to about 7.5, and about 6.5 to about 7.0. In some embodiments, the pH of the composition is formulated to no less than about 6, including for example no less than about any of 6.5, 7, or 8 (such as about 8). The composition can also be made to be isotonic with blood by the addition of a suitable tonicity modifier, such as glycerol.

Kits

The invention also provides kits for use in the instant methods. Kits of the invention include one or more containers comprising taxane-containing nanoparticle compositions (or unit dosage forms and/or articles of manufacture) and/or a chemotherapeutic agent, and in some embodiments, further comprise instructions for use in accordance with any of the methods described herein. The kit may further comprise a description of selection an individual suitable or treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

In some embodiments, the kit comprises a) a composition comprising nanoparticles comprising a taxane and a carrier protein (such as albumin), b) an effective amount of at least one other chemotherapeutic agent, and c) instructions for administering the nanoparticles and the chemotherapeutic agents simultaneously and/or sequentially, for treatment of a proliferative disease (such as cancer). In some embodiments, the taxane is any of paclitaxel, docetaxel, and ortataxel. In some embodiments, the kit comprises nanoparticles comprising a) a composition comprising nanoparticles comprising paclitaxel and an albumin (such as Abraxane™), b) an effective amount of at least one other chemotherapeutic agent, and c) instructions for administering the nanoparticles and the chemotherapeutic agents simultaneously and/or sequentially, for the effective treatment of a proliferative disease (such as cancer).

In some embodiments, the kit comprises a) a composition comprising nanoparticles comprising a taxane and a carrier protein (such as albumin), b) a composition comprising nanoparticles comprising at least one other chemotherapeutic agent and a carrier protein (such as albumin), and c) instructions for administering the nanoparticle compositions simultaneously and/or sequentially, for treatment of a proliferative disease (such as cancer). In some embodiments, the kit comprises nanoparticles comprising a) a composition comprising nanoparticles comprising paclitaxel and an albumin (such as Abraxane™), b) a composition comprising nanoparticles comprising at least one other chemotherapeutic agent and a carrier protein (such as albumin), and c) instructions for administering the nanoparticle compositions simultaneously and/or sequentially, for the effective treatment of a proliferative disease (such as cancer).

The nanoparticles and the chemotherapeutic agents can be present in separate containers or in a single container. It is understood that the kit may comprise one distinct composition or two or more compositions wherein one composition comprises nanoparticles and one composition comprises a chemotherapeutic agent.

The kits of the invention are in suitable packaging. Suitable packaging include, but is not limited to, vials, bottles, jars, flexible packaging (e.g., seled Mylar or plastic bags), and the like. Kits may optionally provide additional components such as buffers and interpretative information.

The instructions relating to the use of the nanoparticle compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of the taxane (such as taxane) as disclosed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the taxane and pharmaceutical compositions and instructions for use and packaged in quantities sufficient for storage and use in pharmacies, for example, hospital pharmacies and compounding pharmacies.

Those skilled in the art will recognize that several variations are possible within the scope and spirit of this invention. The invention will now be described in greater detail by reference to the following non-limiting examples. The following examples further illustrate the invention but, of course, should not be construed as in any way limiting its scope.

EXAMPLES

Example 1

Improved Response and Reduced Toxicities for Abraxane™ Compared to Taxol® in a Phase III Study of Abraxane™ Given Every Three Weeks Significantly reduced incidence of neutropenia and hypersensitivity, absence of requirement of steroid premedication, shorter duration of neuropathy, shorter infusion time and higher dose.

ABI-007 (Abraxane™), the first biologically interactive albumin-bound paclitaxel in a nanoparticle form, free of any solvent, was compared with Cremophor®-based paclitaxel (Taxol®) in individuals with metastatic breast cancer (MBC). This phase III study was performed to confirm the preclinical studies demonstrating superior efficacy and reduced toxicity of ABI-007 when compared with Taxol®. Individuals were randomly assigned to 3-week cycles of either ABI-007 260 mg/m$^2$ (iv) over 30 minutes without premedication (n=229) or Taxol® 175 mg/m$^2$ IV over 3 hours with premedication (n=225). ABI-007 demonstrated significantly higher response rates compared with Taxol® (33% vs. 19%; p=0.001) and significantly longer time to tumor progression (23.0 vs. 16.9 weeks; HR=0.75; p=0.006). There was a trend for longer overall survival in individuals who received ABI-007 (65.0 vs. 55.7 weeks; p=0.374). In an unplanned analysis, ABI-007 improved survival in individuals receiving treatment as second- or greater-line therapy (56.4 vs. 46.7 weeks; HR=0.73; p=0.024). The incidence of grade 4 neutropenia was significantly lower in the ABI-007 group (9% vs. 22%; p<0.001) despite a 49% higher paclitaxel dose. Grade 3 sensory neuropathy was more common in the ABI-007 group than in the Taxol® group (10% vs. 2%; p<0.001) but was easily managed and improved more rapidly (median, 22 days) than for Taxol® (median 73 days). No severe (grade 3 or 4) treatment-related hypersensitivity reactions occurred in any of the individuals in the ABI-007 group despite the absence of premedication and shorter administration time. In contrast, grade 3 hypersensitivity reactions occurred in the Taxol® group despite standard premedication (chest pain: 2 individuals; allergic reaction: 3 individuals). Per protocol, corticosteroids and antihistamines were not administered routinely to individuals in the ABI-007 group; however, premedication was administered for emesis, myalgia/arthralgia, or anorexia in 18 individuals (8%) in the ABI-007 group in 2% of the treatment cycles, whereas 224 individuals (>99%) in the Taxol® group received premedication at 95% of the cycles. The only clinical chemistry value that was notably different between the 2 treatment arms was higher serum glucose levels in the Taxol®-treated individuals, who also had a higher incidence of hyperglycemia reported as an AE (adverse effects) (15 [7%] vs. 3 [1%]; p=0.003). Overall, ABI-007 demonstrated greater efficacy and a favorable safety profile compared with Taxol® in this individual population. The improved therapeutic index and elimination of the steroid premedication required for solvent-based taxanes make this nanoparticle albumin-bound paclitaxel an important advance in the treatment of MBC.

Example 2

Weekly Abraxane™ in Taxane-Refractory Metastatic Breast Cancer Individuals

A recent Phase II clinical study showed that weekly administration of Abraxane™ (nanoparticle albumin-bound paclitaxel) at a dose of 125 mg/m$^2$ resulted in long-term disease control in individuals with metastatic breast cancer whose disease had progressed while being treated with Taxol® or Taxotere® (that is, individuals who are taxane-refractory).

Abraxane™ is believed to represent the first biologically interactive composition that exploits the receptor-mediated (gp60) pathway found to be integral to achieving high intracellular tumor concentrations of the active ingredient—paclitaxel. The Phase II study included 75 individuals with taxane-refractory metastatic breast cancer. Abraxane™ was administered weekly via a 30-minute infusion at 125 mg/m$^2$ without steroid/antihistamine premedication or G-CSF prophylaxis. Individuals received three weekly doses followed by one week of rest, repeated every 28 days. Unlike Taxol® or Taxotere®, which contain detergents that may inhibit tumor uptake, the mechanism of action of the albumin-bound nanoparticle paclitaxel may result in improved outcomes, especially in this difficult-to-treat individual population.

Specifically, the data showed that despite this high weekly dose of 125 mg/m$^2$ in this highly pre-treated and prior taxane-exposed individual population, only 3 of 75 individuals (4%) had to discontinue Abraxane™ due to peripheral neuropathy. Furthermore, of those who experienced Grade 3 peripheral neuropathy, 80% were typically able to resume treatment after a delay of only 1 or 2 weeks and continued to receive Abraxane™ at a reduced dose for an average of 4 additional months. This rapid improvement was consistent with our observation from the Phase III trial—that the peripheral neuropathy induced by paclitaxel alone (i.e., without Cremophor®) improves rapidly as compared to that induced by Taxol®. These Abraxane™ clinical trial experiences provide the first clinical opportunity to evaluate the effects of the chemotherapeutic agent itself, paclitaxel, from the effects from those of solvents. Based upon both the Phase II and III experience, the data now suggest that the peripheral neuropathy from Abraxane™ is not comparable to the peripheral neuropathy from Taxol® or Taxotere® with respect to duration and impact on the individual.

With regard to the clinical experience of peripheral neuropathy following Taxol® or Taxotere®, Abraxis Oncology recently completed a survey of 200 oncologists who were asked how long they thought the peripheral neuropathy induced by Taxol® took to improve and/or resolve: 25% reported "7-12 months" and another 23% reported "never resolved"; for Taxotere®, the respective percentages were 29% and 7%. These data are consistent with the statements in the Taxotere® and Taxol® package inserts.

Analysis of the Phase II data demonstrates Abraxane™ to be active in this poor-prognosis individual population (87% visceral (lung and liver) disease, 69%>3 metastatic sites, 88% tumor growth while on taxanes), of taxane-refractory individuals with metastatic breast cancer. Observations included a 44% disease control in Taxotere®-refractory individuals and 39% disease control in Taxol®-refractory individuals. Of those individuals whose disease progressed while on Taxotere® alone in the metastatic setting (n=27) a 19% response rate was noted after receiving weekly Abraxane™. Of those individuals whose disease progressed while on Taxol® alone in the metastatic setting (n=23) a 13% response rate was noted after receiving weekly Abraxane™.

Abraxane™ was found to be well tolerated when administered weekly over 30 minutes without steroids or G-CSF prophylaxis: Grade 4 neutropenia=3% (without G-CSF); Grade 4 anemia=1%; no severe hypersensitivity reactions (despite absence of premedication). In this heavily pretreated individual population, 75% of individuals were treated at the full high dose of 125 mg/m$^2$ weekly Abraxane™, with no dose reductions due to toxicities/adverse events. Of the individuals who developed grade 3 sensory neuropathy, 77% were able to restart Abraxane™ at a reduced dose (75-100 mg/m$^2$) and received a mean of 12.2 (range, 1-28) additional doses of Abraxane™. It was remarkable to note that of these individuals who resumed Abraxane™, 80% (8 of 10) were able to restart the drug within 14 days after improvement of neuropathy to Grade 1 or 2. These results support the observations in the pivotal Phase III trial of 260 mg/m$^2$ Abraxane™ administered every 3 weeks, in which rapid improvement of neuropathy (median of 22 days) was also noted. Taken together these two clinical trials suggest when paclitaxel is given alone, the neuropathy which occurs appears to be short-lived and is easily managed.

Abraxane™ utilizes the gp60 receptor based pathway on the microvessel endothelial cells to transport the albumin-paclitaxel complex out of the blood vessel and into the tumor interstitium, and it has been shown that Taxol® was not transported by this mechanism. Furthermore, an albumin-binding protein, SPARC, was over-expressed in breast tumors and may play a role in the increased intra-tumoral accumulation of Abraxane™. The proposed mechanism suggested that once in the tumor interstitium, the albumin-paclitaxel complex would bind to SPARC that was present on the tumor cell surface and be rapidly internalized into the tumor cell by a non-lysosomal mechanism.

In addition, the surfactants/solvents commonly used in current taxane formulations such as Cremophor®, Tween® 80 and TPGS, strongly inhibit the binding of paclitaxel to albumin, thereby limiting transendothelial transport. Additional data presented showed a statistically improved efficacy of Abraxane™ over Taxotere® in the MX-1 mammary breast carcinoma xenograft at equal dose.

In conclusion, 75% of individuals were treated at full high dose with no dose reductions. Data indicate rapid improvement of peripheral neuropathy when nanoparticle albumin-bound paclitaxel is administered alone, without the solvent Cremophor®. Additional data provide increased evidence that mechanism of action may play important role in enhancing individual outcomes.

Example 3

Abraxane™ (ABI-007) Acts Synergistically with Targeted Antiangiogenic Pro-Apoptotic Peptides (HKP) in MDA-MB-435 Human Tumor Xenografts The antiangiogenic activity of small synthetic pro-apoptotic peptides composed of two functional domains, one targeting the CD13 receptors (aminopeptidase N) on tumor microvessels and the other disrupting the mitochondrial membrane following internalization have previously been reported. See Nat Med. 1999 September; 5(9):1032-8. A second generation dimeric peptide, CNGRC-GG-d(KLAK-LAK)$_2$, named HKP (Hunter Killer Peptide) was found to have improved antitumor activity. Since anti-angiogenic agents such as Avastin® exhibit synergism in combination with cytotoxic agents such as 5-fluorouracil, we evaluated the combination of the antiangiogenic HKP with Abraxane™ (ABI-007), an albumin nanoparticle paclitaxel that is transported by the gp60 receptor in vascular endothelium (Desai, SABCS 2003), in MDA-MB-435 human breast tumor xenografts.

Methods: MDA-MB-435 human tumor xenografts were established at an average tumor volume of 100 mm$^3$, mice were randomized into groups of 12-13 animals and treated with HKP, Abraxane™, or HKP and Abraxane™. HKP was delivered i.v. (250 ug), once a week, for 16 weeks. Abraxane™ was administered i.v., daily for 5 days at 10 mg/kg/day only for the first week of treatment. The Abraxane™ dose used was substantially below its MTD (30 mg/kg/day, qd×5) to prevent the tumor from complete regression so effect of HKP could be noted.

Results: At nineteen weeks of treatment, tumor volume was significantly decreased between control group (10,298 mm$^3$±2,570) and HKP (4,372 mm$^3$±2,470; p<0.05 vs control) or ABI-007 (3,909 mm$^3$±506; p<0.01 vs control). The combination of ABI-007 and HKP significantly reduced the tumor volume over either monotherapy (411 mm$^3$±386; p<0.01 vs. Abraxane™ monotherapy or HKP monotherapy). The treatments were well tolerated.

Conclusion: The combination of Abraxane™ (ABI-007), a nanoparticle albumin-bound paclitaxel, with the vascular targeting anti-angiogenic dimeric peptide HKP (CNGRC-GG-d(KLAKLAK)$_2$) against the MDA-MB-435 xenograft breast tumor showed a significant reduction in tumor volume compared to monotherapy of either agent alone. Our results suggest that the combination of Abraxane™ with antiangiogenic agents such as HKPs or perhaps Avastin® may be beneficial.

Example 4

Metronomic ABI-007 Therapy: Antiangiogenic and Antitumor Activity of a Nanoparticle Albumin-Bound Paclitaxel Example 4a Methods: The antiangiogenic activity of ABI-007 was assessed by the rat aortic ring, human umbilical vein endothelial cell (HUVEC) proliferation and tube formation assays. Optimal dose of ABI-007 for metronomic therapy was determined by measuring the levels of circulating endothelial progenitors (CEPs) in peripheral blood of Balb/c non-tumor bearing mice (n=5/group; dosing: 1-30 mg/kg, i.p, qd×7) with flow cytometry (Shaked et al., *Cancer Cell,* 7:101-111 (2005)). Subsequently, the antitumor effects of metronomic (qd; i.p.) and MTD (qd×5, 1 cycle; i.v.) ABI-007 and Taxol® were evaluated and compared in SCID mice bearing human MDA-MD-231 breast and PC3 prostate cancer xenografts.

Results: ABI-007 at 5 nM significantly (p<0.05) inhibited rat aortic microvessel outgrowth, human endothelial cell proliferation and tube formation by 53%, 24%, and 75%, respectively. The optimal dose of ABI-007 for metronomic therapy was observed to be 6-10 mg/kg based on CEP measurements. Metronomic ABI-007 (6 mg/kg) but not Taxol® (1.3 mg/kg) significantly (p<0.05) suppressed tumor growth in both xenograft models. Neither ABI-007 nor Taxol® administered metronomically induced any weight loss. Although MTD ABI-007 (30 mg/kg) inhibited tumor growth more effectively than MTD Taxol® (13 mg/kg), significant weight loss was noted with the former. Interestingly, the antitumor effect of metronomic ABI-007 approximated that of MTD Taxol®.

Conclusion: ABI-007 exhibits potent antiangiogenic and antitumor activity when used in a metronomic regime.

Example 4b

Rat Aortic Ring Assay. Twelve-well tissue culture plates were coated with Matrigel (Collaborative Biomedical Products, Bedford, Mass.) and allowed to gel for 30 min at 37° C. and 5% $CO_2$. Thoracic aortas were excised from 8- to 10-week-old male Sprague-Dawley rats, cut into 1-mm-long cross-sections, placed on Matrigel-coated wells and covered with an additional Matrigel. After the second layer of Matrigel had set, the rings were covered with EGM-II and incubated overnight at 37° C. and 5% $CO_2$. EGM-II consists of endothelial cell basal medium (EBM-II; Cambrex, Walkersville, Md.) plus endothelial cell growth factors provided as the EGM-II Bulletkit (Cambrex). The culture medium was subsequently changed to EBM-II supplemented with 2% FBS, 0.25 µg/ml amphotericin B and 10 µg/ml gentamycin. Aortic rings were treated with EBM-II containing the vehicle (0.9% saline/albumin), carboxyamidotriazole (CAI; 12 µg/ml), or ABI-007 (0.05-10 nM paclitaxel) for 4 days and photographed on the fifth day. CAI, a known anti-angiogenic agent, was used at a higher than clinically achievable concentration as a positive control. Experiments were repeated four times using aortas from four different rats. The area of angiogenic sprouting, reported in square pixels, was quantified using Adobe Photoshop 6.0.

As shown in FIG. 1A, ABI-007 significantly inhibited rat aortic microvessel outgrowth in a concentration-dependent manner relative to the vehicle control, reaching statistical significance (p<0.05) at 5 nM (53% inhibition) and 10 nM (68% inhibition). The amount of albumin present at each concentration of ABI-007 alone did not inhibit angiogenesis.

Endothelial Cell Proliferation Assay. Human umbilical vein endothelial cells (HUVEC; Cambrex) were maintained in EGM-II at 37° C. and 5% CO2. HUVECs were seeded onto 12-well plates at a density of 30,000 cells/well and allowed to attach overnight. The culture medium was then aspirated, and fresh culture medium containing either the vehicle (0.9% saline/albumin), or ABI-007 (0.05-10 nM paclitaxel) was added to each well. After 48 h, cells were trypsinized and counted with a Coulter Z1 counter (Coulter Corp., Hialeah, Fla.). All experiments were repeated three times.

As shown in FIG. 1B, human endothelial cell proliferation was significantly inhibited by ABI-007 at 5 nM and 10 nM by 36% and 41%, respectively.

Endothelial Cell Tube Formation Assay. Eight-well slide chambers were coated with Matrigel and allowed to gel at 37° C. and 5% $CO_2$ for 30 min. HUVECs were then seeded at 30,000 cells/well in EGM-II containing either the vehicle (0.9% saline/albumin) or ABI-007 (0.05-10 nM paclitaxel) and incubated at 37° C. and 5% $CO_2$ for 16 h. After incubation, slides were washed in PBS, fixed in 100% methanol for 10 s, and stained with DiffQuick solution II (Dade Behring Inc., Newark, Del.) for 2 min. To analyze tube formation, each well was digitally photographed using a 2.5× objective. A threshold level was set to mask the stained tubes. The corresponding area was measured as the number of pixels using MetaMorph software (Universal Imaging, Downingtown, Pa.). Experiments were repeated three times.

As shown in FIG. 1C, ABI-007 blocked tube formation by 75% at both 5 nM and 10 nM.

Determination of the In Vivo Optimal Biologic Dose of ABI-007 by Measuring Circulating Endothelial Cells (CECs) and Circulating Endothelial Progenitors (CEPs). Six- to eight-week-old female Balb/cJ mice were randomized into the following eight groups (n=5 each): untreated, treated with i.p. bolus injections of either the drug vehicle (0.9% saline/albumin), or ABI-007 at 1, 3, 6, 10, 15 or 30 mg/kg paclitaxel daily for 7 days. At the end of the treatment period, blood samples were drawn by cardiac puncture and collected in EDTA-containing vacutainer tubes (Becton Dickinson, Franklin Lakes, N.J.). CECs and CEPs were enumerated using four-color flow cytometry. Monoclonal antibodies specific for CD45 were used to exclude CD45+ hematopoietic cells. CECs and their CEP subset were depicted using the murine endothelial markers fetal liver kinase 1/VEGF receptor 2 (flk-1/VEGFR2), CD13, and CD117 (BD Pharmingen, San Diego, Calif.). Nuclear staining (Procount; BD Biosciences, San Jose, Calif.) was performed to exclude the possibility of platelets or cellular debris interfering with the accuracy of CEC and CEP enumeration. After red cell lysis, cell suspensions were evaluated by a FACSCalibur (BD Biosciences) using analysis gates designed to exclude dead cells, platelets, and debris. At least 100,000 events/sample were obtained in order to analyze the percentage of CECs and CEPs. The absolute number of CECs and CEPs was then calculated as the percentage of the events collected in the CEC and CEP enumeration gates multiplied by the total white cell count. Percentages of stained cells were determined and compared to the appropriate negative controls. Positive staining was defined as being greater than non-specific background staining. 7-aminoactinomycin D (7AAD) was used to enumerate viable versus apoptotic and dead cells.

FIG. 2 shows that ABI-007 administered i.p. daily for 7 days at 3, 10-30 mg/kg significantly decreased CEP levels in non-tumor bearing Balb/cJ mice. However, ABI-007 at 10-30 mg/kg was associated with a significant reduction of white blood cell count indicative of toxicity. Although the reduction of CEP levels by ABI-007 at 6 mg/kg did not reach statistical significance, decrease in white blood cell count was not evident. Therefore it was concluded that the in vivo optimal biologic dose for metronomic ABI-007 was between 3-10 mg/kg. In one study, metronomic Taxol® at 1.3, 3, 6, or 13 mg/kg given i.p. daily for 7 days did not significantly reduce viable CEP levels, whereas metronomic Taxol® at 30 mg/kg or higher resulted in severe toxicity and eventually mortality in mice. It was previously reported that the i.p. administration of Taxol® at doses commonly used in the clinic resulted in entrapment of paclitaxel in Cremophor® EL micelles in the peritoneal cavity and consequently, insignificant plasma paclitaxel concentration (Gelderblom et al., *Clin. Cancer Res.* 8:1237-41 (2002)). This would explain why doses of metronomic Taxol® (1.3, 3, 6, and 13 mg/kg) that did not cause death failed to change viable CEP levels. In this case, the i.p. administration of metronomic Taxol® at 1.3 mg/kg would not be any different from that at 13 mg/kg. Therefore the lower dose, 1.3 mg/kg, was selected to minimize the amount of Cremophor® EL per paclitaxel administration for subsequent experiments.

Antitumor effects of metronomic and MTD ABI-007 compared with metronomic and MTD Taxol®. Human prostate cancer cell line PC3 and human breast cancer cell line MDA-MD-231 were obtained from the American Type Culture Collection (Manassas, Va.). PC3 cells ($5 \times 10^6$) were injected s.c. into 6- to 8-week-old male SCID mice, whereas MDA-MB-231 cells ($2 \times 10^6$) were implanted orthotopically into the mammary fat pad of female SCID mice. When the primary tumor volume reached approximately 150-200 mm$^3$, animals were randomized into eight groups (n=5-10/group). Each group was treated with either 0.9% saline/albumin vehicle control, Cremophor® EL vehicle control, metronomic Taxol® (1.3 mg/kg, i.p., qd), metronomic ABI-007 (3, 6, or 10 mg/kg paclitaxel, i.p., qd), MTD Taxol® (13 mg/kg, i.p., qd×5, 1 cycle), or MTD ABI-007 (30 mg/kg paclitaxel, i.v., qd×5, 1 cycle). Perpendicular tumor diameters were measured with a caliper once a week and their volumes were calculated. At the end of the treatment period, blood samples were drawn by cardiac puncture from mice in all groups. CECs and CEPs were enumerated as described herein.

Figure 3:
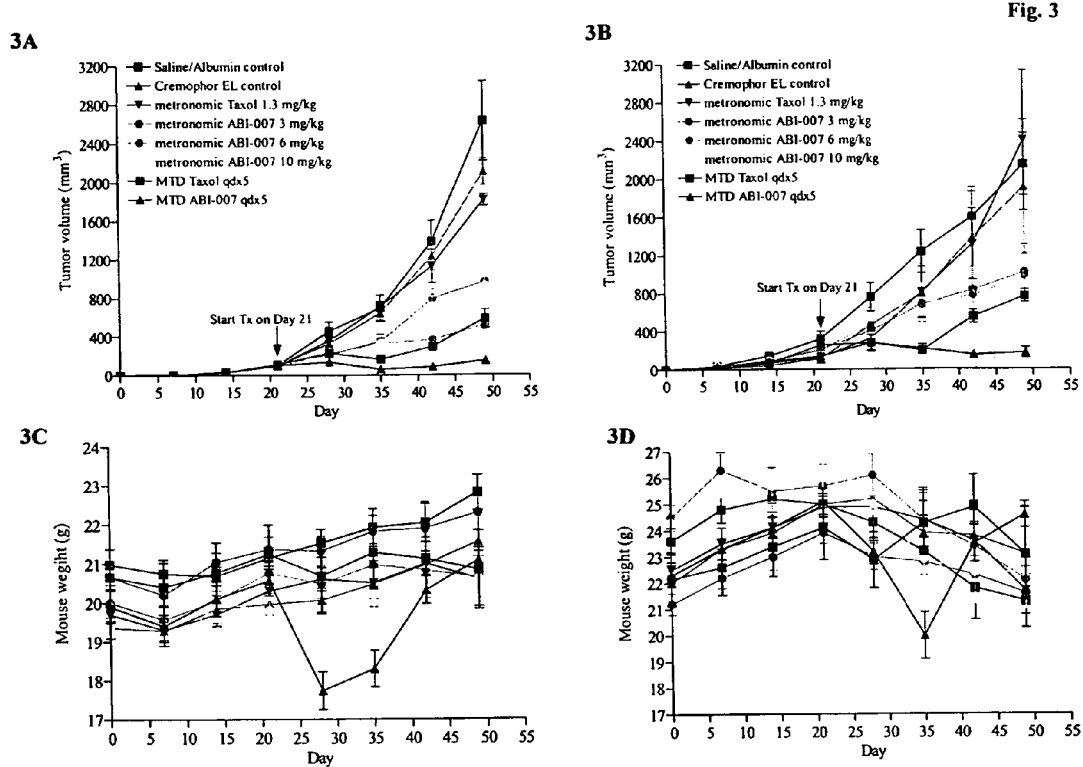
FIGS. 3A and 3B show the effects of ABI-007 and Taxol used in metronomic or MTD regimes on MDA-MB-231 (A) and PC3 (B) tumor growth tumor-bearing SCID mice.
FIGS. 3C and 3D show the effects of ABI-007 and Taxol used in metronomic or MTD regimes on the body weight of MDA-MB-231 (C) and PC3 (D) tumor-bearing SCID mice.

Metronomic ABI-007 (3, 6 and 10 mg/kg) but not Taxol® (1.3 mg/kg) administered i.p. daily for 4 weeks significantly (p<0.05) inhibited growth of both MDA-MB-231 and PC3 tumors (FIG. 3A and FIG. 3B). Neither ABI-007 nor Taxol® administered metronomically induced any weight loss (FIG. 3C and FIG. 3D). Although MTD ABI-007 (30 mg/kg) inhibited tumor growth more effectively than MTD Taxol® (13 mg/kg), significant weight loss was noted with the former, indicating toxicity. In addition, two out of five mice treated with MTD ABI-007 displayed signs of paralysis in one limb 6 days after the last dose of drug. The paralysis was transient and resolved within 24-48 hours. Interestingly, the antitumor effect of metronomic ABI-007 at 6 mg/kg approximated that of MTD Taxol® in the MDA-MB-231 xenograft model (FIG. 3A). Increasing the dose of metronomic ABI-007 to 10 mg/kg did not seem to confer more pronounced tumor growth inhibition. In contrast, metronomic ABI-007 elicited greater antitumor response at 10 mg/kg than at 3 and 6 mg/kg in the PC3 xenografts (FIG. 3B).

Figure 4:
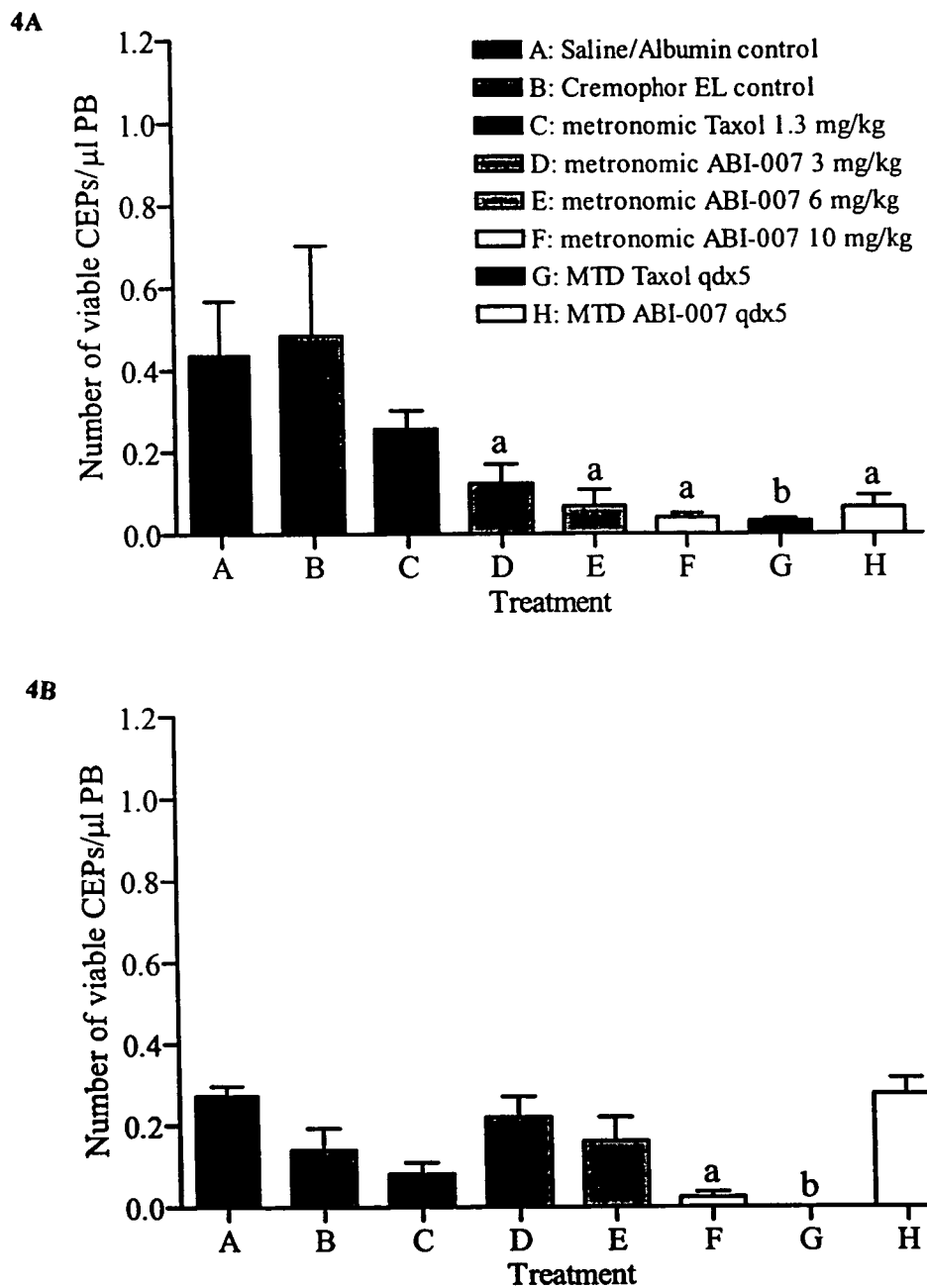
FIGS. 4A and 4B show changes in the levels of viable circulating endothelial progenitors (CEPs) in peripheral blood of MDA-MB-231 (FIG. 4A) and PC3 (FIG. 4B) tumor-bearing SCID mice after treatment with A, saline/albumin; B, Cremophor EL control; C, metronomic Taxol 1.3 mg/kg; D, E, and F, metronomic ABI-007 3, 6, and 10 mg/kg, respectively; G, MTD Taxol; H, MTD ABI-007. Bars, mean±SE. $^a$Significantly ($p<0.05$) different from saline/albumin vehicle control. $^b$Significantly ($p<0.05$) different from Cremophor EL vehicle control.

Metronomic ABI-007 significantly decreased the levels of viable CEPs in a dose-dependent manner in MDA-MB-231 tumor-bearing mice (FIG. 4A). Viable CEP levels also exhibited a dose-dependent reduction in response to metronomic ABI-007 in PC3 tumor-bearing mice, but reached statistical significance only at 10 mg/kg (FIG. 4B). The levels of CEPs were not altered by metronomic Taxol® in both xenograft models (FIGS. 4A and 4B).

Effects of metronomic and MTD ABI-007 and metronomic and MTD Taxol® on intratumoral microvessel density were studied. Five-um thick sections obtained from frozen MDA-MB-231 and PC3 tumors were stained with H&E for histological examination by standard methods known to one skilled in the art. For detection of microvessels, sections were stained with a rat anti-mouse CD31/PECAM-1 antibody (1:1000, BD Pharmingen) followed by a Texas Red-conjugated goat anti-rat secondary antibody (1:200, Jackson ImmunoResearch Laboratories, Inc., West Grove, Pa.). A single microvessel was defined as a discrete cluster or single cell stained positive for CD31/PECAM-1d, and the presence of a lumen was not required for scoring as a microvessel. The MVD for each tumor was expressed as the average count of the three most densely stained fields identified with a 20× objective on a Zeiss AxioVision 3.0 fluorescence microscopic imaging system. Four to five different tumors per each vehicle control or treatment group were analyzed.

Figure 5:
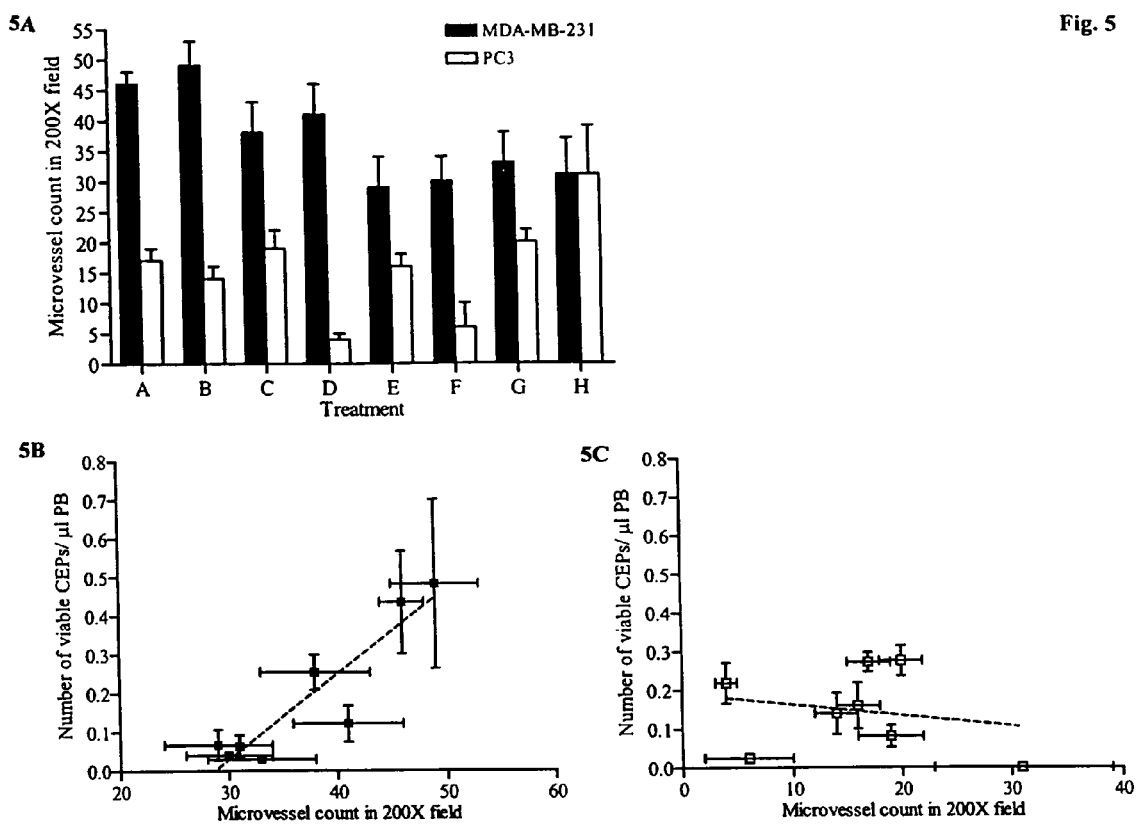
FIG. 5A shows intratumoral microvessel density of MDA-MB-231 (■) and PC3 (□) xenografts treated with A, saline/albumin; B, Cremophor EL control; C, metronomic Taxol 1.3 mg/kg; D, E, and F, metronomic ABI-007 3, 6, and 10 mg/kg, respectively; G, MTD Taxol; H, MTD ABI-007. Bars, mean±SE.
FIGS. 5B and 5C show the correlation between intratumoral microvessel density and the number of viable CEPs in peripheral blood in MDA-MB-231 (FIG. 5B) and PC3 (FIG. 5C) tumor-bearing SCID mice.

In MDA-MB-231 tumors, metronomic ABI-007 at 6 and 10 mg/kg as well as MTD ABI-007 seemed to reduce microvessel density (MVD) slightly although statistical significance was not reached (FIG. 5A). In PC3 tumors, metronomic ABI-007 at 3 and 10 mg/kg appeared to decrease MVD but without reaching statistical significance (FIG. 5A). Interestingly, a significant correlation existed between MVD and the level of viable CEPs in the MDA-MB-231 (FIG. 5B; r=0.76, P=0.04) but not in the PC3 (FIG. 5C; r=−0.071, P=0.88) model.

In vivo angiogenesis evaluation were carried out. A Matrigel plug perfusion assay was performed with minor modifications to methods known by one skilled in the art. Briefly, 0.5 ml Matrigel supplemented with 500 ng/ml of basic fibroblast growth factor (bFGF; R&D Systems Inc., Minneapolis, Minn.) was injected s.c. on day 0 into the flanks of 10-week-old female Balb/cJ mice. On day 3, animals were randomly assigned to eight groups (n=5 each). Each group was treated with either 0.9% saline/albumin vehicle control, Cremophor® EL vehicle control, metronomic Taxol® (1.3 mg/kg, i.p., qd), metronomic ABI-007 (3, 6, or 10 mg/kg paclitaxel, i.p., qd), MTD Taxol® (13 mg/kg, i.v., qd×5), or MTD ABI-007 (30 mg/kg paclitaxel, i.v, qd×5). As a negative control, five additional female Balb/cJ mice of similar age were injected with Matrigel alone. On day 10, all animals were injected i.v. with 0.2 ml of 25 mg/ml FITC-dextran (Sigma, St. Louis, Mo.). Plasma samples were subsequently collected. Matrigel plugs were removed, incubated with Dispase (Collaborative Biomedical Products, Bedford, Mass.) overnight at 37° C., and then homogenized. Fluorescence readings were obtained using a FL600 fluorescence plate reader (Biotech Instruments, Winooski, Vt.). Angiogenic response was expressed as the ratio of Matrigel plug fluorescence to plasma fluorescence.

Figure 6:
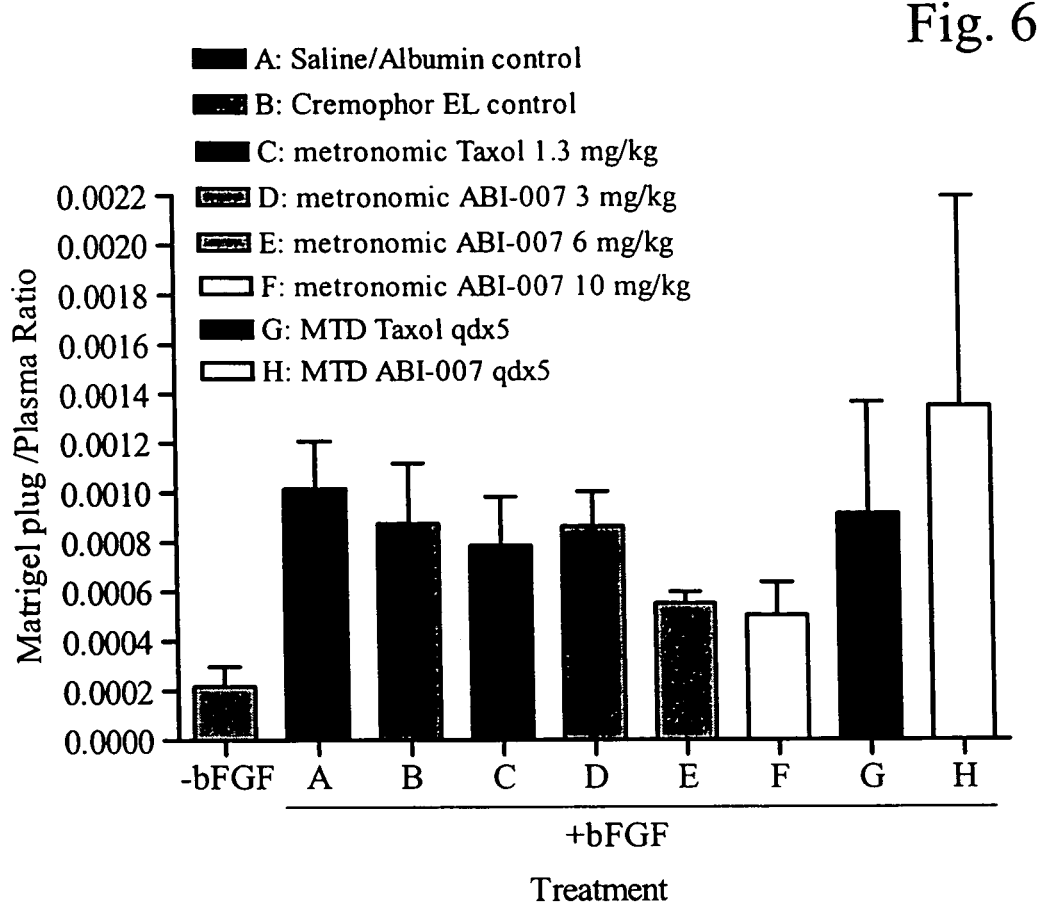
FIG. 6 shows the effects of ABI-007 or Taxol used in metronomic or MTD regimes on basic fibroblast growth factor (bFGF)-induced angiogenesis in matrigel plugs injected subcutaneously into the flanks of Balb/cJ mice. Treatments- A, saline/albumin; B, Cremophor EL control; C, metronomic Taxol 1.3 mg/kg; D, E, and F, metronomic ABI-007 3, 6, and 10 mg/kg, respectively; G, MTD Taxol; H, MTD ABI-007. Matrigel implanted without bFGF (-bFGF) served as negative control. Bars, mean±SE.

Metronomic ABI-007 at 6 and 10 mg/kg appeared to decrease angiogenesis although the inhibition did not reach statistical significance (FIG. 6). Angiogenesis seemed to be unaltered by metronomic ABI-007 at 3 mg/kg, MTD ABI-007, MTD and metronomic Taxol® relative to the respective vehicle controls (FIG. 6). These observations were similar to the intratumoral MVD results described herein.

Example 5

Nab-5109, A Nanoparticle Albumin-Bound IDN5109 (nab-5109) Shows Improved Efficacy and Lower Toxicity Over the Tween® Formulation (Tween®-5109, ORTATAXEL)

Methods: Nanoparticle nab-5109 was prepared using nab technology and characterized by laser light scattering. Nab-5109 and Tween-5109 were tested against Pgp+ DLD-1 (known to be resistant against paclitaxel and docetaxel—Vredenburg et al, *JNCI* 93: 1234-1245, 2001) human colon carcinoma xenograft in nude mice (n=5/group) at doses of 50 mg/kg (Tween®-5109, previously shown as MTD) and 75 mg/kg (nab-5109) given q3d×4, i.v. Control groups of PBS and human serum albumin (HSA) were also used.

Results: Nab-5109 yielded nanoparticles with mean size, $Z_{Ave}$=119 nm and Zeta potential=−32.7 mV. Nab-5109 was lyophilized to a dry powder that easily dispersed in saline. In vivo, there was significantly more weight loss (ANOVA, p<0.001) in the tumor bearing animals with Tween®-5109 (50 mg/kg, 8.8% wt loss) than with nab-5109 (75 mg/kg, 3.4% wt loss) indicating substantially lower toxicity of nab- 5109 despite the 50% higher dose. There was significant tumor suppression by nab-5109 and Tween®-5109 (ANOVA, p<0.0001 vs. controls) with tumor growth delays of 36 and 28 days respectively for nab-5109 (75 mg/kg) and Tween®-5109 (50 mg/kg). Nab-5109 was more effective than Tween®-5109 (ANOVA, p=0.0001) in suppressing tumor growth. There were no differences between the PBS and HSA control group in term of toxicity and efficacy.

Conclusion: Nanoparticle albumin-bound, nab-5109 was successfully prepared and could be given at 50% higher dose than Tween®-5109 with lower toxicity despite higher dose. At this higher dose, 75 mg/kg (q3d×4), nab-5109 showed significantly improved efficacy in the Pgp+ DLD-1 human colon xenograft compared with Tween®-5109.

Example 6

Nanoparticle Albumin Bound (nab) Dimeric Thiocolchicines nab-5404, nab-5800, and nab-5801: A Comparative Evaluation of Antitumor Activity vs Abraxane™ and Irinotecan Methods: Nanoparticle colchicines were prepared using nab technology. Cytotoxicity was evaluated in vitro using human MX-1 breast carcinoma cultures. In vivo anti-tumor activity (human HT29 colon tumor xenograft) in nude mice was compared against Irinotecan and Abraxane™. Dose levels for the nab-colchicines and Irinotecan were 20 mg/kg, 30 mg/kg, and 40 mg/kg, given q3d×4, i.v. Abraxane™ was dosed at its MTD, 30 mg/kg, given qd×5.

Results: The hydrophobic thiocolchicine dimers yielded nanoparticles with average size $Z_{Ave}$ (nm) of 119, 93, and 84 for nab-5404, nab-5800, and nab-5801, respectively. The nanoparticle suspensions were sterilized through 0.22 um filters and lyophilized. In vitro, nab-5404 was the most potent of the three analogs against MX-1 (p≦0.0005, ANOVA), ($IC_{50}$ (ug/ml): 18, 36 and 77 for nab-5404, nab-5800 and nab-5801 respectively) as well as against the HT29 xenograft in vivo (p≦0.0001, ANOVA). Tumor volume was suppressed by 93%, 79%, and 48% with nab-5404 at doses 40 mg/kg, 30 mg/kg, and 20 mg/kg, respectively. In contrast, tumor volume was only suppressed by 31%, 16%, and 21% with nab-5800; and 17%, 30%, and 23% with nab-5801 at 40 mg/kg, 30 mg/kg, and 20 mg/kg, respectively. Nab-5404 was more effective than Irinotecan at all dose levels (p≦0.008, ANOVA) with tumor volumes for Irinotecan suppressed by only 48%, 34%, and 29% at dose levels of 40 mg/kg, 30 mg/kg, and 20 mg/kg, respectively. In comparison to Abraxane™, nab-5404 was more active at equitoxic dose (ETD) based on equal weight loss (p<0.0001, ANOVA). Tumor volume was suppressed 93% by nab-5404 (40 mg/kg, q4d×3) and 80% by Abraxane™ (30 mg/kg, qd×5) at their respective ETDs.

Conclusions: Nab technology was utilized to convert 3 hydrophobic dimeric thiocolchicines (IDN5404, IDN5800, IDN5801) to nanoparticles suitable for I.V. administration. Nab-5404 had superior antitumor activity in vitro and in vivo compared to nab-5800 and nab-5801. Nab-5404 was more potent than Irinotecan at equal dose. At equitoxic dose, defined by weight loss, nab-5404 was more potent than Abraxane™. These data warrant further investigation of nab-5404.

Example 7

Abraxane™ vs Taxotere®: A Preclinical Comparison of Toxicity and Efficacy

Methods: Toxicity of Abraxane™ and Taxotere® was compared in a dose-ranging study in nude mice given the drugs on a q4d×3 schedule. The dose levels were Taxotere® 7, 15, 22, 33, and 50 mg/kg and ABX 15, 30, 60, 120, and 240 mg/kg. Antitumor activity of Abraxane™ and Taxotere® was compared in nude mice with human MX-1 mammary xenografts at a dose of 15 mg/kg weekly for 3 weeks.

Results: In the dose-escalation study in mice, the Taxotere® maximum tolerated dose (MTD) was 15 mg/kg and lethal dose ($LD_{100}$) was 50 mg/kg. In contrast, the Abraxane™ MTD was between 120 and 240 mg/kg and $LD_{100}$ was 240 mg/kg. In the tumor study Abraxane™ was more effective than equal doses of Taxotere® in tumor growth inhibition (79.8% vs 29.1%, p<0.0001, ANOVA).

Conclusion: Nanoparticle abumin-bound paclitaxel (Abraxane™) was superior to Taxotere® in the MX-1 tumor model when tested at equal doses. Furthermore, the toxicity of Abraxane™ was significantly lower than that of Taxotere®, which would allow dosing of Abraxane™ at substantially higher levels. These results are similar to the enhanced therapeutic index seen with Abraxane™ compared to Taxol® and suggest that the presence of surfactants may impair the transport, antitumor activity and increase the toxicity of taxanes. Studies in additional tumor models comparing Abraxane™ and Taxotere® are ongoing.

Example 8

A Nanoparticle Albumin Bound Thiocolchicine Dimer (nab-5404) with Dual Mechanisms of Action on Tubulin and Topoisomerase-1: Evaluation of In Vitro and In Vivo Activity Methods: IDN5404 was tested for cytotoxic activity using the MCF7-S breast carcinoma and its multidrug resistant variant, MCF7-R (pgp+). Its cytotoxicity was also assessed against the NCI-60 human tumor cell line panel. The nanoparticle albumin bound nab-5404 was administered IV using various schedules, to SCID mice implanted s.c. with a human A121 ovarian tumor xenograft.

Results: Against MCF7 cell lines, the parent compound, colchicine, demonstrated tumor growth inhibition with the IC50 value (50% growth inhibitory concentration) for MCF7-S cells at 3.9±0.2 nM. The resistant variant MCF7-R demonstrated an IC50 of 66±8.6 nM, approximately a 17-fold increase due to drug resistance. IDN5404, demonstrated increased activity against both cell lines, displaying IC50 values of 1.7±0.1 and 40±3.8 nM, respectively. These results were confirmed within the NCI 60 human tumor cell line panel with IDN5404 having a mean IC50 of <$10^{-8}$M and >10 fold resistance between the MCF7-S and the MCF7-R cell lines. The COMPARE algorithm identified IDN5404 as a tubulin binder similar to vinca alkaloids, confirming the previous results. In vivo against the A1121 ovarian tumor xenograft, efficacy and toxicity of nab-5404 was dose and schedule dependent. Nanoparticle nab-5404 was well tolerated and capable of inducing complete regressions and cures: at 24 mg/kg administered IV qd×5, 5 of 5 mice were long-term survivors (LTS) with no evidence of tumor. However, increasing the dosage to 30 mg/kg resulted in 5 of 5 toxic deaths. On a q3d×4 schedule, 30 mg/kg resulted in 4 of 5 mice LTS and at 50 mg/kg, 5 of 5 toxic deaths. Using a q7d×3 schedule, 40 mg/kg resulted in 3 of 5 mice LTS and at 50 mg/kg, 4 of 4 LTS were noted.

Conclusions: IDN5404, a new thiocolchicine dimer with dual mechanism of action showed activity in pgp-expressing, cisplatin and topotecan resistant cell lines. In vivo, nanoparticle albumin bound nab-5404 was active against A121 ovarian xenografts.

Example 9

Combination Studies of Abraxane™ and Other Agents

Due to the advantageous properties of Abraxane™ (ABX, the nanoparticle albumin-bound paclitaxel) noted above, it was used and being used in a number of studies with different modes of administration and schedules and in combination with other oncology drugs as well as radiation treatment. These are listed below:

In metastatic breast cancer, these studies include:

| | | |
|---|---|---|
| Randomized Phase II Trial of Weekly Abraxane ™ in Combination with Gemcitabine in Individuals with HER2 Negative Metastatic Breast Cancer | ABX 125, Gem 1000 mg/m$^2$, D1, 8; q 3wk | To evaluate the combination of ABX and Gemcitabine in 1st-line MBC. |
| A phase II study of weekly dose-dense nanoparticle paclitaxel (ABI-007) carboplatin, with Herceptin ® as first or second-line therapy of advanced HER2 positive breast cancer | ABX 100 mg/m$^2$, Carbo AUC 2, both D1, 8, 15; Her 2 mg/kg (4 mg/kg on wk a) q4wk × 6 | Data will be important for using ABX in combination with carbo and/or Herceptin ®. Also helpful for other combinations. |
| Weekly Vinorelbine and Abraxane ™, with or without G-CSF, in stage IV breast cancer: a phase I-II study | L1: ABX 80, Nav 15; L2: ABX 90, Nav 20; L3: ABX 100, Nav 22.5; L4: ABX 110, Nav 25; L5: ABX 125, Nav 25 qwk | Multi-center study of ABX in combination with Navelbine ® in 1st-line MBC. |
| Phase II trial of weekly Abraxane ™ monotherapy for 1st-line MBC (plus Herceptin ® in Her2+ pts) | ABX 125 mg/m$^2$ Q3/4wk | A relatively large phase II of weekly ABX monotherapy at 125 mg/m$^2$ in 1st-line MBC. |
| Phase I/II trial Abraxane ™ plus Doxil ® for MBC plus limited PK | ABX + Anthracycline | |
| 3-arm phase II trial in 1st-line MBC | ABX weekly (130 mg/m$^2$) vs. q2wk (260 mg/m$^2$) vs. q3wk (260 mg/m$^2$) | To optimize ABX monotherapy regime for MBC |
| 3-arm phase II trial in 1st-line and 2nd-line MBC, with biological correlates analyses | ABX weekly vs. ABX q3wk vs. Taxol ® weekly | randomized ABX MBC trial to obtain important data: weekly ABX vs. weekly Taxol ®; weekly ABX vs. 3-weekly ABX; plus biomarker study (caveolin-1 and SPARC). |
| Phase I/II Abraxane ™ + GW572016 | TBD | combination of ABX and GW572016 (a dual EGFR inhibitor and one of the most promising new biological agents for BC). |
| A phase I dose escalation study of a 2 day oral gefitinib chemosensitization pulse given prior to weekly Abraxane ™ in individuals with advanced solid tumors | Abraxane ™ 100 mg/m$^2$ weekly, 3 out of 4 weeks; Gefitinib starting at 1000 mg/d × 2 days | This phase I trial is to determine the safety and tolerability of a 2 day gefitinib pulse given prior to Abraxane ™ administration. |
| Phase II 1$^{st}$ line MBC trial | weekly ABX (125 mg/m$^2$, 2 wk on and 1 wk off) + Xeloda ® 825 mg/m$^2$ d 1-14 q3wk | To evaluate the combination of ABX and Xeloda ® in 1st-line MBC, using 2 weekly on and 1 weekly off ABX regime. |
| Phase II pilot adjuvant trial of Abraxane ™ in breast cancer | Dose dense AC + G CSF --> weekly ABX --> Avastin ® | A pilot adjuvant study of a "super dose dense" |
| Abraxane ™ in dose-dense adjuvant chemotherapy for early stage breast cancer | AC q2w × 4 + G CSF --> ABX q2wk × 4 | A pilot adjuvant study of dose dense ABX regime - an alternate of a standard adjuvant regime |
| Phase II pilot adjuvant trial of Abraxane ™ in breast cancer | AC Q2wk --> ABX q2wk + G-CSF | A pilot adjuvant study in preparation for phase III adjuvant trial |

In Breast cancer neoadjuvant setting studies include:

| | | |
|---|---|---|
| Phase II Trial of Dose Dense Neoadjuvant Gemcitabine, Epirubicin, ABI-007 (GEA) in Locally Advanced or Inflammatory Breast Cancer | Neoadjuvant: Gem 2000, Epi 60, ABX 175 mg/m$^2$, Neul 6 mg SC, all D1 q2wk × 6 Adjuvant: Gem 2000, ABX 220, Neul 6 mg D1 q2wk × 4 | This neoadjuvant study is based on the GET data from Europe which showed high activity. In the current regime, ABX will replace T, or Taxol ®. |
| Phase II preoperative trial of Abraxane ™ followed by FEC (+Herceptin ® | ABX 220 mg/m$^2$ q2wk × 6 followed by FEC × 4 (+Herceptin ® for Her2+ | |

| | | |
|---|---|---|
| as appropriate) in breast cancer | pts) | |
| Pre-clinical study of drug-drug interaction | ABX + other agents | |
| Phase II neoadjuvant | (ABX + Herceptin ®) followed by (Navelbine ® + Herceptin ®) | |
| Randomized phase II trial of neoadjuvant chemotherapy in individuals with breast cancer | TAC vs. AC followed ABX + carbo vs. AC followed ABX + carbo + Herceptin ® | To evaluate AC followed by ABX/carbo or ABX/carbo/Herceptin ® combinations vs TAC (a FDA approved adjuvant BC regime) in neoadjuvant setting. |
| Phase II neoadjuvant trial of Abraxane ™ and capecitabine in locally advanced breast cancer | ABX: 200 mg/m² D1; Xel: 1000 mg/m² D1-14; q3wk × 4 | |
| Phase II trial of neoadjuvant chemotherapy (NCT) with nanoparticle paclitaxel (ABI-007, Abraxane ™) in women with clinical stage IIA, IIB, IIIA, IIIB, and IV (with intact primary) breast cancers | ABX: 300 mg/m² q3wk | |

In lung cancer the studies include:

| | | |
|---|---|---|
| Phase I/II study of Abraxane ™ monotherapy in 1st-line advanced NSCLC | ABX weekly | The first phase II trial of ABX combo with carbo in NSCLC. |
| Phase II Trial of weekly Abraxane ™ plus carboplatin in 1st-line NSCLC | ABX: 125 mg/m² D1, 8, 15; Carbo: AUC 6 D1; q4 wk | |
| A Phase I Trial of Carboplatin and Abraxane ™ on a weekly and every three week schedule in individuals with Advanced Solid Tumor Malignancies | Arm 1: ABX 100, 125, 150 mg/m² D1, 8, 15 q4wk; Arm 2: ABX 220, 260, 300 mg/m² D1 q3wk. Carbo AUC6 in both arms | This 2-arm phase I study will generate important data on ABX/carbo combination for further studies of this combo in multiple diseases. |
| Phase II study of ABI 007 (Abraxane ™) and carboplatin in advanced non-small cell lung cancer. | ABX Level(a): 225 mg/m2; Level(b): 260 mg/m2; Level(3): 300 mg/m2; q3wk Carbo fixed at AUC6 q3wk | This phase II NSCLC study will generate data for a future phase III registration trial in lung cancer |
| Phase I study of ABI 007 (Abraxane ™) and carboplatin | ABX q3wk | |
| Phase I/II study of Abraxane ™ + Alimta ® for 2nd-line NSCLC | TBD | ABX and Alimta ® can be a promising combination due to the non-overlapping toxicity profiles. |
| Phase I/II trial of Abraxane ™ plus cisplatin in advanced NSCLC | | |
| Phase I/II study of Abraxane ™, Navelbine ®, and Cisplatin for treatment of advanced NSCLC | | |
| Phase II ABX mono in 1st-line NSCLC | ABX 260 mg/m² q3wk | The 1st ABX trial in NSCLC. |
| Phase II study of Abraxane ™ monotherapy in 2nd-line NSCLC | Cohort 1: ABX q3 wk; Cohort 2: ABX weekly. Doses TBD | |
| Phase I/II trial of weekly Abraxane ™ and carboplatin in advanced NSCLC | 1st line | |

Studies in Prostate include:

| | | |
|---|---|---|
| Randomized phase II ABX weekly vs Q3W in front line HRP | 100 mg/m² weekly vs 260 mg/m² q3wk | |
| Phase II ABX in 1st-line prostate cancer | weekly ABX | |
| Phase II study of weekly ABX in 1st-line HRPC | | |
| Phase II neoadjuvant study | TBD | A multi-center neoadjuvant trial of ABX in prostate cancer plus biomarker study. |
| Phase II ABX 100 mg weekly no break | | |

Studies in ovarian cancer include:

| | |
|---|---|
| Phase II study of Abraxane ™ for treatment of advanced ovarian cancer (3rd-line) | TBD |
| Phase I study of Abraxane ™ plus carbo for treatment of advanced ovarian cancer | ABX weekly + Carbo AUC 6 |
| A phase II trial of Abraxane ™/Carboplatin in recurrent ovarian cancer | |

Studies in Chemoradiation include:

| | |
|---|---|
| Phase I/II trial of Abraxane ™ combined with radiation in NSCLC | |
| Abraxane ™ Combined With Radiation | animal model |
| H&N (Head and Neck Cancer) | TBD |

Other studies include:

| | |
|---|---|
| Phase II study of ABX in treatment of persistent or recurrent carcinoma of the cervix | 125 mg/m² d1, 8, 15 q28 days |
| PhII in preciously treated (100 ABX) and untreated (150 ABX) metastatic melanoma | 26-->70 |
| Ph II single treatment use of ABI-007 for the treatment of non-hematologic malignancies | |
| Abraxane ™ Combined With antiangiogenic agents, e.g., Avastin ®. | |
| Abraxane ™ Combined With proteasome inhibitors e.g., Velcade ®. | |
| Abraxane ™ Combined With EGFR inhibitors e.g., Tarceva ®. | |
| A randomized phase II trial of weekly gemcitabine, Abraxane ™, and external irradiation for locally advanced pancreatic cancer | |

Example 10

Combination of Nanoparticle Invention Drugs with Other Agents and Modes of Therapy Lower toxicity of nanoparticle invention drugs described herein allow combination with other oncology drugs and other modes of treatment with more advantageous outcome. These include nanoparticle forms of paclitaxel, docetaxel, other taxanes and analogs, geldanamycins, colchicines and analogs, combretastatins and analogs, hydrophobic pyrimidine compounds, lomaiviticins and analogs including compounds with the lomaiviticin core structures, epothilones and analogs, discodermolide and analogs and the like. The invention drugs may be combined with paclitaxel, docetaxel, carboplatin, cisplatin, other platins, doxorubicin, epirubicin, cyclophosphamide, iphosphamide, gemcitabine, capecitabine, vinorelbine, topotecan, irinotecan, tamoxifen, camptothecins, 5-FU, EMP, etoposide, methotraxate and the like.

Example 11

Combination of Abraxane™ with Carboplatin and Herceptin®

The combination of Taxol® and carboplatin has shown significant efficacy against metastatic breast cancer. On a weekly schedule, in this combination, Taxol® can only be dosed at up to 80 mg/m². Higher doses cannot be tolerated due to toxicity. In addition, HER-2-positive individuals derive greater benefit when Herceptin® is included in their therapeutic regime. This open-label Phase II study was conducted to determine the synergistic therapeutic effect of ABI-007 (Abraxane™) with these agents. The current study was initiated to evaluate the safety and antitumor activity of ABI-007/carboplatin with Herceptin® for individuals with HER-2 positive disease. ABI-007 was given in combination with carboplatin and Herceptin® administered intravenously weekly to individuals with HER-2 positive advanced breast cancer. A cohort of 3 individuals received ABI-007 at a dose of 75 mg/m² IV followed by carboplatin at target AUC=2 weekly and Herceptin® infusion (4 mg/kg at week 1, and 2 mg/kg on all subsequent weeks) for 1 cycle. These individuals tolerated the drug very well so for all subsequent cycles and individuals the dose of ABI-007 was escalated to 100 mg/m². Six individuals were treated to date. Of the 4 individuals that were evaluated for response, all 4 (100%) showed a response to the therapy. It should be noted that due to lower toxicity of Abraxane™, a higher total paclitaxel dose could be given compared to Taxol® with resulting benefits to the individuals.

Example 12

Combination of Abraxane™ with Carboplatin

The combination of Taxol® and carboplatin has shown significant efficacy in lung cancer. Another study with Abraxane™ in combination with carboplatin on a 3 weekly schedule in individuals with lung cancer is ongoing.

Example 13

Use of Abraxane™ in Combination with Radiation

Example 13a

Abraxane™, combined with clinical radiotherapy, enhances therapeutic efficacy and reduces normal tissue toxicity. Abraxane™ is used to increase the therapeutic gain of radiotherapy for tumors; to enhance tumor response to single and fractionated irradiation; to enhance normal tissue response to radiation and to increase therapeutic ratio of radiotherapy.

A murine ovarian carcinoma, designated OCa-I, which has been investigated extensively is used. First, optimal timing of Abraxane™ administration relative to local tumor radiation is timed to produce maximum antitumor efficacy. Tumors are generated in the right hind leg of mice by i.m. injection of tumor cells and treatment is initiated when the tumors reach 8 mm in size. Mice are treated with 10 Gy single dose irradiation, a single dose of Abraxane™ or with combination therapy of Abraxane™ given at different times 5 days before to 1 day after irradiation. A dose of Abraxane™ equal to about 1½ times more than the maximum tolerated dose of paclitaxel is used, a dose of 90 mg/kg. The endpoint of efficacy is tumor growth delay. The groups consist of 8 mice each. Tumors are generated and treated as described in Aim 1. The endpoint of efficacy is tumor growth delay. Tumors are irradiated with 5, 7.5 or 10 Gy delivered either in a single dose or in fractionated doses of 1, 1.5 or 2 Gy radiation daily for five consecutive days. Since Abraxane™ is retained in the tumor for several days and exerts its enhancing effect on each of the five daily fractions, Abraxane™ is given once at the beginning of the radiation regime. Since the ultimate goal in clinical radiotherapy is to achieve tumor cure, the potential for Abraxane™ to enhance tumor radiocurability is determined. The same scheme as described for the fractionated tumor growth delay study is used, except that a range of doses from 2 to 16 Gy is given daily for five consecutive days (total radiation dose 10 to 80 Gy). Tumors are followed for regression and regrowth for up to 120 days after irradiation, when TCD50 (the dose of radiation needed to yield local tumor cure in 50 percent of animals) is determined. There are two TCD50 assays: radiation only and Abraxane™ plus radiation, and each assay consists of 10 radiation dose groups containing 15 mice each. To provide therapeutic gain, any radioenhancing agent, including Abraxane™, must increase tumor radioresponse more than increase normal tissue damage by radiation. Damage to jejunal mucosa, a highly proliferative tissue affected by taxanes is assessed. The jejunal microcolony assay is used to determine the survival of crypt epithelial cells in the jejunum of mice exposed to radiation. Mice are exposed to whole body irradiation (WBI) with daily doses of X-rays ranging from 3 to 7 Gy for five consecutive days. The mice are treated with Abraxane™, at an equivalent paclitaxel dose of 80 mg/kg, administered i.v. 24 h before the first dose of WBI and killed 3.5 days after the last dose of WBI. The jejunum is prepared for histological examination, and the number of regenerating crypts in the jejunal cross-section is counted. To construct radiation survival curves, the number of regenerating crypts is converted to the number of surviving cells.

Example 13b

The objective of this study was to assess whether ABI-007 (a) as a single agent has antitumor activity against the syngeneic murine ovarian carcinoma OCa-1 and (b) enhances the radiation response of OCa-1 tumors in a combined treatment regime as described in the previous example with the following modifications.

OCa-1 tumor cells were injected i.m. into the hind leg of C3H mice. When tumors grew to a mean diameter of 7 mm, single treatment with local radiation (10 Gy) to the tumor-bearing leg, ABI-007 90 mg/kg i.v., or both, was initiated. To determine the optimal treatment scheduling, ABI-007 was given from 5 days to 9 hours before radiation as well as 24 hours after radiation. Treatment endpoint was absolute tumor growth delay (AGD), defined as the difference in days to grow from 7-12 mm in diameter between treated and untreated tumors. For groups treated with the combination of ABI-007 and radiation, an enhancement factor (EF) was calculated as the ratio of the difference in days to grow from 7 to 12 mm between the tumors treated with the combination and those treated with ABI-007 alone to the AGD of tumors treated with radiation only. To assess the radiation-enhancing effect of ABI-007 for a fractionated radiation regime on the endpoint tumor cure, a TCD50 assay was performed and analyzed 140 days post treatment. Total doses of 5 to 80 Gy in 5 daily fractions were administered either alone or combined with ABI-007 24 hours before the first radiation dose.

As a single agent, ABI-007 significantly prolonged the growth delay of the OCa-1 tumor (37 days) compared to 16 days for untreated tumors. ABI-007 as a single agent was more effective than a single dose of 10 Gy, which resulted in a delay of 29 days. For combined treatment regimes, ABI-007 given at any time up to 5 days before radiation, produced a supra-additive antitumor effect. EF was 1.3, 1.4, 2.4, 2.3, 1.9, and 1.6 at intertreatment intervals of 9 h, 24 h and 2, 3, 4, and 5 days, respectively. When ABI-007 was given after radiation, the combined antitumor treatment effect was less than additive. Combined treatment with ABI-007 and radiation also had a significant effect on tumor cure by shifting the TCD50 of 55.3 Gy for tumors treated with radiation only to 43.9 Gy for those treated with the combination (EF 1.3).

This experiment demonstrated that ABI-007 possesses single-agent antitumor activity against OCa-1 and enhances the effect of radiotherapy when given several days prior. As previously demonstrated for paclitaxel and docetaxel, the radiation enhancement is likely a result of multiple mechanisms, with a cell cycle arrest in G2/M being dominant at short treatment intervals and tumor reoxygenation at longer intervals.

Example 14

Combination of Abraxane™ and Tyrosine Kinase Inhibitors

Pulse-dosing of gefitinib in combination with the use of Abraxane™ is useful to inhibit the proliferation of EGFr expressing tumors. 120 nude mice are inoculated with BT474 tumor cells to obtain at least 90 mice bearing BT474 xenograft tumors and split into 18 experimental arms (5 mice each). Arm 1 mice receive control i.v. injections. All other mice receive weekly i.v. injections of Abraxane™ at 50 mg/kg for 3 weeks. Arm 2 receive Abraxane™ alone. Arms 3, 4, 5, 6, 7, 8 receive weekly Abraxane™ preceded by 2 days of a gefitinib pulse at increasing doses. Arms 9, 10, 11, 12, 13 receive weekly Abraxane™ preceded by one day of a gefitinib pulse at increasing doses. Arms 14, 15, 16, 17, 18 receive weekly Abraxane™ along with everyday administration of gefitinib at increasing doses. The maximum tolerated dose of gefitinib that can be given in a 1 or 2 day pulse preceding weekly Abraxane™ or in continuous administration with Abraxane™ is established. In addition, measurement of antitumor responses will determine whether a dose-response relationship exists and whether 2 day pulsing or 1 day pulsing is superior. These data are used to select the optimal dose of pulse gefitinib and that of continuous daily gefitinib given with Abraxane™.

120 nude mice are inoculated with BT474 tumor cells to obtain 90 mice bearing tumors. These mice are split into 6 groups (15 each). Arm 1 receive control i.v. injections. Arm 2 receive Abraxane™ 50 mg/kg i.v. weekly for 3 weeks. Arm 3 receive oral gefitinib at 150 mg/kg/day. Arm 4 receive Abraxane™ 50 mg/kg along with daily gefitinib at the previously established dose. Arm 5 receive Abraxane™ 50 mg/kg preceded by a gefitinib pulse at the previously established dose and duration. Arm 6 receive only a weekly gefitinib pulse at the previously established dose. After three weeks of therapy, mice are followed until controls reach maximum allowed tumor sizes.

Example 15

Phase II Study of Weekly, Dose-Dense nab™-Paclitaxel (Abraxane™), Carboplatin with Trastuzumab® as First-Line Therapy of Advanced HER-2 Positive Breast Cancer This study aimed to evaluate (1) the safety and tolerability and (2) the objective response rate of weekly dose-dense trastuzumab/Abraxane™/carboplatin as first-line cytotoxic therapy for patients with advanced/metastatic (Stage IV adenocarcinoma) HER-2-overexpressing breast cancer. Trastuzumab is a monoclonal antibody, also known as Herceptin®, which binds to the extracellular segment of the erbB2 receptor.

Briefly, patients without recent cytotoxic or radiotherapy were included. Doses of Abraxane™ were escalated from 75 mg/m$^2$ as 30-min i.v. infusions on days 1, 8, 15 up to 100 mg/m$^2$ for subsequent cycles according to the standard 3+3 rule. Carboplatin AUC=2 was given as 30-60 min i.v. infusions on days 1, 8, 15 and for an initial 29 day cycle. Trastuzumab was given as i.v. 30-90 min infusion on days 1, 8, 15, 22 at a dose of 4 mg/kg at week 1 and 2 mg/kg on all subsequent weeks.

Of 8 out of 9 patients evaluable for response the response rate (confirmed plus unconfirmed) was 63% with 38% stable disease. The most common toxicities were neutropenia (grade 3: 44%; grade 4: 11%) and leukocytopenia (33%).

These results suggest that trastuzumab plus Abraxane™ plus carboplatin demonstrated a high degree of antitumor activity with acceptable tolerability as a first-line therapy for MBC.

Example 16

Phase II Trial of Capecitabine Plus nab™-Paclitaxel (Abraxane™) in the First Line Treatment of Metastatic Breast Cancer The purpose of this phase II study was to evaluate the safety, efficacy (time to progression and overall survival), and quality of life of patients with MBC who received capecitabine in combination with Abraxane™. Capecitabine is a fluoropyrimidine carbamate also known as Xeloda® which has been shown to have substantial efficacy alone and in combination with taxanes in the treatment of MBC.

In this open-label, single-arm study, Abraxane™ 125 mg/m$^2$ was given by i.v. infusion on day 1 and day 8 every 3 weeks plus capecitabine 825 mg/m$^2$ given orally twice daily on days 1 to 14 every 3 weeks. Patients were HER-2/neu negative with a life expectancy of greater than 3 months. Patients had no prior chemotherapy for metastatic disease, no prior capecitabine therapy, and no prior fluoropyrimidine therapy and paclitaxel chemotherapy given in an adjuvant setting.

12 patients have been enrolled with safety analysis completed on the first 6 patients and the response rate evaluable after 2 cycles in the first 8 patients. There were no unique or unexpected toxicities with no grade 4 toxicities or neuropathy greater than grade 1. Response data were confirmed on only the first 2 cycles of therapy (first evaluation point) in 6 patients. Two patients have completed 6 cycles with 1 partial response and 1 stable disease. Of the first 8 patients after 2 cycles, there were 2 partial responses and 4 with stable disease.

These results show that combination of capecitabine and weekly Abraxane™ at effective doses is feasible with no novel toxicities to date. Abraxane™ related toxicity was mainly neutropenia without clinical consequences, and hand foot syndrome was the major toxicity of capecitabine.

Example 17

Pilot Study of Dose-Dense Doxorubicin Plus Cyclophosphamide Followed by nab-Paclitaxel (Abraxane™) in Patients with Early-Stage Breast Cancer The objective of this study was to evaluate the toxicity of doxorubicin (adriamycin) plus cyclophosphamide followed by Abraxane™ in early stage breast cancer.

Patients had operable, histologically confirmed breast adenocarcinoma of an early stage. The patients received doxorubicin (adriamycin) 60 mg/m$^2$ plus cyclophosphamide 600 mg/m$^2$ (AC) every 2 weeks for 4 cycles followed by Abraxane™ 260 mg/m$^2$ every two weeks for 4 cycles.

30 patients received 4 cycles of AC, and 27 of 29 patients received 4 cycles of Abraxane™; 33% of patients received pegfilgrastim (Neulasta®) for lack of recovery of ANC (absolute neutrophil count) during Abraxane™. Nine patients (31%) had Abraxane™ dose reductions due to non-hematologic toxicity. A total of 9 patients had grade 2 and 4 patients had grade 3 peripheral neuropathy (PN); PN improved by ≧1 grade within a median of 28 days.

These results indicate that dose-dense therapy with doxorubicin (60 mg/m$^2$) plus cyclophosphamide (600 mg/m$^2$) every 2 weeks for 4 cycles followed by dose-dense Abraxane™ (260 mg/m$^2$) every 2 weeks for 4 cycles was well tolerated in patients with early-stage breast cancer.

Example 18

Weekly nab-Paclitaxel (Abraxane™) as First Line Treatment of Metastatic Breast Cancer with Trastuzumab Add On for HER-2/neu-Positive Patients The purpose of the current study was to move weekly Abraxane to a front-line setting and add trastuzumab for HER2/neu-positive patients.

This phase II, open-label study included 20 HER2-postivive and 50 HER2-negative patients with locally advanced or metastatic breast cancer. Abraxane™ was given at 125 mg/m$^2$ by 30 minute i.v. infusion on days 1, 8, and 15 followed by a week of rest. Trastuzumab was given concurrently with study treatment for patients who were HER2-positive. The primary endpoint was response rate and the secondary endpoints were time to progression (TTP), overall survival (OS), and toxicity.

In the safety population, 23 patients received a median of 3 cycles of Abraxane™ to date. The most common treatment-related adverse event was grade 3 neutropenia (8.7%) with no grade 4 adverse events. One out of 4 evaluable patients responded to therapy.

Example 19

Phase I Trial of nab-Paclitaxel (Abraxane™) and Carboplatin

The aim of the current study was to determine the maximum tolerated dose of Abraxane™ (both weekly and every 3 weeks) with carboplatin AUC=6 and to compare the effects of sequence of administration on pharmacokinetics (PK).

Patients with histologically or cytologically documented malignancy that progressed after "standard therapy" were included. Arm 1 received Abraxane™ every 3 weeks in a dose escalation format based on cycle 1 toxicities (220, 260, 300, 340 mg/m²) every 3 weeks followed by carboplatin AUC=6. Arm 2 received weekly (days 1, 8, 15 followed by 1 week off) Abraxane™ (100, 125,150 mg/m²) followed by carboplatin AUC=6. For the PK portion of the study, Abraxane™ was followed by carboplatin in cycle 1 and the order of administration reversed in cycle 2 with PK levels determined at initial 6, 24, 48 and 72 hours.

On the every 3 weeks schedule, neutropenia, thrombocytopenia and neuropathy were the most common grade 3/4 toxicities (3/17 each). On the weekly schedule, neutropenia 5/13 was the most common grade 3/4 toxicity. The best responses to weekly administration at the highest dose of 125 mg/m² (n=6) were 2 partial responses (pancreatic cancer, melanoma) and 2 stable disease (NSCLC). The best responses to the every three week administration at the highest dose of 340 mg/m² (n=5) were 1 stable disease (NSCLC) and 2 partial responses (SCLC, esophageal).

These data indicate activity of combination of Abraxane™ and carboplatin. The MTD for the weekly administration was 300 mg/m², and for the once every 3 week administration was 100 mg/m².

Example 20

Phase II Trial of Dose-Dense Gemcitabine, Epirubicin, and nab-Paclitaxel (Abraxane™) (GEA) in Locally Advanced/Inflammatory Breast Cancer In an open-label, phase II study an induction/neoadjuvant therapy regime was instituted prior to local intervention. The therapy regime was gemcitabine 2000 mg/m² i.v. every 2 weeks for 6 cycles, epirubicin 50 mg/m² every 2 weeks for 6 cycles, Abraxane™ 175 mg/m² every 2 weeks for 6 cycles, with pegfilgrastim 6 mg s.c. on day 2 every 2 weeks. The postoperative/adjuvant therapy regime after local intervention was gemcitabine 2000 mg/m² every 2 weeks for 4 cycles, Abraxane™ 220 mg/m² every 2 weeks for 4 cycles and pegfilgrastim 6 mg s.c. day every 2 weeks. Patients included females with histologically confirmed locally advanced/inflammatory adenocarcinoma of the breast.

Example 21

Cytotoxic Activity of nab-Rapamycin in Combination with Abraxane™ on Vascular Smooth Muscle Cells Vascular smooth muscle cells (VSMC) were seeded onto 96 wells plates in the presence of increasing concentrations of nab-rapamycin and 0 μM, 1 μM, 10 μM, or 100 μM of Abraxane™ (ABI-007). To evaluate the cytotoxic effect of nab-rapamycin and Abraxane™, treated VSMCs were stained with ethidium homodimer-1 (Invitrogen, Carlsbad Calif.) and analyzed for red fluorescence. Ethidium homodimer-1 is a high-affinity, fluorescent nucleic acid stain that is only able to pass through compromised membranes of dead cells to stain nucleic acids. As shown in FIG. 7A, nab-rapamycin, by itself, exhibited dose-dependent cell killing as demonstrated by increasing fluorescence. Cell killing by nab-rapamycin was not enhanced by Abraxane™ at 1 μM or 10 μM; however, it was greatly enhanced by Abraxane™ at 100 μM (ANOVA, p<0.0001). Cells stained with ethidium homodimer-1 as shown in FIG. 7A were also exposed to calcein. Calcein AM (Invitrogen) is a non-fluorescent molecule that is hydrolyzed into fluorescent calcein by nonspecific cytosolic esterases. Live cells exposed to calcein AM exhibit bright green fluorescence as they are able to generate the fluorescent product and retain it. As shown in FIG. 7B, nab-rapamycin exhibited dose dependent cytotoxic activity as shown by a reduced amount of fluorescent staining by calcein. This reduction in fluorescence was enhanced by coincubation with Abraxane™ in a dose dependent manner. ANOVA statistic gave p<0.0001 at all drug concentrations of Abraxane™.

Example 22

Figure 8:
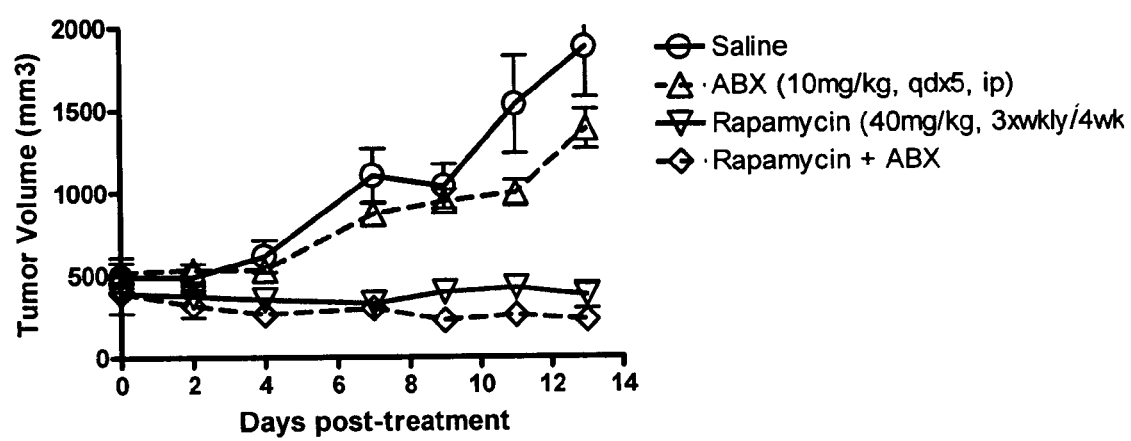
FIG. 8 shows the cytotoxic activity of nab-rapamycin in combination with Abraxane™ in a HT29 human colon carcinoma xenograft model.

Cytotoxic Activity of nab-Rapamycin in Combination with Abraxane™ Against HT29 (Human Colon Carcinoma) Tumor Xenograft Nude mice were implanted with 10 HT29 cells on their right flanks. Treatment was initiated once the tumor were palpable and were greater than 100-200 mm³. The mice were randomly sorted into 4 groups (n=8 per group). Group 1 received saline 3 times weekly for 4 weeks, i.v.; Group 2 received Abraxane™ at 10 mg/kg, daily for 5 days, i.p.; Group 3 received nab-rapamycin at 40 mg/kg, 3 times weekly for 4 weeks, i.v.; and Group 4 received both nab-rapamycin (40 mg/kg, 3 times weekly for 4 weeks, i.v.) and Abraxane™ (10 mg/kg, daily for 5 days, i.p.). As shown in FIG. 8, the tumor suppression was greater for the Abraxane™ plus nab-rapamycin combination therapy than for either single therapy group.

Example 23

Figure 9:
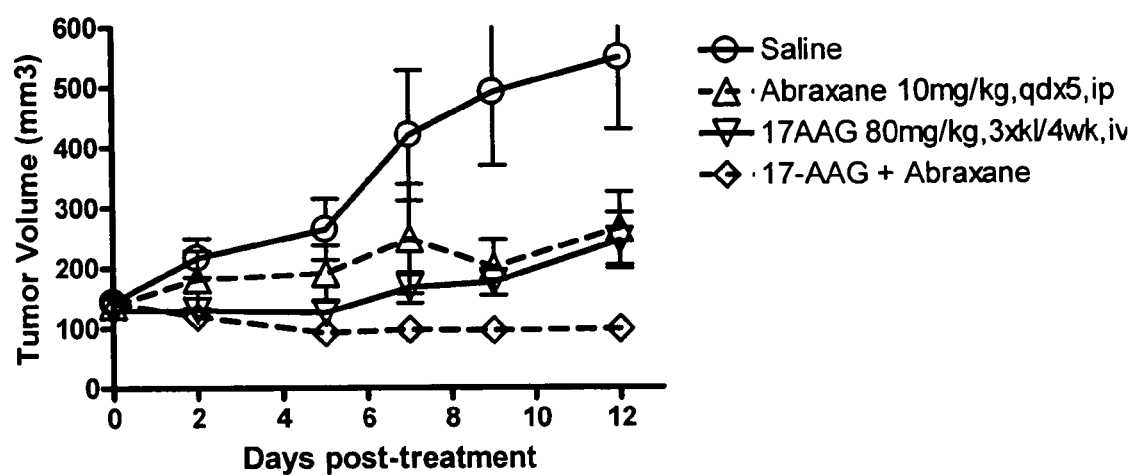
FIG. 9 shows the cytotoxic activity of nab-17-AAG in combination with Abraxane™ in a H358 human lung carcinoma xenograft model.

Cytotoxic Activity of nab-17-AAG in Combination with Abraxane™ Against H358 (Human Lung Carcinoma) Tumor Xenograft Nude mice were implanted with $10^7$ H358 cells on their right flanks. Treatment was initiated once the tumors were palpable and were greater than 100-200 mm³. The mice were randomly sorted into 4 groups (n=8 per group). Group 1 received saline 3 times weekly for 4 weeks, i.v.; Group 2 received Abraxane™ at 10 mg/kg, daily for 5 days, i.p.; Group 3 received nab-17-AAG at 80 mg/kg, 3 times weekly for 4 weeks, i.v.; and Group 4 received both nab-17-AAG (80 mg/kg, 3 times weekly for 4 weeks, i.v.) and Abraxane™ (10 mg/kg, daily for 5 days, i.p.). As shown in FIG. 9, the tumor suppression was greater for the nab-17-AAG plus Abraxane™ combination therapy than for either single therapy group.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating non-small cell lung cancer (NSCLC) in a human individual comprising administering to the individual:
   a) an effective amount of a composition comprising nanoparticles comprising paclitaxel coated with albumin, and
   b) an effective amount of a platinum-based agent, wherein the platinum-based agent is cisplatin or carboplatin, and wherein the nanoparticle composition is free of cremophor.

2. The method according to claim 1, wherein said platinum-based agent is carboplatin.

3. The method according to claim 1, wherein the composition comprising nanoparticles comprising paclitaxel coated with albumin and the platinum-based agent are administered simultaneously.

4. The method according to claim 1, wherein the composition comprising nanoparticles comprising paclitaxel coated with albumin and the platinum-based agent are administered sequentially.

5. The method according to claim 1, wherein the average diameter of the nanoparticles in the composition is no greater than about 200 nm.

6. The method according to claim 5, wherein the weight ratio of the albumin and paclitaxel in the nanoparticle composition is less than about 9:1.

7. The method according to claim 5, wherein the platinum-based agent is carboplatin.

8. The method according to claim 1, wherein the albumin is human serum albumin.

9. The method of claim 1, wherein the cancer is an advanced stage cancer.

10. The method of claim 1, wherein the dosage of paclitaxel in the nanoparticle composition is about 50 to about 400 mg/m$^2$.

11. The method of claim 1, wherein the nanoparticle composition is administered on a three week schedule and the dosage of paclitaxel in the nanoparticle composition is in the range of 100-400 mg/m$^2$.

12. The method of claim 1, wherein the nanoparticle composition is administered on a weekly schedule and the dosage of paclitaxel in the nanoparticle composition is in the range of 50-250 mg/m$^2$.

13. The method of claim 1, wherein the nanoparticle composition is administered on a three week schedule and the dosage of paclitaxel in the nanoparticle composition is in the range of 220-340 mg/m$^2$.

14. The method of claim 13, wherein the platinum-based agent is carboplatin.

15. The method of claim 1, wherein the nanoparticle composition is administered on a weekly schedule and the dosage of paclitaxel in the nanoparticle composition is in the range of 100-150 mg/m$^2$.

16. The method of claim 1, wherein the interval between each administration of the nanoparticle composition is no more than about a week.

17. The method of claim 1, wherein the weight ratio of the albumin and paclitaxel in the nanoparticle composition is about 18:1 or less.

18. The method of claim 5, wherein the weight ratio of the albumin and paclitaxel in the nanoparticle composition is about 18:1 or less.

19. The method of claim 5, wherein the weight ratio of albumin and paclitaxel in the nanoparticle composition is about 9:1 or less.

20. The method of claim 15, wherein the average diameter of the nanoparticles in the composition is no greater than about 200 nm.

21. The method of claim 20, wherein the weight ratio of albumin and paclitaxel in the nanoparticle composition is about 18:1 or less.

22. The method of claim 21, wherein the weight ratio of albumin and paclitaxel in the nanoparticle composition is about 9:1 or less.

23. The method of claim 22, wherein the weight ratio of albumin and paclitaxel in the nanoparticle composition is less than about 9:1.

24. The method of claim 19, wherein the platinum-based agent is carboplatin, and wherein the albumin is human serum albumin.

25. The method of claim 15, wherein the cancer is an advanced stage cancer.

26. The method of claim 15, wherein the dosage of paclitaxel in the nanoparticle composition is about 100 mg/m$^2$.

27. The method of claim 26, wherein the average diameter of the nanoparticles in the composition is no greater than about 200 nm.

28. The method of claim 27, wherein the weight ratio of albumin and paclitaxel in the nanoparticle composition is about 18:1 or less.

29. The method of claim 28, wherein the weight ratio of albumin and paclitaxel in the nanoparticle composition is about 9:1 or less.

30. The method of claim 29, wherein the weight ratio of albumin and paclitaxel in the nanoparticle composition is less than about 9:1.

31. The method of claim 18, wherein the platinum-based agent is carboplatin.

32. The method of claim 26, wherein the cancer is an advanced stage cancer.

33. The method of claim 1, wherein the platinum-based agent is cisplatin.

34. The method of claim 20, wherein the platinum-based agent is carboplatin.

* * * * *